US012662679B2

(12) United States Patent
Greenfield et al.

(10) Patent No.: US 12,662,679 B2
(45) Date of Patent: Jun. 23, 2026

(54) PRODUCTION OF FATTY ACID DERIVATIVES

(71) Applicant: Genomatica, Inc., San Diego, CA (US)

(72) Inventors: Derek L. Greenfield, South San Francisco, CA (US); Andreas W. Schirmer, Hayward, CA (US); Elizabeth J. Clarke, South San Francisco, CA (US); Eli S. Groban, South San Francisco, CA (US); Bernardo M. Da Costa, South San Francisco, CA (US); Zhihao Hu, Zhajalgang (CN); Kevin Holden, South San Francisco, CA (US); Noah Helman, South San Francisco, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 18/344,219

(22) Filed: Jun. 29, 2023

(65) Prior Publication Data

US 2024/0150774 A1      May 9, 2024

Related U.S. Application Data

(60) Continuation of application No. 17/335,812, filed on Jun. 1, 2021, now abandoned, which is a division of application No. 15/650,285, filed on Jul. 14, 2017, now Pat. No. 11,060,099, which is a division of application No. 14/390,378, filed as application No. PCT/US2013/035037 on Apr. 2, 2013, now abandoned.

(60) Provisional application No. 61/619,324, filed on Apr. 2, 2012.

(51) Int. Cl.
| | |
|---|---|
| *C12N 15/70* | (2006.01) |
| *C12N 1/21* | (2006.01) |
| *C12N 9/00* | (2006.01) |
| *C12N 9/02* | (2006.01) |
| *C12N 9/04* | (2006.01) |
| *C12N 9/10* | (2006.01) |
| *C12N 9/12* | (2006.01) |
| *C12N 9/88* | (2006.01) |
| *C12N 9/90* | (2006.01) |
| *C12P 7/04* | (2006.01) |
| *C12P 7/6409* | (2022.01) |
| *C12P 7/6436* | (2022.01) |

(52) U.S. Cl.
CPC ........... *C12N 15/70* (2013.01); *C12N 9/0006* (2013.01); *C12N 9/001* (2013.01); *C12N 9/1029* (2013.01); *C12N 9/1288* (2013.01); *C12N 9/88* (2013.01); *C12N 9/90* (2013.01); *C12N 9/93* (2013.01); *C12P 7/04* (2013.01); *C12P 7/6409* (2013.01); *C12P 7/6436* (2013.01); *C12Y 101/011* (2013.01); *C12Y*

*103/01009* (2013.01); *C12Y 103/0101* (2013.01); *C12Y 203/01039* (2013.01); *C12Y 203/01041* (2013.01); *C12Y 203/01179* (2013.01); *C12Y 203/0118* (2013.01); *C12Y 207/08007* (2013.01); *C12Y 402/01059* (2013.01); *C12Y 503/03014* (2013.01); *C12Y 604/01002* (2013.01)

(58) Field of Classification Search
None
See application file for complete search history.

(56) References Cited

U.S. PATENT DOCUMENTS

| | | | |
|---|---|---|---|
| 5,000,000 | A | 3/1991 | Ingram et al. |
| 5,028,539 | A | 7/1991 | Ingram et al. |
| 5,424,202 | A | 6/1995 | Ingram et al. |
| 5,482,846 | A | 1/1996 | Ingram et al. |
| 5,602,030 | A | 2/1997 | Ingram et al. |
| 5,939,250 | A | 8/1999 | Short |
| 5,965,408 | A | 10/1999 | Short |
| 7,192,735 | B2 | 3/2007 | Lambalot et al. |
| 7,897,369 | B2 | 3/2011 | Schmidt-Dannert et al. |
| 8,097,439 | B2 | 1/2012 | Alibhai et al. |
| 11,060,099 | B2 | 7/2021 | Greenfield et al. |
| 2003/0101485 | A1 | 5/2003 | Jinqing et al. |
| 2009/0140696 | A1 | 6/2009 | Okuto |
| 2010/0105963 | A1 | 4/2010 | Hu |
| 2010/0170826 | A1 | 7/2010 | Friedman et al. |
| 2010/0242345 | A1 | 9/2010 | Keasling et al. |
| 2010/0274033 | A1 | 10/2010 | Sanchez-Riera et al. |
| 2011/0111458 | A1 | 5/2011 | Masuda et al. |
| 2011/0151526 | A1 | 6/2011 | Saunders et al. |
| 2011/0162259 | A1 | 7/2011 | Gaertner |

(Continued)

FOREIGN PATENT DOCUMENTS

| | | |
|---|---|---|
| CN | 1295130 A | 5/2001 |
| CN | 101490241 A | 7/2009 |

(Continued)

OTHER PUBLICATIONS

GenBank, Accession No. BAA16180, 2008, www.nlm.nih.gov. (Year: 2008).*

(Continued)

*Primary Examiner* — Todd M Epstein
(74) *Attorney, Agent, or Firm* — Harness Dickey & Pierce P.L.C.

(57) ABSTRACT

The disclosure relates to recombinant host cells including strain modifications effective to improve titer, yield and/or productivity of fatty acid derivatives. The disclosure further relates to cell cultures including the recombinant host cells for the fermentative production of fatty acid derivatives and compositions thereof.

9 Claims, 18 Drawing Sheets

Specification includes a Sequence Listing.

(56) References Cited

U.S. PATENT DOCUMENTS

| | | | |
|---|---|---|---|
| 2011/0206630 A1 | 8/2011 | Rude | |
| 2012/0070868 A1* | 3/2012 | Lee | C12N 9/88 |
| | | | 435/254.11 |
| 2012/0116108 A1 | 5/2012 | Basu et al. | |
| 2015/0064782 A1 | 3/2015 | Greenfield et al. | |
| 2015/0299679 A1* | 10/2015 | Shumaker | C12N 9/18 |
| | | | 435/254.5 |
| 2016/0002681 A1* | 1/2016 | Simpson | C12P 7/6436 |
| | | | 435/254.2 |
| 2021/0348173 A1 | 11/2021 | Greenfiled et al. | |

FOREIGN PATENT DOCUMENTS

| | | | | | |
|---|---|---|---|---|---|
| EP | 2194119 A2 * | 6/2010 | | | C07C 31/125 |
| JP | 2010507369 A | 3/2010 | | | |
| JP | 2010526805 A | 8/2010 | | | |
| JP | 2012504963 A | 3/2012 | | | |
| WO | 91/16427 A1 | 10/1991 | | | |
| WO | 2007/136762 A2 | 11/2007 | | | |
| WO | 2008130437 A2 | 10/2008 | | | |
| WO | WO-2008119082 A2 * | 10/2008 | | | C07C 69/34 |
| WO | 2008147781 A2 | 12/2008 | | | |
| WO | 2009002480 A2 | 12/2008 | | | |
| WO | 2009085278 A1 | 7/2009 | | | |
| WO | 2009140695 A1 | 11/2009 | | | |
| WO | 2010042664 A1 | 4/2010 | | | |
| WO | 2010/062480 A2 | 6/2010 | | | |
| WO | 2010075483 A2 | 7/2010 | | | |
| WO | 2010/127318 A2 | 11/2010 | | | |
| WO | 2011038134 A1 | 3/2011 | | | |
| WO | 2012009660 A2 | 1/2012 | | | |
| WO | 2012019175 A2 | 2/2012 | | | |
| WO | 2013019647 A1 | 2/2013 | | | |
| WO | 2013152051 A2 | 10/2013 | | | |
| WO | 2013152052 A2 | 10/2013 | | | |

OTHER PUBLICATIONS

GenBank, Accession No. NP_418398.2, 2010, www.nlm.nih.gov. (Year: 2010).*

Jeon et al., Development of *Escherichia coli* MG1655 strains to produce long chain fatty acids by engineering fatty acid synthesis (FAS) metabolism, Enz. Microbial Technol. 49, 2011, 44-51. (Year: 2011).*

Yu et al., In vitro reconstitution and steady-state analysis of the fatty acid synthase from *Escherichia coli*, Proc. Natl. Acad. Sci. USA 108, 2011, 18643-48. (Year: 2011).*

Massengo-Tiasse et al., Vibrio cholerae FabV Defines a New Class of Enoyl-Acyl Carrier Protein Reductase, J. Biol. Chem. 283, 2008, 1308-16. (Year: 2008).*

Cao et al., Increasing unsaturated fatty acid contents in *Escherichia coli* by coexpression of three different genes, Appl. Microb. Biotechnol. 87, 2010, 271-80. (Year: 2010).*

Feng et al., *Escherichia coli* Unsaturated Fatty Acid Synthesis, JBC 284, 2009, 29526-35. (Year: 2009).*

Uniprot, Accession No. P64105, 2005, www.uniprot.org. (Year: 2005).*

Amann et al., "Tightly regulated tac promoter vectors useful for the expression of unfused and fused proteins in *Escherichia coli*," Gene, 69: 301-315 (1988).

Arkin et al. (1992) Proc. Natl. Acad. Sci. U.S.A. 89:7811-7815.

Arnold, "Protein engineering for unusual environments," Curr. Opin. Biotech. 4: 450-455 (1993).

Baldari et al., "A novel leader peptide which allows efficient secretion of a fragment of human interleukin 1 beta in *Saccharomyces cerevisiae*," EMBO J. 6(1): 229-234 (1987).

Bergler et al., "Protein EnvM is the NADH-dependent Enoyl-ACP Reductase (FabI) of *Escherichia coli*," J. Biol. Chem., 269(8): 5943-5946 (1994).

Bergler et al., "The enoyl-[acyl-carrier-protein] reductase (FabI) of *Escherichia coli*, which catalyzes a key regulatory step in fatty acid biosynthesis, accepts NADH and NADPH as cofactors and is inhibited by palmitoyl-CoA", Eur. J. Biochem. 242, 1996, 689-694.

Bowie et al. "Deciphering the Message in Protein Sequences: Tolerance to Amino Acid Substitutions," (1990) Science, 247:1306-1310.

Caldwell et al., "Randomization of Genes by PCR Mutagenesis," PCR Methods Applic. 2: 28-33 (1992).

Communication issued on EP Appl. 13715879.6, mailed Jun. 1, 2016.

Communication issued on EP Application 13715879.6, mailed May 12, 2017.

Cronan et al., "FadR, transcriptional co-ordination of metabolic expediency," Mol. Microbial. 29(4): 937-943 (1998).

Datsenko et al., "One-step Inactivation of Chromosomal Genes in *Escherichia coli* K-12 using PCR Products," Proc. Natl. Acad. Sci USA 97: 6640-6645 (2000).

Davis et al., "Overproduction of Acetyl-CoA Carboxylase Activity Increases the Rete of Fatty Acid Biosynthesis in *Escherichia coli*," J. Biol. Chem., 2000, vol. 275, pp. 28593-28598.

Decision of Rejection issued on Japanese Application2 015-504687, mailed Dec. 4, 2017.

Decision of Rejection in JP Patent No. 2018-072000 dated Jan. 8, 2020 (with English translation) (9 pages).

Delegrave et al., "Searching Sequence Space to Engineer Proteins: Exponential Ensemble Mutagenesis," Biotech. Res, 11: 1548-1552 (1993).

Exam Report issued on Malaysian Appl. PI 2014002773, mailed Sep. 15, 2017.

Examination Report issue on Australian Application 2013243601, mailed Oct. 5, 2017.

Examination Report issued on Indonesian Appl. P-00201406815, mailed Dec. 29, 2017.

Extended European Search Report in EP Patent Application No. 19211601.0 dated May 14, 2020 (9 pages).

Final Office Action on U.S. Appl. No. 14/390,378 mailed Jan. 19, 2017.

First Examination Report on IN Patent Application No. 9107/DELNP/2014 dated Aug. 28, 2019, 7 pages.

Flores et al., "Expression of PEP carboxylase from *Escherichia coli* complements the phenotypic; effects of pyruvate carboxylase mutations in *Saccharomyces cerevisiae*," FEBS Letters 412, 1997, pp. 531-534.

Fourth Office Action in CN Patent Application No. 201380026304.9, dated Jan. 5, 2018 (16 pages with English translation).

Gaviglia et al., "Rat Long Chain Acyl-CoA Synthetase 5, but Not 1, 2, 3, or 4, Complements *Escherichia coli* fadD," J. Biol. Chem. 279(12): 11163-11169 (2004).

GenBank, Accession No. 460041.1, 2011, VWVW.ncbi.nlm.nih. gov.

GenBank, Accession No. AAC74178.1, 2010, VWWW.ncbi.nlm. nih.gov.

GenBank, Accession No. BAA16180, 2008, VWVW.ncbi.nlm.nih. gov.

GenBank, Accession No. NP_350156.1, 2010, VWVW.ncbi.nlm. nih.gov.

GenBank, Accession No. NP_416826.1, 2011, www.ncbi.nlm.nih. gov.

GenBank, Accession No. NP_460163.1, 2011, www.ncbi.nlm.nih. gov.

GenBank, Accession No. NP_460164.1, 2011, www.ncbi.nlm.nih. gov.

GenBank, Accession No. NP_460165.1, 2011, www.ncbi.nlm.nih. gov.

GenBank, Accession No. YP_001217283.2, 2010, www.ncbi.nlm. nih.gov.

Goeddel, Gene Expression Technology: Methods in Enzymology, vol. 185, Academic Press, San Diego, Calif. (1990).

Gokarn et al., "Metabolic Analysis of *Escherichia coli* in the Presence and Absence of the; Carboxylating Enzymes Phosphoenolpyruvate Carboxylase and Pyruvate Carboxylase," Applied and Environmental Microbiology, May 2000, pp. 1844-1850.

(56)         References Cited

OTHER PUBLICATIONS

Grosjean et al., "Preferential codon usage in prokaryotic genes: the optimal codon-anticodon; interaction energy and the selective codon usage in efficiently expressed genes," Gene. 18: 199-209 (1982).

Handke, P., et al., "Application and engineering of fatty acid biosynthesis in *Escherichia coli* for advanced fuels and chemicals," Metabolic Engineering, 13: 28-37 (2011).

Heath et al., "Inhibition of beta.-Ketoacyl-Acyl Carrier Protein Synthase III (FabH) by Acyl-Acyl Carrier Protein in *Escherichia coli*", J.Biol. Chem.271(18):10996-11000 (1996).

Heath et al., "Regulation of Fatty Acid Elongation and Initiation by Acyl-Acyl Carrier Protein in *Escherichia coli*", J. Biol.Chem. vol. 271(4): 1833-1836 (1996).

Heath, "The Enoly-[acyl-carrier-protein] Reductases Fabl and FabL from Bacillus subtilis," Journal of Biological Chemistry, vol. 275, No. 51, Sep. 27, 2000, pp. 40128-40133.

International Preliminary Report on Patentability on PCT/US2013/035037, dated Oct. 7, 2014, 13 pages.

International Search Report and Written Opinion on PCT/US2013/035037, mailed Oct. 31, 2013.

Ku et al., "High-level expression of maize phosphoenolpyruvate carboxylase in transgenic rice plants," Nature Biotechnology, vol. 17, Jan. 1999, pp. 76-80.

Kurjan et al., Struture of a Yeast Pheromone Gene (MFx): A Putative x-Factor precursor Contains Four Tandem Copies of Mature x-Factor, Cell, vol. 30, pp. 933-943 (1982).

Lennen et al., Engineering *Escherichia coli* to synthesize free fatty acids, Trends in Biotechnol., 2012, 30, 659-67.

Leung et al. "A Journal of Methods in Cell and Molecular Biology," Technique 1:(1): 11-15 (1989).

Liu et al., "Quantitative analysis and engineering of fatty acid biosynthesis in *E. coli*," Metabolic Eng. 2010, vol. 12, pp. 378-386.

Liu et al., Fatty acid production in genetically modified cyanobacteria, Proc. Natl. Acad. Sci. USA, 2011, 108, 6800-6904.

Lu et al., Overproduction of free fatty acids in *E. coli*: Implications for biodiesel production, Metabolic Eng., 2008, 10, 333-39.

Lucklow et al., "High level expression of nonfused foreign genes with Autographa californica nuclear polyhedrosis virus expression vectors," Virology 170(1): 31-39 (1989).

Maniatis et al., "Regulation of Inducible and Tissue-Specific Gene Expression," Science 236: 1237-1245 (1987).

Massengo-Tiasse et al., "Vibrio cholerae FabV Defines a New Class of Enoyl-Acyl Carrier Protein Reductase", J. Biol. Chem. 283(3): 1308-1316 (2008).

Mori et al., A SecE Mutation That Modulates SecY-SecE Translocase Assembly, Identified as a Specific Suppressor of SecY Defects, J. Bacterial., 2003, 185, 948-56.

Needleman and Wunsch, "A General Method Applicable to the Search for Similarities in the Amino Acid Sequence of Two Proteins," J. Mol. Biol. 48:443-453 (1970).

Non-Final Office Action on U.S. Appl. No. 14/390,378 mailed May 23, 2016.

Notice of Reasons for Refusal in KR 10-2014-7030467 dated Mar. 2, 2020 (5 pages) (with English Translation).

Notice of Reasons for Rejection issued on Japanese application 2015-504687, mailed Jan. 19, 2017, English translation.

Office Action from corresponding JP Application No. 2020081804 dated Aug. 2, 2021.

Office Action from corresponding Korean Application No. 10-2020-7015194 dated Apr. 15, 2021.

Office Action in CA Patent Application No. 2883968 dated Apr. 28, 2020 (3 pages).

Office Action in CO Patent Application No. 14-240.053, dated May 12, 2016, (20 pages) (with English translation).

Office Action in CO Patent Application No. 14-240.053, dated Nov. 11, 2016, (14 pages) (with English translation).

Office Action issued on Chinese Application 201380026304.9, mailed Apr. 1, 2017, English translation only.

Office Action issued on Chinese Application 201380026304.9, mailed Dec. 29, 2015, English translation provided.

Office Action on Application No. MX/a/2014/011905, dated Dec. 3, 2018, 4 pages.

Office Action on CN Application No. 201380026304.9, dated Jan. 5, 2018, 8 pages.

Office Action on CN Application No. 201380026304.9, dated Sep. 9, 2016, 9 pages (with translation).

Office Action on CN Application No. 201380026304.9, dated Oct. 26, 2018, 12 pages (with translation).

Office Action on CO Application 14-240.053, dated May 12, 2016, 10 pages.

Office Action on CO Application No. 14-240.053, dated Nov. 11, 2016, 7 pages.

Office Action on ID Application No. P00201406815, dated Apr. 12, 2018, 3 pages (with translation).

Palmeros et al., "A family of removable cassets designed to obtain antiobiotic-resistance-free genomic modifications of *Escherichia coli* and other bacteria," Gene, vol. 247, pp. 255-264, 2000.

Peng et al., Metabolic flux analysis for a ppc mutant *Escherichia coli* based on 13C-labelling experiments together with enzyme activity assays and intracellular metabolite measurements, FEMS Microbial. Lett., 2004, 235, 17-23.

Preliminary Office Action in BR Patent Application No. 112014024675.0 dated Sep. 2, 2019, 6 pages (translation).

Quadri, L.E.N., et al., "Characterization of Sfp, a Bacillus subtilis Phosphopantetheinyl Transferase for Peptidyl Carrier Protein Domains in Peptide Synthetases," Biochemisty, 37: 1585-1595 (1998).

Reidhaar-Olson et al., "Combinatorial Cassette Mutagenesis as a Probe of the Informational Content of Protein Sequences," Science 241: 53-57 (1988).

Rosenberg, "Multiple Sequence Alignment Accuracy and Evolutionary Distance Estimation," BMC Bioinformatics 6: 278 (2005).

Sambrook et al., "Molecular Cloning: A Laboratory Manual," 1989, 2nd Ed., Cold Spring Harbor Laboratory Press, Cold Spring Harbor, NY.

Sanchez, Cesar, et al., "Cloning and characterization of a phosphopantetheinyl transferase from Streptomyces verticillus ATCC15003, the producer of the hybrid peptide-polyketide antitumor drug bleomycin," Chemistry & Biology, vol. 8, 2001, pp. 725-738.

Schultz et al., "Expression and secretion in yeast of a 400-kDa envelope glycoprotein derived from Epstein-Barr virus," Gene 54: 113-123 (1987).

Second Office Action in CA Patent Application No. 2,883,968 dated Apr. 23, 2019, 3 pages.

Second Office Action in MX Patent Application No. MX/a/2014/011905, dated Dec. 3, 2018 (with English language comments; no Office Action translation available) (8 pages).

Smith et al., "Production of Human Beta Interferon in Insect Cells Infected with a Vaculovirus Expression Vector," Mol. Cell Biol. 3(12): 2156-2165 (1983).

Smith et al., "Single-step purification of polypeptides expressed in *Escherichia coli* as fusions with glutathione S-transferase," Gene. 67: 31-40 (1988).

Stemmer, "DNA shuffling by random fragmentation and reassembly: In vitro recombination for molecular evolution," Proc. Natl. Acad. Sci. USA. 91: 10747-10751 (1994).

Studier et al., "Use of T7 RNA Polymerase to Direct Expression of Cloned Genes," Methods in Enzymology, 185: 60-89 (1990).

Studier et al., Gene Expression Technology: Methods in Enzymology 185, Academic Press, San Diego, CA, pp. 60-89 (1990).

Substantive Examination Adverse Report in My PI2014002773 dated Feb. 4, 2020 (2 pages).

Wang et al., "The Gene Locus yijP Contributes to *Escherichia coli* K1 Invasion of Brain Microvascular Endothelial Cells," Infection and Immunity, Sep. 1999, pp. 4751-4756.

Wang et al., The gene locus yijP contributes to *Escherichia coli* K1 invasion of brain microvascular endothelial cells, Infect. Immun., 1999, 67, 4751-56.

Zha et al., "Improving cellular malonyl-CoA level in *Escherichia coli* via metabolic engineering," Metabolic eng., 2009, vol. 11, pp. 192-198.

Zhang et al.,j"Transcriptional Analysis of Essential Genes of the *Escherichia coli* Fatty Acid Biosynthesis Gene Cluster by Func-

(56) References Cited

OTHER PUBLICATIONS tional Replacement with the Analogous *Salmonella typhimurium* Gene Cluster," J. Bacteriol., 1998, 180, pp. 3295-3303.

Zhu et al., "Functions of the Clostridium acetobutylicium FabF and FabZ proteins in unsaturated fatty acid biosynthesis", BMC Microbiology 9:119 (2009).

Non-Final Office Action issued in U.S. Appl. No. 15/650,285 dated Dec. 4, 2020.

Final Office Action issued in U.S. Appl. No. 15/650,285 dated Feb. 13, 2020.

Yu, Xingye et al. (2011). In vitro reconstitution and steady-state analysis of the fatty acid synthase from *Escherichia coli*. Proceedings of the National Academy of Sciences, 108(46): 18643-18648.

Jeon, Eunyoung et al. (2011). Development of *Escherichia coli* MG1655 strains to produce long chain fatty acids by engineering fatty acid synthesis (FAS) metabolism. Enzyme and Microbial Technology, 49(1): 44-51.

Zhang, Xiujun et al. (2012). Improving fatty acid production in *Escherichia coli* through the overexpression of malonyl coA Acyl carrier protein transacylase. Biotechnology Progress, 28(1): 60-65.

* cited by examiner

FIG. 1

DAM1_377 with *C. glutamicum* Acc and BirA expression:
Mal-CoA in log phase

DAM1-i377: Short-chain CoA levels in log phase, acc-panK coexpression

Duplicate plate screen at 32°C

SEQUENCE LISTING

```
Sequence total quantity: 64
SEQ ID NO: 1              moltype = DNA   length = 1232
FEATURE                  Location/Qualifiers
misc_feature             1..1232
                         note = Synthetic polynucleotide
source                   1..1232
                         mol_type = other DNA
```

-continued

```
                       organism = synthetic construct
SEQUENCE: 1
ttgtccatct ttatataatt tgggggtagg gtgttcttta tgtaaaaaaa acgttttagg    60
atgcatatgg cggccgcata acttcgtata gcatacatta tacgaagtta tctagagttg   120
catgcctgca ggtccgctta ttatcactta ttcaggcgta gcaaccaggc gtttaagggc   180
accaataact gccttaaaaa aattacgccc cgccctgcca ctcatcgcag tactgttgta   240
attcattaag cattctgccg acatggaagc catcacaaac ggcatgatga acctgaatcg   300
ccagcggcat cagcaccttg tcgccttgcg tataatattt gcccatggtg aaaacggggg   360
cgaagaagtt gtccatattg gccacgttta aatcaaaact ggtgaaactc acccagggat   420
tggctgagac gaaaaacata ttctcaataa acccctttagg gaaataggcc aggttttcac   480
cgtaacacgc cacatcttgc gaatatatgt gtagaaactg ccggaaatcg tcgtggtatt   540
cactccagag cgatgaaaac gtttcagttt gctcatggaa aacggtgtaa caaggggtgaa   600
cactatccca tatcaccagc tcaccgtctt tcattgccat acggaattcc ggatgagcat   660
tcatcaggcg ggcaagaatg tgaataaagg ccggataaaa cttgtgctta tttttcttta   720
cggtctttaa aaaggccgta atatccagct gaacggtctg gttataggta cattgagcaa   780
ctgactgaaa tgcctcaaaa tgttctttac gatgccattg ggatatatca acggtggtat   840
atccagtgat ttttttctcc attttagctt ccttagctcc tgaaaatctc gataactcaa   900
aaaatacgcc cggtagtgat cttatttcat tatggtgaaa gttggaacct cttacgtgcc   960
gatcaacgtc tcattttcgc caaaagtgg cccaggctt cccggtatca acagggacac    1020
caggatttat ttattctgcg aagtgatctt ccgtcacagg tatttattcg actctagata   1080
acttcgtata gcatacatta tacgaagtta tggatccagc ttatcgatac cgtcaaacaa   1140
atcataaaaa atttatttgc tttcaggaaa attttttctgt ataatagatt caattgcgat   1200
gacgacgaac acgcacctgc aggaggagac ca                                 1232

SEQ ID NO: 2              moltype = DNA   length = 232
FEATURE                  Location/Qualifiers
misc_feature             1..232
                         note = Synthetic polynucleotide
source                   1..232
                         mol_type = other DNA
                         organism = synthetic construct
SEQUENCE: 2
ttgtccatct ttatataatt tgggggtagg gtgttcttta tgtaaaaaaa acgttttagg    60
atgcatatgg cggccgcata acttcgtata gcatacatta tacgaagtta tggatccagc   120
ttatcgatac cgtcaaacaa atcataaaaa atttatttgc tttcaggaaa attttttctgt   180
ataatagatt caattgcgat gacgacgaac acgcacctgc aggaggagac ca           232

SEQ ID NO: 3              moltype = AA   length = 340
FEATURE                  Location/Qualifiers
source                   1..340
                         mol_type = protein
                         organism = Acinetobacter sp.
SEQUENCE: 3
MSNHQIRAYA AMQAGEQVVP YQFDAGELKA HQVEVKVEYC GLCHSDLSVI NNEWQSSVYP    60
AVAGHEIIGT IIALGSEAKG LKLGQRVGIG WTAETCQACD PCIGGNQVLC TGEKKATIIG   120
HAGGGFADKVR AGWQWVIPLP DDLDPESAGP LLCGGITVLD PLLKHKIQAT HHVGVIGIGG  180
LGHIAIKLLK AWGCEITAFS SNPDKTEELK ANGADQVVNS RDAQAIKGTR WKLIILSTAN   240
GTLNVKAYLN TLAPKGSLHF LGVTLEPIPV SVGAIMGGAK SVTSSPTGSP LALRQLLQFA   300
ARKNIAPQVE LFPMSQLNEA IERLHSGQAR YRIVLKADFD                         340

SEQ ID NO: 4              moltype = AA   length = 314
FEATURE                  Location/Qualifiers
source                   1..314
                         mol_type = protein
                         organism = Acinetobacter sp.
SEQUENCE: 4
MATTNVIHAY AAMQAGEALV PYSFDAGELQ PHQVEVKVEY CGLCHSDVSV LNNEWHSSVY    60
PVVAGHEVIG TITQLGSEAK GLKIGQRVGI GWTAESCQAC DQCISGQQVL CTGENTATII   120
GHAGGGFADKV RAGWQWVIPL PDELDPTSAG PLLCGGITVF DPILKHQIQA IHHVAVIGIG  180
GLGHMAIKLL KAWGCEITAF SSNPNKTDEL KAMGADHVVN SRDDAEIKSQ QGKFDLLLST   240
VNVPLNWNAY LNTLAPNGTF HFLGVVMEPI PVPVGALLGG AKSLTASPTG SPAALRKLLE   300
FAARKNIAPQ IEMY                                                     314

SEQ ID NO: 5              moltype = DNA   length = 1020
FEATURE                  Location/Qualifiers
source                   1..1020
                         mol_type = unassigned DNA
                         organism = Escherichia coli
SEQUENCE: 5
atgtcgatga taaaaagcta tgccgcaaaa gaagcgggcg gcgaactgga agtttatgag    60
tacgatcccg gtgagctgag gccacaagat gttgaagtgc aggtggatta ctgcgggatc   120
tgccattccg atctgtcgat gatcgataac gaatggggat tttcacaata tccgctggtt   180
gccgggcatg aggtgattgg gcgcgtggtg gcactcggga gcgccgcgca ggataaaggt   240
ttgcaggtcg gtcagcgtgt cgggattggc tggacggcgc gtagctgtgg tcactgcgac   300
gcctgtatta gcggtaatca gatcaactgc gagcaaggtg cggtgccgac gattatgaat   360
cgcggtggct ttgccgagaa gttgcgtgcg gactggcaat gggtgattcc actgccagaa   420
aatattgata tcgagtccgc cgggccgctg ttgtgcggcg gtatcacggt ctttaaacca   480
ctgttgatgc accatatcac tgctaccagc cgcgttgggg taattggtat tggcgggctg   540
gggcatatcg ctataaaact tctgcacgca atgggatgcg aggtgacagc ctttagttct   600
```

```
aatccggcga aagagcagga agtgctggcg atgggtgccg ataaagtggt gaatagccgc   660
gatccgcagg cactgaaagc actggcgggg cagtttgatc tcattatcaa caccgtcaac   720
gtcagcctcg actggcagcc ctattttgag gcgctgacct atggcggtaa tttccatacg   780
gtcggtgcgg ttctcacgcc gctgtctgtt ccggccttta cgttaattgc gggcgatcgc   840
agcgtctctg gttctgctac cggcacgcct tatgagctgc gtaagctgat gcgttttgcc   900
gcccgcagca aggttgcgcc gaccaccgaa ctgttcccga tgtcgaaaat taacgacgcg   960
atccagcatg tgcgcgacgg taaggcgcgt taccgcgtgg tgttgaaagc cgatttttga  1020
```

```
SEQ ID NO: 6            moltype = AA   length = 473
FEATURE                 Location/Qualifiers
source                  1..473
                        mol_type = protein
                        organism = Marinobacter hydrocarbonoclasticus
SEQUENCE: 6
MKRLGTLDAS WLAVESEDTP MHVGTLQIFS LPEGAPETFL RDMVTRMKEA GDVAPPWGYK    60
LAWSGFLGRV IAPAWKVDKD IDLDYHVRHS ALPRPGGERE LGILVSRLHS NPLDFSRPLW   120
ECHVIEGLEN NRFALYTKMH HSMIDGISGV RLMQRVLTTD PERCNMPPPW TVRPHQRRGA   180
KTDKEASVPA AVSQAMDALK LQADMAPRLW QAGNRLVHSV RHPEDGLTAP FTGPVSVLNH   240
RVTAQRRFAT QHYQLDRLKN LAHASGGSLN DIVLYLCGTA LRRFLAEQNN LPDTPLTAGI   300
PVNIRPADDE GTGTQISFMI ASLATDEADP LNRLQQIKTS TRRAKEHLQK LPKSALTQYT   360
MLLMSPYILQ LMSGLGGRMR PVFNVTISNV PGPEGTLYYE GARLEAMYPV SLIAHGGALN   420
ITCLSYAGSL NFGFTGCRDT LPSMQKLAVY TGEALDELES LILPPKKRAR TRK          473
```

```
SEQ ID NO: 7            moltype = AA   length = 455
FEATURE                 Location/Qualifiers
source                  1..455
                        mol_type = protein
                        organism = Marinobacter hydrocarbonoclasticus
SEQUENCE: 7
MTPLNPTDQL FLWLEKRQQP MHVGGLQLFS FPEGAPDDYV AQLADQLRQK TEVTAPFNQR    60
LSYRLGQPVW VEDEHLDLEH HFRFEALPTP GRIRELLSFV SAEHSHLMDR ERPMWEVHLI   120
EGLKDRQFAL YTKVHHSLVD GVSAMRMATR MLSENPDEHG MPPIWDLPCL SRDRGESDGH   180
SLWRSVTHLL GLSDRQLGTI PTVAKELLKT INQARKDPAY DSIFHAPRCM LNQKITGSRR   240
FAAQSWCLKR IRAVCEAYGT TVNDVVTAMC AAALRTYLMN QDALPEKPLV AFVPVSLRRD   300
DSSGGNQVGV ILASLHTDVQ DAGERLLKIH HGMEEAKQRY RHMSPEEIVN YTALTLAPAA   360
FHLLTGLAPK WQTFNVVISN VPGPSRPLYW NGAKLEGMYP VSIDMDRLAL NMTLTSYNDQ   420
VEFGLIGCRR TLPSLQRMLD YLEQGLAELE LNAGL                              455
```

```
SEQ ID NO: 8            moltype = AA   length = 457
FEATURE                 Location/Qualifiers
source                  1..457
                        mol_type = protein
                        organism = Alcanivorax borkumensis
SEQUENCE: 8
MKALSPVDQL FLWLEKRQQP MHVGGLQLFS FPEGAGPKYV SELAQQMRDY CHPVAPFNQR    60
LTRRLGQYYW TRDKQFDIDH HFRHEALPKP GRIRELLSLV SAEHSNLLDR ERPMWEAHLI   120
EGIRGRQFAL YYKIHHSVMD GISAMRIASK TLSTDPSERE MAPAWAFNTK KRSRSLPSNP   180
VDMASSMARL TASISKQAAT VPGLAREVYK VTQKAKKDEN YVSIFQAPDT ILNNTITGSR   240
RFAAQSFPLP RLKVIAKAYN CTINTVVLSM CGHALREYLI SQHALPDEPL IAMVPMSLRQ   300
DDSTGGNQIG MILANLGTHI CDPANRLRVI HDSVEEAKSR FSQMSPEEIL NFTALTMAPT   360
GLNLLTGLAP KWRAFNVVIS NIPGPKEPLY WNGAQLQGVY PVSIALDRIA LNITLTSYVD   420
QMEFGLIACR RTLPSMQRLL DYLEQSIREL EIGAGIK                            457
```

```
SEQ ID NO: 9            moltype = DNA   length = 70
FEATURE                 Location/Qualifiers
misc_feature            1..70
                        note = Synthetic oligonucleotide
source                  1..70
                        mol_type = other DNA
                        organism = synthetic construct
SEQUENCE: 9
aaaaacagca acaatgtgag ctttgttgta attatattgt aaacatattg attccgggga    60
tccgtcgacc                                                           70
```

```
SEQ ID NO: 10           moltype = DNA   length = 68
FEATURE                 Location/Qualifiers
misc_feature            1..68
                        note = Synthetic oligonucleotide
source                  1..68
                        mol_type = other DNA
                        organism = synthetic construct
SEQUENCE: 10
aaacggagcc tttcggctcc gttattcatt tacgcggctt caactttcct gtaggctgga    60
gctgcttc                                                             68
```

```
SEQ ID NO: 11           moltype = DNA   length = 23
FEATURE                 Location/Qualifiers
misc_feature            1..23
                        note = Synthetic oligonucleotide
```

-continued

```
source                  1..23
                        mol_type = other DNA
                        organism = synthetic construct
SEQUENCE: 11
cgggcaggtg ctatgaccag gac                                             23

SEQ ID NO: 12           moltype = DNA   length = 23
FEATURE                 Location/Qualifiers
misc_feature            1..23
                        note = Synthetic oligonucleotide
source                  1..23
                        mol_type = other DNA
                        organism = synthetic construct
SEQUENCE: 12
cgcggcgttg accggcagcc tgg                                             23

SEQ ID NO: 13           moltype = DNA   length = 60
FEATURE                 Location/Qualifiers
misc_feature            1..60
                        note = Synthetic oligonucleotide
source                  1..60
                        mol_type = other DNA
                        organism = synthetic construct
SEQUENCE: 13
ccttggcatt ggcaatttga gaattcgagg aggaaaacta aatgaccatt tcctcacctt  60

SEQ ID NO: 14           moltype = DNA   length = 60
FEATURE                 Location/Qualifiers
misc_feature            1..60
                        note = Synthetic oligonucleotide
source                  1..60
                        mol_type = other DNA
                        organism = synthetic construct
SEQUENCE: 14
ttttgttcgg gcccaagctt ttattgcaaa cgcagatgcg tgatttcacc cgcattcagc  60

SEQ ID NO: 15           moltype = DNA   length = 60
FEATURE                 Location/Qualifiers
misc_feature            1..60
                        note = Synthetic oligonucleotide
source                  1..60
                        mol_type = other DNA
                        organism = synthetic construct
SEQUENCE: 15
cgggcccaag cttcgaattc ttattgcaaa cgcagatgcg tgatttcacc cgcattcagc  60

SEQ ID NO: 16           moltype = DNA   length = 60
FEATURE                 Location/Qualifiers
misc_feature            1..60
                        note = Synthetic oligonucleotide
source                  1..60
                        mol_type = other DNA
                        organism = synthetic construct
SEQUENCE: 16
gaatagcgcc gtcgacgagg aggaaaacta aatgaccatt tcctcacctt tgattgacgt  60

SEQ ID NO: 17           moltype = DNA   length = 60
FEATURE                 Location/Qualifiers
misc_feature            1..60
                        note = Synthetic oligonucleotide
source                  1..60
                        mol_type = other DNA
                        organism = synthetic construct
SEQUENCE: 17
tgatgatgat gatggtcgac ttattgcaaa cgcagatgcg tgatttcacc cgcattcagc  60

SEQ ID NO: 18           moltype = DNA   length = 4250
FEATURE                 Location/Qualifiers
misc_feature            1..4250
                        note = Synthetic polynucleotide
source                  1..4250
                        mol_type = other DNA
                        organism = synthetic construct
SEQUENCE: 18
atgaccattt cctcaccttt gattgacgtc gccaaccttc cagacatcaa caccactgcc  60
ggcaagatcg ccgaccttaa ggctcgccgc gcggaagccc atttccccat gggtgaaaag  120
gcagtagaga aggtccacgc tgctggacgc ctcactgccc gtgagcgctt ggattactta  180
ctcgatgagg gctccttcat cgagaccgat cagctggctc gccaccgcac caccgctttc  240
ggcctgggcg ctaagcgtcc tgcaaccgac ggcatcgtga ccggctgggg caccattgat  300
```

-continued

```
ggacgcgaag tctgcatctt ctcgcaggac ggcaccgtat tcggtggcgc gcttggtgag   360
gtgtacggcg aaaagatgat caagatcatg gagctggcaa tcgacaccgg ccgcccattg   420
atcggtcttt acgaaggcgc tggcgctcgt attcaggacg gcgctgtctc cctggacttc   480
atttcccaga ccttctacca aaacattcag gcttctggcg ttatcccaca gatctccgtc   540
atcatgggcg catgtgcagg tggcaacgct tacggcccag ctctgaccga cttcgtggtc   600
atggtggaca agacctccaa gatgttcgtt accggcccag acgtgatcaa gaccgtcacc   660
ggcgaggaaa tcacccagga gagcttggc ggagcaacca cccacatggt gaccgctggt   720
aactcccact acaccgctgc gaccgatgag gaagcactgg attgggtaca ggacctggtg   780
tccttcctcc catccaacaa tcgctcctac gcaccgatgg aagacttcga cgaggaagaa   840
ggcggcgttg aagaaaacat caccgctgac gatctgaagc tcgacgagat catcccagat   900
tccgcgaccg ttccttacga cgtccgcgat gtcatcgaat gcctcaccga cgatggcgaa   960
tacctggaaa tccaggcaga ccgcgcagaa aacgttgtta ttgcattcgg ccgcatcgaa  1020
ggccagtccg ttggctttgt tgccaaccag ccaacccagt tcgctggctg cctggacatc  1080
gactcctctg agaaggcagc tcgcttcgtc cgcacctgcg acgcgttcaa catcccaatc  1140
gtcatgcttg tcgacgtccc cggcttcctc ccaggcgcag gccaggagta cggtggcatt  1200
ctgcgtcgtg gcgcaaagct gctctacgca tacggcgaag caaccgttcc aaagatcacc  1260
gtcaccatgc gtaaggctta cggcggagcg tactgcgtga tgggttccaa gggcttgggc  1320
tctgacatca accttgcatg gccaaccgca cagatcgccg tcatgggcgc tgctggcgca  1380
gttggattca tctaccgcaa ggagctcatg gcagctgatg ccaagggcct cgataccgta  1440
gctctggcta agtccttcga gcgcgagtat gaagaccaca tgctcaaccc gtaccacgct  1500
gcagaacgtg gcctgatcga cgccgtgatc ctgccaagcg aaacccgcgg acagatttcc  1560
cgcaaccttc gcctgctcaa gcacaagaac gtcactcgcc ctgctcgcaa gcacggcaac  1620
atgccactgt aaggaggaaa actaaatgtc agtcgagact cgcaagatca ccaaggttcc  1680
tgtcgctaac cgtggtgaga ttgcaatccg cgtgttccgt gcagctcgag atgaaggcat  1740
cggatctgtc gccgtctacg cagagccaga tgcagatgca ccattcgtgt catatgcaga  1800
cgaggctttt gccctcggtg gccaaacatc cgctgagtcc taccttgtca ttgacaagat  1860
catcgatgcg gcccgcaagt ccggcgccga cgccatccac cccggctacg gcttcctcgc  1920
agaaaacgct gacttcgcag aagcagtcat caacgaaggc ctgatctgga ttggaccttc  1980
acctgagtcc atccgctccc tcggcgacaa ggtcaccgct cgccacatcg cagataccgc  2040
caaggctcca atggctcctg gcaccaagga accagtaaaa gacgcagcag aagttgtggc  2100
tttcgctgaa gaattcggtc tcccaatcgc catcaaggca gctttcggtg gcggcggacg  2160
tggcatgaag gttgcctaca agatggaaga agtcgctgac ctcttcgagt ccgcaacccg  2220
tgaagcaacc gcagcgttcg gccgcggcga gtgcttcgtg gagcgctacc tggacaaggc  2280
acgccacgtt gaggctcagg tcatcgccga taagcacgac aacgttgttg tcgccggaac  2340
ccgtgactgc tccctgcagc gccgtttcca gaagctcgtc gaagaagcac cagcaccatt  2400
cctcaccgat gaccagcgcg agcgtctcca ctcctccgcg aaggctatct gtaaggaagc  2460
tggctactac ggtgcaggca ccgttgagta cctcgttggc tccgacggcc tgatctcctt  2520
cctcgaggtc aacacccgcc tccaggtgga acacccagtc accgaagaga ccaccggcat  2580
cgacctggtc cgcgaaatgt tccgcatcgc agaaggccac gagctctcca tcaaggaaga  2640
tccagctcca cgcggccacg cattcgagtt ccgcatcaac ggcgaagacg ctggctccaa  2700
cttcatgcct gcaccaggca agatcaccag ctaccgcgag ccacagggcc caggcgtccg  2760
catggactcc ggtgtcgttg aaggttccga aatctccgga cagttcgact ccatgctggc  2820
aaagctgatc gtttggggcg acacccgcga gcaggctctc cagcgctccc gccgtgcact  2880
tgcagagtac gttgtcgagg gcatgccaac cgttatccca ttccaccagc acatcgtgga  2940
aaacccagca ttcgtgggca cgacgaagg cttcgagatc tacaccaagt ggatcgaaga  3000
ggtttgggat aacccaatcg caccttacgt tgacgcttcc gagctcgacg aagatgagga  3060
caagacccca gcacagaagg ttgttgtgga gatcaaccgc cgtcgcgttg aggttgcact  3120
cccaggcgat ctgcactccg gtggcaccgc tggtcctaag aagaaggcca agaagcgtcg  3180
cgcaggtggt gcaaaggctg gcgtatccgg cgatgcagtg gcagctccaa tgcagggcac  3240
tgtcatcaag gtcaacgtcg aagaaggcgc tgaagtcaac gaaggcgaca ccgttgttgt  3300
cctcgaagct atgaagatgg aaaaccctgt gaaggctcat aagtccggaa ccgtaaccgg  3360
ccttactgtc gctgcaggcg agggtgtcaa caagggcgtt gttctcctcg agatcaagta  3420
atctagagga ggaaaactaa atgaatgttg acattagccg ctctcgtgaa ccgttgaacg  3480
tggaactgtt gaaagaaaaa ctgctgcaga acggtgattt cggtcaagtg atctacgaga  3540
aggtcaccgg ctctaccaat gcggacctgc tggctctgac ggcagcggc gctccaaact  3600
ggaccgtcaa gactgttgaa tttcaggacc acgcccgtgg ccgtctgggt cgtccgtgga  3660
gcgcaccgga gggttcccaa accatcgtca gcgttctggt ccaactgagc attgatcagg  3720
tggaccgtat tggtacgatc ccgctggccg caggcttggc tgttatggat gcgctgaatg  3780
atctgggcgt ggagggtgca ggcctgaaat ggcgaacga tgttcagatc cacggtaaga  3840
agttgtgcgg tattctggtt gaagcaaccg gcttcgactc cactccgacc gtggttatcg  3900
gttggggtac gaatatctcg ttgacgaaag aagagctgcc ggtcccgcac gcgaccagcc  3960
tggccctgga gggtgttgaa gttgaccgta cgacgttcct gattaacatg ctgacccatc  4020
tgcatacccg tctggatcag tggcagggtc cgtctgtgga ctggctggat gactatcgcg  4080
cggtttgtag cagcattggc caagatgttgc ggtcctgct gtgtcctgac aaagagctgc  4140
tgggcgaggc gattgcgtg gcgaccggtg gtgagatccg tgtgcgcgac gccagcggca  4200
cggtccacac gctgaatgcg ggtgaaatca cgcatctgcg tttgcaataa   4250
```

SEQ ID NO: 19      moltype = DNA   length = 5659
FEATURE            Location/Qualifiers
misc_feature       1..5659
                   note = Synthetic polynucleotide
source             1..5659
                   mol_type = other DNA
                   organism = synthetic construct
SEQUENCE: 19
```
atgatcatca aacctaaaat tcgtggattt atctgtacaa caacgcaccc agtgggttgt   60
gaagcgaacg taaaagaaca aattgcctac acaaaagcac aaggtccgat caaaaacgca  120
cctaagcgcg tgttggttgt cggatcgtct agcggctatg tctgtcatc acgcatcgct  180
gcggcgtttg gcggtggtgc ggcgacgatc ggcgtatttt cgaaaagcc gggcactgac  240
```

-continued

```
aaaaaaccag gtactgcggg tttctacaat gcagcagcgt ttgacaagct agcgcatgaa  300
gcgggcttgt acgcaaaaag cctgaacggc gatgcgttct cgaacgaagc gaagcaaaaa  360
gcgattgagc tgattaagca agacctcggc cagattgatt tggtggttta ctcgttggct  420
tctccagtgc gtaagatgcc agacacgggt gagctagtgc gctctgcact aaaaccgatc  480
ggcgaaacgt acacctctac cgcggtagat accaataaag atgtgatcat tgaagccagt  540
gttgaacctg cgaccgagca agaaatcgct gacactgtca ccgtgatggg cggtcaagat  600
tgggaactgt ggatccaagc actggaagag gcgggtgttc ttgctgaagg ttgcaaaacc  660
gtggcgtaca gctacatcgg tactgaattg acttggccaa tttactggga tggcgcttta  720
ggccgtgcca agatggacct agatcgcgca gcgacagcgc tgaacgaaaa gctggcagcg  780
aaaggtggta ccgcgaacgt tgcagttttg aaatcagtgg tgactcaagc aagctctgcg  840
attcctgtga tgccgctcta catcgcaatg gtgttcaaga agatgcgtga acagggcgtg  900
catgaaggct gtatggagca gatctaccgc atgttcagtc aacgtctgta caaagaagat  960
ggttcagcgc cggaagtgga tgatcacaat cgtctgcgtt tggatgactg ggaactgcgt  1020
gatgacattc agcagcactg ccgtgatctg tggccacaaa tcaccacaga gaacctgccg  1080
gagctgaccg attacgacat gtacaaagaa gagttcatca agctgtttgg ctttggcatt  1140
gaaggcattg attacgatgc tgacgtcaat ccagaagtcg aatttgatgt gattgatatc  1200
gagtaattta gtgactgagc gtacatgtat acgaagatta ttggtactgg cagctatctg  1260
cccgaacaag tgcggactaa cgccgatctg gaaaaaatgg ttgagaccac tgacgagtgg  1320
attgtcactc gtacaggtat tcgtaaacgc catatcgccg cgccgaatga aactgtcgcg  1380
acgatgggct ttaccgctgc gaatcgcgcg attgagatgg cggggatcga taaagaccaa  1440
attggcttga ttgtggtggc taccacatca gcaacgcatg catttccaag cgcggcatgt  1500
cagattcaaa gtatgctcgg tattaaaggt tgcccggcgt tatgtgtcgc ggcagcgtgc  1560
gcaggtttca cctacgcgtt aagcatcgcc gaccagtacg ttaaatccgg cgcggttaaa  1620
cacgcgctgg tggtcggttc cgatgtatta gcccgcactt gcgatcctgg cgatcgcggt  1680
acgatcatta tttttcggcga tggcgcaggc gcggccgtac tgagcgcttc tgaagaaccg  1740
ggtattatct ccactcatct tcatgccgat ggccgttacg gtgaattact gaccctgccg  1800
aatgccgatc gcgtaaatcc ggataacccg atttacctga caatggcggg caatgaagtc  1860
tttaaagtgg cggtcactga actgcgcat attgtcgatg agacgctggc ggctaataac  1920
ctggatcgct cagaactcga ttggctggtg ccgcatcagg ctaacctgcg tatcattagc  1980
gcgacagcga aaaaactcgg catgtcgatg gacaatgtgc tcgtcacgct ggacaggcac  2040
ggcaatacct ccgcggcttc tgtgccgtgc gcgctggatg aagccgtgcg tgacgggcga  2100
attaaagccg gtcagctggt attgcttgaa gccttcgggg gtggattcac ctggggctcc  2160
gcgctgattc gtttctagta taaggattta aacatgacgc aatttgcatt tgtgttcccc  2220
ggtcagggtt ctcagagcgt tgggatgttg gccgagatgg cggcaaatta ccctatcgta  2280
gaagaaacgt ttgctgaagc ttctgcggct ctgggatatg atctgtgggc gctcacccag  2340
caaggtccag cggaagaact gaataaaacc tggcagacgc agccggcgtt attaaccgct  2400
tccgtcgcgc tttggcgcgt ttggcagcag cagggcggta aaatgcctgc gttaatggca  2460
ggtcacagcc tgggcgaata ttccgcgctg gtttgcgctg gcgtcatcaa ctttgctgat  2520
gccgttcgtc tggtggaaat gcgcgtaaa ttcatgcagg aagcggttcc ggaaggcact  2580
ggcggcatgt ctgcgatcat cgggctggat gatgcctcta ttgctaaagc ctgtgaagaa  2640
tctgccgaag ggcaggttgt ttcgccggtt aactttaact cgccgggaca ggtggttatc  2700
gccgggcata aagaggcggt agaacgtgcg ggcgcagcct gtaaagccgc tggcgcgaaa  2760
cgcgcgctgc cgctgccggt gagcgtaccg tcgcactgcg ctgatgaa accagcgcag  2820
gataagctgg cggttgaatt agccaaaatt accttagcg cgccaacggt gccggtagtg  2880
aacaacgttg acgtgaaatg tgaaaccgat gccgccgcta tccgcgatgc gctggttcgc  2940
cagttgtaca atccggtaca gtggacgaag agcgtggaat ttatcgcggc gcagggcgtt  3000
gaacatcttt atgaagtggg tccaggtaaa gtcctcactg gtctgacgaa acgtattgtc  3060
gacaccctga cagcgtcggc gctgaacgag ccggcggcgc tgtctgcggc acttacgcaa  3120
taaaagagga aaaccatgag ctttgaagga agattgcgc tggtgactgg tgcaagccgt  3180
ggcataggcc gcgcaattgc agagactctc gttgcccgcg gcgcgaaagt tatcgggact  3240
gcgaccagtg aaaatggtgc gaagaacatt agcgactatt taggtgctaa cgggaaaggt  3300
ttgatgttga atgtgaccga tcctgcatct attgaatctg ttctggaaaa tattcgcgca  3360
gaatttggtg aagtggatat cctggttaat aatgccggta tcactcgtga taatctgttg  3420
atgcgaatga aagatgatga gtggaacgat attatcgaaa ccaacttatc atccgttttc  3480
cgcctgtcaa aagcggtaat gcgcgctatg atgaaaaagc gttgtggtcg cattatcact  3540
attggttctg tggttggtac catgggaaat gcaggtcagg caaactacgc tgcggcgaaa  3600
gcgggcctga tcggtttcag taaatcactg gcgcgtgaag ttgcgtcccg tggtattact  3660
gtcaatgttg tggctccggg tttttattgaa acggacatga cgcgtgcgct gtctgacgat  3720
cagcgtgcg gtatcctggc gcaggtgcct gcgggtcgcc tcggcggcgc tcaggaaatc  3780
gccagtgcgg ttgcattttt agcctctgac gaagcgagtt acatcactgg tgagactctg  3840
cacgtcaacg gcgggaatgta catggtttaa ttttaaggtt tacataaaac atggtagata  3900
aacgcgaatc ctatacaaaa gaagaccttc ttgcctctgg tcgtggtgaa ctgtttggcg  3960
ctaaagggcc gcaactccct gcaccgaaca tgctgatgat ggaccgcgtc gttaagatga  4020
ccgaaacggg cggcaatttc gacaaaggct atgtcgaagc cgagctggat atcaatccgg  4080
atctatggtt cttcggatgc cactttatcg gcgatccggt gatgcccggt tgtctgggtc  4140
tggatgctat gtggcaattg gtgggattct acctgggctg gttgggcggc gaaggcaaag  4200
gccgcgctct gggcgtgggc gaagtgaaat ttaccggcca ggtctgccg acagccagga  4260
aagtcaccta tcgtattcat ttcaaacgta tcgtaaaccg tcgcctgatc atgggcctgg  4320
cggacggtgta ggttctggtg gatggtcgcc tgatctatac cgcacacgat ttgaaagtcg  4380
gtttgttcca ggatacttcc gcgttctaaa aggaggcaac aaaatgaatc gccgcgttgt  4440
cattacgggt attggtgcag tgacgccggt gggtaacaac gctgatagct tctggtgcag  4500
catcaaagag ggtaaatgtg cattgacaa gatcaaagcg tttgacgcaa ccgatttcaa  4560
agttaagctg gctgccgaag tgaaggactt caccccggga gactttatcg acaagcgtga  4620
ggcgaaccgt atggaccgtt ttagccagtt tgcgatcgtt gcggcggatg aggcaatcaa  4680
ggacagcaaa ctggacctgg agtcgattga taagaatcgt ttcggcgtca ttgttggtag  4740
cggcattggc ggcatcggca ccattgagaa gcaggatgaa aagctgatta ccaaaggtcc  4800
gggtcgtgtg agccctatga ctattccgat gatcattgcg aatatggcaa gcggtaatct  4860
ggcgattcgt tatggcgcta aaggtatttg cacgaccatt gtcaccgcat gtgcgagcgc  4920
gaacaacagc attggtgagt ccttccgtaa cattaagttt ggttatagcg acgttatgat  4980
```

```
ctctggtggt agcgaagcag gtatcacccc gttgagcctg gcgggtttttg cctcgatgaa   5040
ggccgtgacc aaatctgagg acccgaagcg cgccagcatc ccgttcgata aggatcgcag   5100
cggtttttgtg atgggcgagg gcagcggtat cgttatcttg gaagagttgg agcacgcgct   5160
gaagcgtggt gccaaaatct atgccgagat cgttggctat ggtgcgacct gcgacgcata   5220
tcatatcacg agcccagcgc cgaatggtga aggtggtgca cgtgcaatga aactggcaat   5280
ggaagaagat aatgtccgcc cagaggacat ttcctatatc aacgcgcacg gtacgagcac   5340
ggcgtacaat gacagcttcg aaacccaagc gatcaagacg gtcctgggtg aatacgccta   5400
caaagtgccg gtgtctagca ccaagagcat gaccggccac ctgctgggcg ctggcggtgc   5460
agtcgaagcg attatctgtg ccaaagctat tgaagagggt ttcattccgc cgaccatcgg   5520
ctacaaagag gcggatccgg aatgcgacct ggattacgtt cctaacgagg gccgtaatgc   5580
agaagtcaac tacgttctgt ccaacagcct gggcttcggt ggccataatg cgactctgct   5640
gttcaaaaag tacaaatga                                                5659
```

```
SEQ ID NO: 20              moltype = DNA   length = 75
FEATURE                    Location/Qualifiers
misc_feature               1..75
                           note = Synthetic oligonucleotide
source                     1..75
                           mol_type = other DNA
                           organism = synthetic construct
SEQUENCE: 20
ttgtccatct ttatataatt tgggggtagg gtgttcttta tgtaaaaaaa acgttttagg   60
atgcatatgg cggcc                                                    75

SEQ ID NO: 21              moltype = DNA   length = 75
FEATURE                    Location/Qualifiers
misc_feature               1..75
                           note = Synthetic oligonucleotide
source                     1..75
                           mol_type = other DNA
                           organism = synthetic construct
SEQUENCE: 21
gataaatcca cgaattttag gtttgatgat cattggtctc ctcctgcagg tgcgtgttcg   60
tcgtcatcgc aattg                                                    75

SEQ ID NO: 22              moltype = DNA   length = 30
FEATURE                    Location/Qualifiers
misc_feature               1..30
                           note = Synthetic oligonucleotide
source                     1..30
                           mol_type = other DNA
                           organism = synthetic construct
SEQUENCE: 22
actcaccgca ttggtgtagt aaggcgcacc                                    30

SEQ ID NO: 23              moltype = DNA   length = 30
FEATURE                    Location/Qualifiers
misc_feature               1..30
                           note = Synthetic oligonucleotide
source                     1..30
                           mol_type = other DNA
                           organism = synthetic construct
SEQUENCE: 23
tgaatgtcat cacgcagttc ccagtcatcc                                    30

SEQ ID NO: 24              moltype = DNA   length = 33
FEATURE                    Location/Qualifiers
misc_feature               1..33
                           note = Synthetic oligonucleotide
source                     1..33
                           mol_type = other DNA
                           organism = synthetic construct
SEQUENCE: 24
ccatcttctt tgtacagacg ttgactgaac atg                                33

SEQ ID NO: 25              moltype = DNA   length = 30
FEATURE                    Location/Qualifiers
misc_feature               1..30
                           note = Synthetic oligonucleotide
source                     1..30
                           mol_type = other DNA
                           organism = synthetic construct
SEQUENCE: 25
gcaccatagc cgtaatccca caggttatag                                    30

SEQ ID NO: 26              moltype = DNA   length = 25
FEATURE                    Location/Qualifiers
misc_feature               1..25
                           note = Synthetic oligonucleotide
```

-continued

```
source                   1..25
                         mol_type = other DNA
                         organism = synthetic construct
SEQUENCE: 26
tgtcattaat ggttaataat gttga                                           25

SEQ ID NO: 27            moltype = DNA  length = 40
FEATURE                  Location/Qualifiers
misc_feature             1..40
                         note = Synthetic oligonucleotide
source                   1..40
                         mol_type = other DNA
                         organism = synthetic construct
SEQUENCE: 27
gcagttattg gtgcccttaa acgcctggtt gctacgcctg                           40

SEQ ID NO: 28            moltype = DNA  length = 27
FEATURE                  Location/Qualifiers
misc_feature             1..27
                         note = Synthetic oligonucleotide
source                   1..27
                         mol_type = other DNA
                         organism = synthetic construct
SEQUENCE: 28
gagccaatat gcgagaacac ccgagaa                                         27

SEQ ID NO: 29            moltype = DNA  length = 48
FEATURE                  Location/Qualifiers
misc_feature             1..48
                         note = Synthetic oligonucleotide
source                   1..48
                         mol_type = other DNA
                         organism = synthetic construct
SEQUENCE: 29
cgctgaacgt attgcaggcc gagttgctgc accgctcccg ccaggcag                  48

SEQ ID NO: 30            moltype = DNA  length = 51
FEATURE                  Location/Qualifiers
misc_feature             1..51
                         note = Synthetic oligonucleotide
source                   1..51
                         mol_type = other DNA
                         organism = synthetic construct
SEQUENCE: 30
ggaattgcca cggtgcggca ggctccatac gcgaggccag gttatccaac g             51

SEQ ID NO: 31            moltype = DNA  length = 35
FEATURE                  Location/Qualifiers
misc_feature             1..35
                         note = Synthetic oligonucleotide
source                   1..35
                         mol_type = other DNA
                         organism = synthetic construct
SEQUENCE: 31
aatcaccagc actaaagtgc gcggttcgtt acccg                                35

SEQ ID NO: 32            moltype = DNA  length = 34
FEATURE                  Location/Qualifiers
misc_feature             1..34
                         note = Synthetic oligonucleotide
source                   1..34
                         mol_type = other DNA
                         organism = synthetic construct
SEQUENCE: 32
atctgccgtg gattgcagag tctattcagc tacg                                 34

SEQ ID NO: 33            moltype = AA  length = 1168
FEATURE                  Location/Qualifiers
source                   1..1168
                         mol_type = protein
                         organism = Mycobacterium smegmatis
SEQUENCE: 33
MTIETREDRF NRRIDHLFET DPQFAAARPD EAISAAAADP ELRLPAAVKQ ILAGYADRPA  60
LGKRAVEFVT DEEGRTTAKL LPRFDTITYR QLAGRIQAVT NAWHNHPVNA GDRVAILGFT  120
SVDYTTIDIA LLELGAVSVP LQTSAPVAQL QPIVAETEPK VIASSVDFLA DAVALVESGP  180
APSRLVVFDY SHEVDDQREA FEAAKGKLAG TGVVVETITD ALDRGRSLAD APLYVPDEAD  240
PLTLLIYTSG STGTPKGAMY PESKTATMWQ AGSKARWDET LGVMPSITLN FMPMSHVMGR  300
GILCSTLASG GTAYFAARSD LSTFLEDLAL VRPTQLNFVP RIWDMLFQEY QSRLDNRRAE  360
GSEDRAEAAV LEEVRTQLLG GRFVSALTGS APISAEMKSW VEDLLDMHLL EGYGSTEAGA  420
```

```
VFIDGQIQRP PVIDYKLVDV PDLGYFATDR PYPRGELLVK SEQMFPGYYK RPEITAEMFD    480
EDGYYRTGDI VAELGPDHLE YLDRRNNVLK LSQGEFVTVS KLEAVFGDSP LVRQIYVYGN    540
SARSYLLAVV VPTEEALSRW DGDELKSRIS DSLQDAARAA GLQSYEIPRD FLVETTPFTL    600
ENGLLTGIRK LARPKLKAHY GERLEQLYTD LAEGQANELR ELRRNGADRP VVETVSRAAV    660
ALLGASVTDL RSDAHFTDLG GDSLSALSFS NLLHEIFDVD VPVGVIVSPA TDLAGVAAYI    720
EGELRGSKRP TYASVHGRDA TEVRARDLAL GKFIDAKTLS AAPGLPRSGT EIRTVLLTGA    780
TGFLGRYLAL EWLERMDLVD GKVICLVRAR SDDEARARLD ATFDTGDATL LEHYRALAAD    840
HLEVIAGDKG EADLGLDHDT WQRLADTVDL IVDPAALVNH VLPYSQMFGP NALGTAELIR    900
IALTTTIKPY VYVSTIGVGQ GISPEAFVED ADIREISATR RVDDSYANGY GNSKWAGEVL    960
LREAHDWCGL PVSVFRCDMI LADTTYSGQL NLPDMFTRLM LSLVATGIAP GSFYELDADG   1020
NRQRAHYDGL PVEFIAEAIS TIGSQVTDGF ETFHVMNPYD DGIGLDEYVD WLIEAGYPVH   1080
RVDDYATWLS RFETALRALP ERQRQASLLP LLHNYQQPSP PVCGAMAPTD RFRAAVQDAK   1140
IGPDKDIPHV TADVIVKYIS NLQMLGLL                                     1168

SEQ ID NO: 34               moltype = AA   length = 1168
FEATURE                     Location/Qualifiers
source                      1..1168
                            mol_type = protein
                            organism = Mycobacterium tuberculosis
SEQUENCE: 34
MSINDQRLTR RVEDLYASDA QFAAASPNEA ITQAIDQPGV ALPQLIRMVM EGYADRPALG     60
QRALRFVTDP DSGRTMVELL PRFETITYRE LWARAGTLAT ALSAEPAIRP GDRVCVLGFN    120
SVDYTTIDIA LIRLGAVSVP LQTSAPVTGL RPIVTETEPT MIATSIDNLG DAVEVLAGHA    180
PARLVVFDYH GKVDTHREAV EAARARLAGS VTIDTLAELI ERGRALPATP IADSADDALA    240
LLIYTSGSTG APKGAMYRES QVMSFWRKSS GWFEPSGYPS ITLNFMPMSH VGGRQVLYGT    300
LSNGGTAYFV AKSDLSTLFE DLALVRPTEL CFVPRIWDMV FAEFHSEVDR RLVDGADRAA    360
LEAQVKAELR ENVLGGRFVM ALTGSAPISA EMTAWVESLL ADVHLVEGYG STEAGMVLND    420
GMVRRPAVID YKLVDVPELG YFGTDQPYPR GELLVKTQTM FPGYYQRPDV TAEVFDPDGF    480
YRTGDIMAKV GPDQFVYLDR RNNVLKLSQG EFIAVSKLEA VFGDSPLVRQ IFIYGNSARA    540
YPLAVVVPSG DALSRHGIEN LKPVISESLQ EVARAAGLQS YEIPRDFIIE TTPFTLENGL    600
LTGIRKLARP QLKKFYGERL ERLYTELADS QSNELRELRQ SGPDAPVLPT LCRAAAALLG    660
STAADVRPDA HFADLGGDSL SALSLANLLH EIFGVDVPVG VIVSPASDLR ALADHIEAAR    720
TGVRRPSFAS IHGRSATEVH ASDLTLDKFI DAATLAAAPN LPAPSAQVRT VLLTGATGFL    780
GRYLALEWLD RMDLVNGKLI CLVRARSDEE AQARLDATVD SPDYLVRHY RELGAGRLEV    840
LAGDKGEADL GLDRVTWQRL ADTVDLIVDP AALVNHVLPY SQLFGPNAAG TAELLRLALT    900
GKRKPYIYTS TIAVGEQIPP EAFTEDADIR AISPTRRIDD SYANGYANSK WAGEVLLREA    960
HEQCGLPVTV FRCDMILADT SYTGQLNLPD MFTRLMLSLA ATGIAPGSFY ELDAHGNRQR   1020
AHYDGLPVEF VAEAICTLGT HSPDRFVTYH VMNPYDDGIG LDEFVDWLNS PTSGSGCTIQ   1080
RIADYGEWLQ RFETSLRALP DRQRHASLLP LLHNYREPAK PICGSIAPTD QFRAAVQEAK   1140
IGPDKDIPHL TAAIIAKYIS NLRLLGLL                                     1168

SEQ ID NO: 35               moltype = DNA   length = 696
FEATURE                     Location/Qualifiers
source                      1..696
                            mol_type = unassigned DNA
                            organism = Synechococcus elongatus
SEQUENCE: 35
atgccgcagc ttgaagccag ccttgaactg gactttcaaa gcgagtccta caaagacgct     60
tacagccgca tcaacgcgat cgtgattgaa ggcgaacaag aggcgttcga caactacaat    120
cgccttgctg agatgctgcc cgaccagcgg gatgagcttc acaagctagc caagatggaa    180
cagcgccaca tgaaaggctt tatggcctgt ggcaaaaatc tctccgtcac tcctgacacg    240
ggttttgccc agaaattttt cgagcgcttg cacgagaact tcaaagcggc ggctgcggaa    300
ggcaaggtcg tcacctgcct actgattcaa tcgctaatca tcgagtgctt tgcgatcgcg    360
gcttacaaca tctacatccc agtggcggat gcttttgccc gcaaaatcac ggaggggtc     420
gtgcgcgacg aatacctgca ccgcaacttc ggtgaagagt ggctgaaggc gaattttgat    480
gcttccaaag ccgaactgga agaagccaat cgtcagaacc tgcccttggt tggctaatg     540
ctcaacgaag tggccgatga tgctcgcgaa ctcgggatgg agcgtgagtc gctcgtcgag    600
gactttatga ttgcctacgg tgaagctctg aaaacatcg gcttcacaac gcgcgaaatc     660
atgcgtatgt ccgcctatgg ccttgcggcc gtttga                             696

SEQ ID NO: 36               moltype = AA   length = 231
FEATURE                     Location/Qualifiers
source                      1..231
                            mol_type = protein
                            organism = Synechococcus elongatus
SEQUENCE: 36
MPQLEASLEL DFQSESYKDA YSRINAIVIE GEQEAFDNYN RLAEMLPDQR DELHKLAKME     60
QRHMKGFMAC GKNLSVTPDM GFAQKFFERL HENFKAAAAE GKVVTCLLIQ SLIIECFAIA    120
AYNIYIPVAD AFARKITEGV VRDEYLHRNF GEEWLKANFD ASKAELEEAN RQNLPLVWLM    180
LNEVADDARE LGMERESLVE DFMIAYGEAL ENIGFTTREI MRMSAYGLAA V            231

SEQ ID NO: 37               moltype = DNA   length = 1029
FEATURE                     Location/Qualifiers
source                      1..1029
                            mol_type = unassigned DNA
                            organism = Synechococcus elongatus
SEQUENCE: 37
atggcattcg gtcttatcgg tcatctcacc agtttggagc aggcccgcga cgtttctcgc     60
aggatgggct acgacgaata cgccgatcaa ggattggagt tttggagtag cgctcctcct    120
```

```
caaatcgttg atgaaatcac agtcaccagt gccacaggca aggtgattca cggtcgctac   180
atcgaatcgt gtttcttgcc ggaaatgctg gcggcgcgcc gcttcaaaac agccacgcgc   240
aaagttctca atgccatgtc ccatgcccaa aaacacggca tcgacatctc ggccttgggg   300
ggctttacct cgattatttt cgagaatttc gatttggcca gtttgcggca agtgcgcgac   360
actaccttgg agtttgaacg gttcaccacc ggcaatactc acacggccta cgtaatctgt   420
agacaggtgg aagccgctgc taaaacgctg ggcatcgaca ttacccaagc gacagtagcg   480
gttgtcggcg cgactggcga tatcggtagc gctgtctgcc gctggctcga cctcaaactg   540
ggtgtcggtg atttgatcct gacggcgcgc aatcaggagc gtttggataa cctgcaggct   600
gaactcggcc ggggcaagat tctgcccttg gaagccgctc tgccggaagc tgactttatc   660
gtgtgggtcg ccagtatgcc tcagggcgta gtgatcgacc cagcaaccct gaagcaaccc   720
tgcgtcctaa tcgacggggg ctaccccaaa aacttgggca gcaaagtcca aggtgagggc   780
atctatgtcc tcaatggcgg ggtagttgaa cattgcttcg acatcgactg gcagatcatg   840
tccgctgcag agatggcgcg gcccgagcgc cagatgtttg cctgctttgc cgaggcgatg   900
ctcttggaat ttgaaggctg gcatactaac ttctcctggg gccgcaacca aatcacgatc   960
gagaagatgg aagcgatcgg tgaggcatcg gtgcgccacg gcttccaacc cttggcattg  1020
gcaatttga                                                         1029

SEQ ID NO: 38          moltype = AA  length = 342
FEATURE                Location/Qualifiers
source                 1..342
                       mol_type = protein
                       organism = Synechococcus elongatus
SEQUENCE: 38
MAFGLIGHLT SLEQARDVSR RMGYDEYADQ GLEFWSSAPP QIVDEITVTS ATGKVIHGRY    60
IESCFLPEML AARRFKTATR KVLNAMSHAQ KHGIDISALG GFTSIIFENF DLASLRQVRD   120
TTLEFERFTT GNTHTAYVIC RQVEAAAKTL GIDITQATVA VVGATGDIGS AVCRWLDLKL   180
GVGDLILTAR NQERLDNLQA ELGRGKILPL EAALPEADFI VWVASMPQGV VIDPATLKQP   240
CVLIDGGYPK NLGSKVQGEG IYVLNGGVVE HCFDIDWQIM SAAEMARPER QMFACFAEAM   300
LLEFEGWHTN FSWGRNQITI EKMEAIGEAS VRHGFQPLAL AI                      342

SEQ ID NO: 39          moltype = DNA  length = 717
FEATURE                Location/Qualifiers
source                 1..717
                       mol_type = unassigned DNA
                       organism = Prochlorococcus mariunus
SEQUENCE: 39
atgcaaacac tcgaatctaa taaaaaaact aatctagaaa attctattga tttacccgat    60
tttactactg attcttacaa agacgcttat agcaggataa atgcaatagt tattgaaggt   120
gaacaagagg ctcatgataa ttacatttcc ttagcaacat taattcctaa cgaattagaa   180
gagttaacta aattagcgaa aatggagctt aagcacaaaa gaggctttac tgcatgtgga   240
agaaatctag gtgttcaagc tgacatgatt tttgctaaag aattcttttc caaattacat   300
ggtaattttc aggttgcgtt atctaatggc aagacaacta catgcctatt aatacaggca   360
attttaattg aagcttttgc tatatccgcg tatcacgttt acatagagt tgctgatcct   420
ttcgcgaaaa aaattaccca aggtgttgtt aaagatgaat atcttcattt aaattatgga   480
caagaatggc taaaagaaaa tttagcgact tgtaaagatg agctaatgga agcaaataag   540
gttaaccttg cattaatcaa gaagatgtta gatcaagtct cggaagatgc ttcagtacta   600
gctatggata gggaagaatt aatggaagaa ttcatgattg cctatcagga cactctcctt   660
gaaataggtt tagataatag agaaattgca agaatggcaa tggctgctat agtttaa      717

SEQ ID NO: 40          moltype = AA  length = 238
FEATURE                Location/Qualifiers
source                 1..238
                       mol_type = protein
                       organism = Prochlorococcus mariunus
SEQUENCE: 40
MQTLESNKKT NLENSIDLPD FTTDSYKDAY SRINAIVIEG EQEAHDNYIS LATLIPNELE    60
ELTKLAKMEL KHKRGFTACG RNLGVQADMI FAKEFFSKLH GNFQVALSNG KTTTCLLIQA   120
ILIEAFAISA YHVYIRVADP FAKKITQGVV KDEYLHLNYG QEWLKENLAT CKDELMEANK   180
VNLPLIKKML DQVSEDASVL AMDREELMEE FMIAYQDTLL EIGLDNREIA RMAMAAIV     238

SEQ ID NO: 41          moltype = DNA  length = 1044
FEATURE                Location/Qualifiers
source                 1..1044
                       mol_type = unassigned DNA
                       organism = Prochlorococcus mariunus
SEQUENCE: 41
atggcatttg ggcttatagg tcattcaact agttttgaag atgcaaaaag aaaggcttca    60
ttattgggct ttgatcatat tgcggatggt gatttagatg tttggtgcac agctccacct   120
caactagttg aaaatgtaga ggttaaaagt gctataggta tatcaattga aggttcttat   180
attgattcat gtttcgttcc tgaaatgctt tcaagattta aaacggcaag aagaaaagta   240
ttaaatgcaa tggaattagc tcaaaaaaaa ggtattaata ttaccgcttt gggggggttc   300
acttctatca tctttgaaaa ttttaatctc cttcaacata agcagattag aaacacttca   360
ctagagtggg aaaggtttac aactggtaat actcatactg cgtgggttat ttgcaggcaa   420
ttagaagatga atgctcctaa aataggtatt gatcttaaaa gcgcaacagt tgctgtagtt   480
ggtgctactg agatatatagg cagtgctgtt tgtcgatggt taatcaataa aacaggtatt   540
ggggaacttc ttttggtagc taggcaaaag gaacccttgg attctttgca aaaggaatta   600
gatggtggaa ctatcaaaaa tctagatgaa gcattgcctg aagcagatat tgttgtatgg   660
gtagcaagta tgccaaagac aatggaaatc gatgctaata atcttaaaca accatgttta   720
atgattgatg gaggttatcc aaagaatcta gatgaaaaat ttcaaggaaa taatatacat   780
```

-continued

```
gttgtaaaag gaggtatagt aagattcttc aatgatatag gttggaatat gatggaacta   840
gctgaaatgc aaaatcccca gagagaaatg tttgcatgct ttgcagaagc aatgatttta   900
gaatttgaaa aatgtcatac aaactttagc tggggaagaa ataatatatc tctcgagaaa   960
atggagttta ttggagctgc ttctgtaaag catggcttct ctgcaattgg cctagataag  1020
catccaaaag tactagcagt ttga                                         1044

SEQ ID NO: 42            moltype = AA   length = 347
FEATURE                  Location/Qualifiers
source                   1..347
                         mol_type = protein
                         organism = Prochlorococcus mariunus
SEQUENCE: 42
MAFGLIGHST SFEDAKRKAS LLGFDHIADG DLDVWCTAPP QLVENVEVKS AIGISIEGSY    60
IDSCFVPEML SRFKTARRKV LNAMELAQKK GINITALGGF TSIIFENFNL LQHKQIRNTS   120
LEWERFTTGN THTAWVICRQ LEMNAPKIGI DLKSATVAVV GATGDIGSAV CRWLINKTGI   180
GELLLVARQK EPLDSLQKEL DGGTIKNLDE ALPEADIVVW VASMPKTMEI DANNLKQPCL   240
MIDGGYPKNL DEKFQGNNIH VVKKGGIVRFF NDIGWNMMEL AEMQNPQREM FACFAEAMIL   300
EFEKCHTNFS WGRNNISLEK MEFIGAASVK HGFSAIGLDK HPKVLAV                 347

SEQ ID NO: 43            moltype = DNA   length = 255
FEATURE                  Location/Qualifiers
source                   1..255
                         mol_type = unassigned DNA
                         organism = Nostoc punctiforme
SEQUENCE: 43
atgagccaaa cggaactttt tgaaaaggtc aagaaaatcg tcatcgaaca actgagtgtt    60
gaagatgctt ccaaaatcac tccacaagct aagtttatgg aagatttagg agctgattcc   120
ctggatactg ttgaactcgt gatggctttg gaagaagaat ttgatatcga aattcccgac   180
gaagctgccg agcagattgt atcggttcaa gacgcagtag attacatcaa taacaaagtt   240
gctgcatcag cttaa                                                    255

SEQ ID NO: 44            moltype = AA   length = 84
FEATURE                  Location/Qualifiers
source                   1..84
                         mol_type = protein
                         organism = Nostoc punctiforme
SEQUENCE: 44
MSQTELFEKV KKIVIEQLSV EDASKITPQA KFMEDLGADS LDTVELVMAL EEEFDIEIPD    60
EAAEQIVSVQ DAVDYINNKV AASA                                          84

SEQ ID NO: 45            moltype = DNA   length = 234
FEATURE                  Location/Qualifiers
source                   1..234
                         mol_type = unassigned DNA
                         organism = Synechocystis sp.
SEQUENCE: 45
atgaatcagg aaatttttga aaaagtaaaa aaaatcgtcg tggaacagtt ggaagtggat    60
cctgacaaag tgacccccga tgccacctt gccgaagatt taggggctga ttccctcgat    120
acagtggaat tggtcatggc cctggaagaa gagtttgata ttgaaattcc cgatgaagtg   180
gcggaaacca ttgataccgt gggcaaagcc gttgagcata tcgaaagtaa ataa          234

SEQ ID NO: 46            moltype = AA   length = 77
FEATURE                  Location/Qualifiers
source                   1..77
                         mol_type = protein
                         organism = Synechocystis sp.
SEQUENCE: 46
MNQEIFEKVK KIVVEQLEVD PDKVTPDATF AEDLGADSLD TVELVMALEE EFDIEIPDEV    60
AETIDTVGKA VEHIESK                                                  77

SEQ ID NO: 47            moltype = DNA   length = 243
FEATURE                  Location/Qualifiers
source                   1..243
                         mol_type = unassigned DNA
                         organism = Prochlorococcus marinus
SEQUENCE: 47
atgtcacaag aagaaatcct tcaaaaagta tgctctattg tttctgagca actaagtgtt    60
gaatcagccg aagtaaaatc tgattcaaac tttcaaaatg atttaggtgc agactcccta   120
gacaccgtag agctagttat ggctcttgaa gaagcatttg atatcgagat acctgatgaa   180
gcagctgaag gtatcgcaac agtaggagat gctgttaaat tcatcgaaga aaaaaaaggt   240
taa                                                               243

SEQ ID NO: 48            moltype = AA   length = 80
FEATURE                  Location/Qualifiers
source                   1..80
                         mol_type = protein
                         organism = Prochlorococcus marinus
SEQUENCE: 48
MSQEEILQKV CSIVSEQLSV ESAEVKSDSN FQNDLGADSL DTVELVMALE EAFDIEIPDE    60
```

```
AAEGIATVGD AVKFIEEKKG                                                    80

SEQ ID NO: 49              moltype = DNA   length = 243
FEATURE                    Location/Qualifiers
source                     1..243
                           mol_type = unassigned DNA
                           organism = Synechococcus elongatus
SEQUENCE: 49
atgagccaag aagacatctt cagcaaagtc aaagacattg tggctgagca gctgagtgtg   60
gatgtggctg aagtcaagcc agaatccagc ttccaaaacg atctgggagc ggactcgctg   120
gacaccgtgg aactggtgat ggctctggaa gaggctttcg atatcgaaat ccccgatgaa   180
gccgctgaag gcattgcgac cgttcaagac gccgtcgatt tcatcgctag caaagctgcc   240
tag                                                                  243

SEQ ID NO: 50              moltype = AA   length = 80
FEATURE                    Location/Qualifiers
source                     1..80
                           mol_type = protein
                           organism = Synechococcus elongatus
SEQUENCE: 50
MSQEDIFSKV KDIVAEQLSV DVAEVKPESS FQNDLGADSL DTVELVMALE EAFDIEIPDE   60
AAEGIATVQD AVDFIASKAA                                                80

SEQ ID NO: 51              moltype = DNA   length = 255
FEATURE                    Location/Qualifiers
source                     1..255
                           mol_type = unassigned DNA
                           organism = Nostoc sp.
SEQUENCE: 51
atgagccaat cagaaacttt tgaaaaagtc aaaaaaattg ttatcgaaca actaagtgtg   60
gagaaccctg acacagtaac tccagaagct agttttgcca acgatttaca ggctgattcc   120
ctcgatacag tagaactagt aatggctttg gaagaagaat ttgatatcga aattcccgat   180
gaagccgcag agaaaattac cactgttcaa gaagcggtgg attacatcaa taaccaagtt   240
gccgcatcag cttaa                                                    255

SEQ ID NO: 52              moltype = AA   length = 84
FEATURE                    Location/Qualifiers
source                     1..84
                           mol_type = protein
                           organism = Nostoc sp.
SEQUENCE: 52
MSQSETFEKV KKIVIEQLSV ENPDTVTPEA SFANDLQADS LDTVELVMAL EEEFDIEIPD   60
EAAEKITTVQ EAVDYINNQV AASA                                           84

SEQ ID NO: 53              moltype = DNA   length = 675
FEATURE                    Location/Qualifiers
source                     1..675
                           mol_type = unassigned DNA
                           organism = Bacillus subtilis
SEQUENCE: 53
atgaagattt acggaattta tatggaccgc ccgctttcac aggaagaaaa tgaacggttc   60
atgactttca tatccacctga aaaacgggag aaatgccgga gatttttatca taaagaagat   120
gctcaccgca ccctgctggg agatgtgctc gttcgctcag tcataagcag gcagtatcag   180
ttggacaaat ccgatatccg ctttagcacg caggaatacg ggaagccgtg catccctgat   240
cttcccgacg ctcatttcaa catttctcac tccggccgct gggtcattgg tgcgtttgat   300
tcacagccga tcggcataga tatcgaaaaa acgaaaccga tcagccttga gatcgccaag   360
cgcttctttt caaaaacaga gtacagcgac ctttttagcaa aagacaagga cgagcagaca   420
gactatttt atcatctatg gtcaatgaaa gaaagcttta tcaaacagga aggcaaaggc   480
ttatcgcttc cgcttgattc cttttcagtg cgcctgcatc aggacggaca agtatccatt   540
gagcttccgg acagccattc cccatgctat atcaaaacgt atgaggtcga tcccggctac   600
aaaatggctg tatgcgccgc acaccctgat ttccccgagg atatcacaat ggtctcgtac   660
gaagagcttt ataa                                                     675

SEQ ID NO: 54              moltype = AA   length = 224
FEATURE                    Location/Qualifiers
source                     1..224
                           mol_type = protein
                           organism = Bacillus subtilis
SEQUENCE: 54
MKIYGIYMDR PLSQEENERF MTFISPEKRE KCRRFYHKED AHRTLLGDVL VRSVISRQYQ   60
LDKSDIRFST QEYGKPCIPD LPDAHFNISH SGRWVIGAFD SQPIGIDIEK TKPISLEIAK   120
RFFSKTEYSD LLAKDKDEQT DYFYHLWSMK ESFIKQEGKG LSLPLDSFSV RLHQDGQVSI   180
ELPDSHSPCY IKTYEVDPGY KMAVCAAHPD FPEDITMVSY EELL                    224

SEQ ID NO: 55              moltype = DNA   length = 867
FEATURE                    Location/Qualifiers
source                     1..867
                           mol_type = unassigned DNA
                           organism = Corynebacterium glutamicum
```

```
SEQUENCE: 55
ttgggcgtgt cgcccttaaa gcgcgctttt cgacgcgacc ccactacatt ggcttccatg    60
aacgttgaca tttcacgatc cagagagccg ctaaacgttg agctcctgaa ggaaaaattg   120
ctccaaaacg gtgactttgg ccaggtcatt tacgaaaaag tgacaggctc cactaatgct   180
gacttgctgg cacttgcagg ttctggcgct ccaaactgca cggtgaaaac tgtcgagttt   240
caagatcatg cgccgtgggcg actcggccgc ccgtggtctg ccccctgaggg ttcccaaaca   300
atcgtgtctg tgctcgttca actatctatt gatcaagtgg accggattgg cactattcca   360
ctcgcggcgg gactcgctgt catggatgcg ttgaatgacc tcggtgtgga aggtgccgga   420
ctgaaatggc ccaacgatgt tcaaatccac ggcaagaaac tctgcggcat cctggtggaa   480
gccaccggct ttgattccac cccaacagtt gtcatcggtt ggggcactaa tatcagcctg   540
actaaagagg agcttcctgt tcctcatgca acttccctcg cattggaagg tgttgaagtc   600
gacagaacca cattccttat taatatgctc acacatctgc atactcgact ggaccagtgg   660
cagggtccaa gtgtggattg gctcgatgat taccgtgcgg tatgttccag tattggccaa   720
gatgttgag tgcttctacc tggggataaa gaactcttag gtgaagcgat cggtgtcgcg   780
actggcggag aaattcgtgt tcgcgatgct tcgggcaccg ttcacaccct caacgccggt   840
gaaattacgc accttcgcct gcagtaa                                       867

SEQ ID NO: 56          moltype = DNA  length = 810
FEATURE                Location/Qualifiers
source                 1..810
                       mol_type = unassigned DNA
                       organism = Corynebacterium glutamicum
SEQUENCE: 56
atgaatgttg acattagccg ctctcgtgaa ccgttgaacg tggaactgtt gaaagaaaaa    60
ctgctgcaga acggtgattt cggtcaagtg atctacgaga aggtcaccgg ctctaccaat   120
gcggacctgc tggctctggc gggcagcggc gctccaaact ggaccgtcaa gactgttgaa   180
tttcaggacc acgcccgtgg ccgtctgggc gtccgtgga gcgcaccgga gggttcccaa   240
accatcgtca cgcgttctggt ccaactgagc attgatcagg tggaccgtat tggtacgatc   300
ccgctggccg caggcttggc tgttatggat gcgctgaatg atctgggcgt ggagggtgca   360
ggcctgaaat ggccgaacga tgttcagatc cacggtaaga agttgtgcgg tattctggtt   420
gaagcaaccg gcttcgactc cactccgacc gtggttatcg gttggggtac gaatatctcg   480
ttgacgaaag aagagctgcc ggtcccgcac gcgaccagcc tggccctgga gggtgttgaa   540
gttgaccgta cgacgttcct gattaacatg ctgacccatc tgcatacccg tctggatcag   600
tggcagggtc cgtctgtgga ctggctggat gactatcgcg cggtttgtag cagcattggc   660
caagatgtgc gtgtcctgct gcctggtgac aaagagctgc tgggcgaggc gattggcgtg   720
gcgaccggtg tgagatccg tgtgcgcgac gccagcggca cggtccacac gctgaatgcg   780
ggtgaaatca cgcatctgcg tttgcaataa                                    810

SEQ ID NO: 57          moltype = AA  length = 269
FEATURE                Location/Qualifiers
source                 1..269
                       mol_type = protein
                       organism = Corynebacterium glutamicum
SEQUENCE: 57
MNVDISRSRE PLNVELLKEK LLQNGDFGQV IYEKVTGSTN ADLLALAGSG APNWTVKTVE    60
FQDHARGRLG RPWSAPEGSQ TIVSVLVQLS IDQVDRIGTI PLAAGLAVMD ALNDLGVEGA   120
GLKWPNDVQI HGKKLCGILV EATGFDSTPT VVIGWGTNIS LTKEELPVPH ATSLALEGVE   180
VDRTTFLINM LTHLHTRLDQ WQGPSVDWLD DYRAVCSSIG QDVRVLLPGD KELLGEAIGV   240
ATGGEIRVRD ASGTVHTLNA GEITHLRLQ                                     269

SEQ ID NO: 58          moltype = DNA  length = 1632
FEATURE                Location/Qualifiers
source                 1..1632
                       mol_type = unassigned DNA
                       organism = Corynebacterium glutamicum
SEQUENCE: 58
atgaccattt cctcaccttt gattgacgtc gccaaccttc cagacatcaa caccactgcc    60
ggcaagatcg ccgaccttaa ggctcgccgc gcggaagccc atttccccat gggtgaaaag   120
gcagtagaga aggtccacgc tgctggacgc ctccatgccc gtgagcgctt ggattactta   180
ctcgatgagg gctccttcat cgagaccgat cagctggctc gccaccgcac caccgctttc   240
ggcctgggcg ctaagcgtcc tgcaaccgac ggcatcgtga ccggctgggg caccattgat   300
ggacgcgaag tctgcatctt ctcgcaggac ggcaccgtat tcggtggcgc gcttggtgag   360
gtgtacggc aaaagatgat caagatcatg gagctggcaa tcgacaccgg ccgcccattg   420
atcggtcttt acgaaggcgc tggcgctcgt attcaggacg gcgctgtctc cctggacttc   480
atttcccaga ccttctacca aaacattcag gcttctggcg ttatcccaca gatctccgtc   540
atcatgggcg catgtgcagg tggcaacgct tacgcgccag ctctgaccga cttcgtggtc   600
atggtggaca gacctccaa gatgttcgtt accggcccag acgtgatcaa gaccgtcacc   660
ggcgaggaa tcacccagga gagcttggc ggagcaacca cccacatggt gaccgctggt   720
aactcccact acaccgctgc gaccgatgag gaagcactgg attgggtaca ggacctggtg   780
tccttcctcc catccaacaa tcgctcctac gcaccgatgg aagacttcga cgaggaagaa   840
ggcggcgttg aagaaaacat caccgctgac gatctgaagc tcgacgagat catcccagat   900
tccgcgaccg ttccttacga cgtccgcgat gtcatcgaat gcctcaccga cgatggcgaa   960
tacctggaaa tccaggcaga ccgcgcagaa aacgttgtta ttgcattcgg ccgcatcgaa  1020
ggcagtccg ttggcttgt tgccaaccag ccaacccagt cgctcggctg cctggacatc  1080
gactcctctg agaaggcagc tcgcttcgtc cgcacctgcg acgcgttcaa catcccaatc  1140
gtcatgcttg tcgacgtccc cggcttcctc ccaggcgcag gccaggagta cggtggcatt  1200
ctgcgtcgtg gcgcaaagct gctctacgca tacggcgaag caaccgttcc aaagatcacc  1260
gtcaccatgc gtaaggctta cggcggagcg tactgcgtga tgggttccaa gggcttgggc  1320
tctgacatca accttgcatg gccaaccgca cagatcgccg tcatgggcgc tgctggcgca  1380
```

```
gttggattca tctaccgcaa ggagctcatg gcagctgatg ccaagggcct cgataccgta   1440
gctctggcta agtccttcga gcgcgagtat gaagaccaca tgctcaaccc gtaccacgct   1500
gcagaacgtg gcctgatcga cgccgtgatc ctgccaagcg aaacccgcgg acagatttcc   1560
cgcaaccttc gcctgctcaa gcacaagaac gtcactcgcc ctgctcgcaa gcacggcaac   1620
atgccactgt aa                                                      1632

SEQ ID NO: 59           moltype = AA  length = 543
FEATURE                 Location/Qualifiers
source                  1..543
                        mol_type = protein
                        organism = Corynebacterium glutamicum
SEQUENCE: 59
MTISSPLIDV ANLPDINTTA GKIADLKARR AEAHFPMGEK AVEKVHAAGR LTARERLDYL   60
LDEGSFIETD QLARHRTTAF GLGAKRPATD GIVTGWGTID GREVCIFSQD GTVFGGALGE   120
VYGEKMIKIM ELAIDTGRPL IGLYEGAGAR IQDGAVSLDF ISQTFYQNIQ ASGVIPQISV   180
IMGACAGGNA YGPALTDFVV MVDKTSKMFV TGPDVIKTVT GEEITQEELG GATTHMVTAG   240
NSHYTAATDE EALDWVQDLV SFLPSNNRSY APMEDFDEEE GGVEENITAD DLKLDEIIPD   300
SATVPYDVRD VIECLTDDGE YLEIQADRAE NVVIAFGRIE GQSVGFVANQ PTQFAGCLDI   360
DSSEKAARFV RTCDAFNIPI VMLVDVPGFL PGAGQEYGGI LRRGAKLLYA YGEATVPKIT   420
VTMRKAYGGA YCVMGSKGLG SDINLAWPTA QIAVMGAAGA VGFIYRKELM AADAKGLDTV   480
ALAKSFEREY EDHMLNPYHA AERGLIDAVI LPSETRGQIS RNLRLLKHKN VTRPARKHGN   540
MPL                                                                543

SEQ ID NO: 60           moltype = DNA  length = 1776
FEATURE                 Location/Qualifiers
source                  1..1776
                        mol_type = unassigned DNA
                        organism = Corynebacterium glutamicum
SEQUENCE: 60
atgtcagtcg agactcgcaa gatcaccaag gttcttgtcg ctaaccgtgg tgagattgca   60
atccgcgtgt tccgtgcagc tcgagatgaa ggcatcggat ctgtcgccgt ctacgcagag   120
ccagatgcag atgcaccatt cgtgtcatat gcagacgagg cttttgccct cggtggccaa   180
acatccgctg agtcctacct tgtcattgac aagatcatcg atgcggcccg caagtccggc   240
gccgacgcca tccacccgg ctacggcttc ctcgcagaaa acgtcgactt cgcagaagca   300
gtcatcaacg aaggcctgat ctggattgga ccttcacctg agtccatccg ctccctcggc   360
gacaaggtca ccgctcgcca catcgcagat accgccaagg ctccaatggc tcctggcacc   420
aaggaaccag taaagacgc agcagaagtt gtggctttcg ctgaagaatt cggtctccca   480
atcgccatca aggcagcttt cggtggcggc ggacgtggca tgaaggttgc ctacaagatg   540
gaagaagtcg ctgacctctt cgagtccgca acccgtgaag caaccgcagc gttcggccgc   600
ggcgagtgct tcgtggagcg ctacctggac aaggcacgcc acgttgaggc tcaggtcatc   660
gccgataagc acggcaacgt tgttgtcgcc ggaaccgtg actgctccct gcagcgccgt   720
ttccagaagc tcgtcgaaga agcaccagca ccattcctca ccgatgacca gcgcgagcgt   780
ctccactcct ccgcgaaggc tatctgtaag gaagctggat actacggtgc aggcaccgtt   840
gagtacctcg ttggctccga cggcctgatc tccttcctcg aggtcaacac ccgcctccag   900
gtggaacacc cagtcaccga agagaccacc ggcatcgacc tggtccgcga aatgttccgc   960
atcgcagaag gccacgagct ctccatcaag gaagatccag ctccacgcgg ccacgcattc   1020
gagttccgca gagttcgaa gacgctggc tccaacttca tgcctgcacc aggcaagatc   1080
accagctacc gcgagccaca gggcccaggc gtccgcatgg actccggtgt cgttgaaggt   1140
tccgaaatct ccggacagtt cgactccatg ctggcaaagc tgatcgtttg gggcgacacc   1200
cgcgagcagg ctctccagcg ctcccgccgt gcacttgcag agtacgttgt cgagggcatg   1260
ccaaccgtta tcccattcca ccagcacatc gtggaaaacc cagcattcgt gggcaacgac   1320
gaaggcttcg agatctacac caagtggatc gaagaggttt gggataaccc aatcgcacct   1380
tacgttgacg cttccgagct cgacgaagat gaggacaaga ccccagcaca gaaggttgtt   1440
gtggagatca acggccgtcg cgttgaggtt gcactcccag gcgatctggc actcggtggc   1500
accgctggtc ctaagaagaa ggccaagaag cgtcgcggag gtgctgcaaa ggctggcgta   1560
tccggcgatg cagtggcagc tccaatgcag ggcactgtca tcaaggtcaa cgtcgaagaa   1620
ggcgctgaag tcaacgaagg cgacaccgtt gttgtcctcg aggctatgaa gatggaaaac   1680
cctgtgaagg ctcataagtc cggaaccgta accggcctta ctgtcgctgc aggcgagggt   1740
gtcaacaagg gcgttgttct cctcgagatc aagtaa                            1776

SEQ ID NO: 61           moltype = AA  length = 591
FEATURE                 Location/Qualifiers
source                  1..591
                        mol_type = protein
                        organism = Corynebacterium glutamicum
SEQUENCE: 61
MSVETRKITK VLVANRGEIA IRVFRAARDE GIGSVAVYAE PDADAPFVSY ADEAFALGGQ   60
TSAESYLVID KIIDAARKSG ADAIHPGYGF LAENADFAAV VINEGLIWIG PSPESIRSLG   120
DKVTARHIAD TAKAPMAPGT KEPVKDAAEV VAFAEEFGLP IAIKAAFGGG GRGMKVAYKM   180
EEVADLFESA TREATAAFGR GECFVERYLD KARHVEAQVI ADKHGNVVVA GTRDCSLQRR   240
FQKLVEEAPA PFLTDDQRER LHSSAKAICK EAGYYGAGTV EYLVGSDGLI SFLEVNTRLQ   300
VEHPVTEETT GIDLVREMFR IAEGHELSIK EDPAPRGHAF EFRINGEDAG SNFMPAPGKI   360
TSYREPQGPG VRMDSGVVEG SEISGQFDSM LAKLIVWGDT REQALQRSRR ALAEYVVEGM   420
PTVIPFHQHI VENPAFVGND EGFEIYTKWI EEVWDNPIAP YVDASELDED EDKTPAQKVV   480
VEINGRRVEV ALPGDLALGG TAGPKKKAKK RRAGGAKAGV SGDAVAAPMQ GTVIKVNVEE   540
GAEVNEGDTV VVLEAMKMEN PVKAHKSGTV TGLTVAAGEG VNKGVVLLEI K            591

SEQ ID NO: 62           moltype = DNA  length = 10025
FEATURE                 Location/Qualifiers
```

-continued

```
misc_feature          1..10025
                      note = Synthetic polynucleotide
source                1..10025
                      mol_type = other DNA
                      organism = synthetic construct
SEQUENCE: 62
cactatacca attgagatgg gctagtcaat gataattact agtccttttc ctttgagttg    60
tgggtatctg taaattctgc tagacctttg ctggaaaact tgtaaattct gctagaccct   120
ctgtaaattc cgctagacct ttgtgtgttt tttttgttta tattcaagtg gttataattt   180
atagaataaa gaaagaataa aaaaagataa aaagaataga tcccagccct gtgtataact   240
cactacttta gtcagttccg cagtattaca aaaggatgtc gcaaacgctg tttgctcctc   300
tacaaaacag accttaaaac cctaaaggcg tcggcatccg cttacagaca agctgtgacc   360
gtctccggga gctgcatgtg tcagaggttt tcaccgtcat caccgaaacg cgcgaggcag   420
cagatcaatt cgcgcgcgaa ggcgaagcgg catgcattta cgttgacacc atcgaatggt   480
gcaaaacctt tcgcggtatg gcatgatagc gcccggaaga gagtcaattc agggtggtga   540
atgtgaaacc agtaacgtta tacgatgtcg cagagtatgc cggtgtctct tatcagaccg   600
tttcccgcgt ggtgaaccag gccagccacg tttctgcgaa aacgcgggaa aaagtggaag   660
cggcgatggc ggagctgaat tacattccca accgcgtggc acaacaactg gcgggcaaac   720
agtcgttgct gattggcgtt gccacctcca gtctggccct gcacgcgccg tcgcaaattg   780
tcgcggcgat taaatctcgc gccgatcaac tgggtgccag cgtggtggtg tcgatggtag   840
aacgaagcgg cgtcgaagcc tgtaaagcgg cggtgcacaa tcttctcgcg caacgcgtca   900
gtgggctgat cattaactat ccgctggatg accaggatgc cattgctgtg gaagctgcct   960
gcactaatgt tccggcgtta tttcttgatg tctctgacca gacacccatc aacagtatta  1020
ttttctccca tgaagacggt acgcgactgg gcgtggagca tctggtcgca ttgggtcacc  1080
agcaaatcgc gctgttagcg ggcccattaa gttctgtctc ggcgcgtctg cgtctggctg  1140
gctggcataa atatctcact cgcaatcaaa ttcagccgat agcggaacgg gaaggcgact  1200
ggagtgccat gtccggtttt caacaaacca tgcaaatgct gaatgagggc atcgttccca  1260
ctgcgatgct ggttgccaac gatcagatgg cgctgggcgc aatgcgcgcc attaccgagt  1320
ccgggctgcg cgttggtgcg gatatctcgg tagtgggata cgacgatacc gaagacagct  1380
catgttatat cccgccgtta accaccatca aacaggattt tcgcctgctg gggcaaacca  1440
gcgtggaccg cttgctgcaa ctctctcagg gccaggcggt gaagggcaat cagctgttgc  1500
ccgtctcact ggtgaaaaga aaaaccaccc tggcgcccaa tacgcaaacc gcctctcccc  1560
gcgcgttggc cgattcatta atgcagctgg cacgacaggt ttcccgactg gaaagcgggc  1620
agtgagcgca acgcaattaa tgtaagttag cgcgaattga tctggtttga cagcttatca  1680
tcgactgcac ggtgcaccaa tgcttctggc gtcaggcagc catcggaagc tgtggtatgg  1740
ctgtgcaggt cgtaaatcac tgcataattc gtgtcgctca aggcgcactc ccgttctgga  1800
taatgttttt tgcgccgaca tcataacggt tctggcaaat attctgttga caattaatca  1860
tccggctcgt ataaagtgtg gaattgtgag cggataacaa tttcacacag gaaacagcgc  1920
cgctgagaaa aagcgaagcg gcactgctct ttaacaattt atcagacaat ctgtgtgggc  1980
actcgaccgg aattatcgat taactttatt attaaaaatt aaagaggtat atattaatgt  2040
atcgattaaa taaggaggaa taaaccatga ccatttcctc acctttgatt gacgtcgcca  2100
accttccaga catcaacacc actgccggca agatcgccga ccttaaggct cgccgcgcgg  2160
aagcccattt ccccatgggt gaaaaggcag tagagaaggt ccacgctgct ggacgcctca  2220
ctgcccgtga gcgcttggat tacttactcg atgagggctc cttcatcgag accgatcagc  2280
tggctcgcca ccgcaccacc gctttcggcc tgggcgctaa gcgtcctgca accgacggca  2340
tcgtgaccgg ctgggggcacc attgatggac gcgaagtctg catcttctcg caggacggca  2400
ccgtattcgg tgggcgcgtt ggtgaggtgt acggcgaaaa gatgatcaag atcatggagc  2460
tggcaatcga caccggccgc ccattgatcg gtctttacga aggcgctggc gctcgtattc  2520
aggacgcgc tgtctccctg gacttcattt cccagacctt ctaccaaaac attcaggctt  2580
ctggcgttat cccacagatc tccgtcatca tgggcgcatg tgcaggtggc aacgcttacg  2640
gcccagctct gaccgacttc gtggtcatgg tggacaagac ctccaagatg ttcgttaccg  2700
gcccagacgt gatcaagacc gtcaccggcg aggaaatcac ccaggaagag cttggcggag  2760
caaccaccca catggtgacc gctggtaact cccactacac cgctgcgacc gatgaggaag  2820
cactggattg ggtacaggac ctggtgtcct tcctcccatc caacaatcgc tcctacgcac  2880
cgatgaaga cttcgacgag gaagaaggcg gcgttgaaga aaacatcacc gctgacgatc  2940
tgaagctcga cgagatcatc ccagattccg cgaccgttcc ttacgacgtc cgcgatgtca  3000
tcgaatgcct caccgacgat ggcgaatacc tggaaatcca ggcagaccgc gcagaaaacg  3060
ttgttattgc attcggccgc atcgaaggcc agtccgttgg ctttgttgcc aaccagccaa  3120
cccagttcgc tggctgcctg gacatcgact cctctgagaa ggcagctcgc ttcgtccgca  3180
cctgcgacgc gttcaacatc ccaatcgtca tgcttgtcga cgtccccggc ttcctcccag  3240
gcgcaggcca ggagtacggt ggcattctgc gtcgtggcgc aaagctgctc tacgcatacg  3300
gcgaagcaac cgttccaaag atcaccgtca ccatgcgtaa ggcttacggc ggagcgtact  3360
gcgtgatggg ttcaagggc ttgggctctg acatcaacct gcatggcca accgcacaga  3420
tcgccgtcat gggcgctgct ggcgcagttg gattcatcta ccgcaaggag ctcatggcag  3480
ctgatgccaa gggcctcgat accgtagctc tggctaagtc cttcgagcgc gagtatgaag  3540
accacatgct caacccgtac cacgctgcag aacgtggcct gatcgacgcc gtgatcctgc  3600
caagcgaaac ccgcggacag atttcccgca accttcgcct gctcaagcac aagaacgtca  3660
ctcgccctgc tcgcaagcac ggcaacatgc cactgtaagg aggaaaacta aatgtcagtc  3720
gagactcgca agatcaccaa ggttcttgtc gctaaccgtg gtgagattgc aatccgcgtc  3780
ttccgtgcag ctcgagatga aggcatcgga tctgtcgccg tctacgcaga gccagatgca  3840
gatgcaccat tcgtgtcata tgcagacgag gcttttgccc tcggtggcca aacatccgct  3900
gagtcctacc ttgtcattga caagatcatc gatgcggccc gcaagtccgg cgccgacgcc  3960
atccacccg gctacggctt cctcgcagaa aacgctgact tcgcagaagc agtcatcaac  4020
gaaggcctcg tctggattgg accttcacct gagtccatcc gctccctcgg cgacaaggtc  4080
accgctcgcc acatcgcaga taccgccaag gctccaatgg ctcctggcac caaggaacca  4140
gtaaaagacg cagcagaagt tgtggctttc gctgaagaat cggtctccc aatcgccatc  4200
aaggcagctt cggtggcggg cggacgtggc atgaaggttg cctacaagat ggaagaagtc  4260
gctgacctct tcgagtccgc aacccgtgaa gcaaccgcag cgttcggccg cggcgagtgc  4320
ttcgtggagc gctacctgga caaggcacgc cacgttgagg ctcaggtcat cgccgataag  4380
```

-continued

```
cacggcaacg ttgttgtcgc cggaacccgt gactgctccc tgcagcgccg tttccagaag   4440
ctcgtcgaag aagcaccagc accattcctc accgatgacc agcgcgagcg tctccactcc   4500
tccgcgaagg ctatctgtaa ggaagctggc tactacggtg caggcaccgt tgagtacctc   4560
gttggctccg acggcctgat ctccttcctc gaggtcaaca cccgcctcca ggtggaacac   4620
ccagtcaccg aagagaccac cggcatcgac ctggtcccga aaatgttccg catcgcagaa   4680
ggccacgagc tctccatcaa ggaagatcca gctccacgcg gccacgcatt cgagttccgc   4740
atcaacggcg aagacgctgg ctccaacttc atgcctgcac caggcaagat caccagctac   4800
cgcgagccac agggcccagg cgtccgcatg gactccggtg tcgttgaagg ttccgaaatc   4860
tccggacagt tcgactccat gctggcaaag ctgatcgttt ggggcgacac ccgcgagcag   4920
gctctccagc gctcccgccg tgcacttgca gagtacgttg tcgagggcat gccaaccgtt   4980
atcccattcc accagcacat cgtggaaaac ccagcattcg tgggcaacga cgaaggcttc   5040
gagatctaca ccaagtggat cgaagaggtt tgggataacc caatcgcacc ttacgttgac   5100
gcttccgagc tcgacgaaga tgaggacaag accccagcac agaaggttgt tgtggagatc   5160
aacggccgtc gcgttgaggt tgcactccca ggcgatctgg cactcggtgg caccgctggt   5220
cctaagaaga aggccaagaa gcgtcgcgca ggtggtgcaa aggctggcgt atccggcgat   5280
gcagtggcag ctccaatgca gggcactgtc atcaaggtca acgtcgaaga aggcgctgaa   5340
gtcaacgaag gcgacaccgt tgttgtcctc gaggctatga agatgggaaaa ccctgtgaag   5400
gctcataagt ccggaaccgt aaccggcctt actgtcgctg caggcgaggg tgtcaacaag   5460
ggcgttgttc tcctcgagat caagtaatct agaggaggaa aactaaatga atgttgacat   5520
tagccgctct cgtgaaccgt tgaacgtgga actgttgaaa gaaaaactgc tgcagaacgg   5580
tgatttcggt caagtgatct acgagaaggt caccggctct accaatgcgg acctgctggc   5640
tctggcgggc agcggcgctc caaactggac cgtcaagact gttgaatttc aggaccaagc   5700
ccgtggccgt ctgggtcgtc cgtggagcgc accggagggt tcccaaacca tcgtcagcgt   5760
tctggtccaa ctgagcattg atcaggtgga ccgtattggt acgatcccgc tggccgcagg   5820
cttggctgtt atggatgcgc tgaatgatct gggcgtggag ggtgcaggcc tgaaatggcc   5880
gaacgatgtt cagatccacg gtaagaagtt gtgcggtatt ctggttgaag caaccggctt   5940
cgactccact ccgaccgtgg ttatcggttg gggtacgaat atctcgttga cgaaagaaga   6000
gctgccggtc ccgcacgcga ccagcctggc cctggagggt gttgaagttg accgtacgac   6060
gttcctgatt aacatgctga cccatctgca tacccgtctg gatcagtggc agggtccgtc   6120
tgtggactgg ctggatgact atcgcgcggt ttgtagcagc attggccaag atgtgcgtgt   6180
cctgctgcct ggtgacaaag agctgctggg cgaggcgatt ggcgtggcga ccggtggtga   6240
gatccgtgtg cgcgacgcca gcggcacggt ccacacgctg aatgcgggtg aaatcacgca   6300
tctgcgtttg caataaaagc ttgtttaaac ggtctccagc ttggctgttt tggcggatga   6360
gagaagattt tcagcctgat acagattaaa tcagaacgca gaagcggtct gataaaacag   6420
aatttgcctg gcggcagtag cgcggtggtc ccacctgacc ccatgccgaa ctcagaagtg   6480
aaacgccgta gcgccgatgg tagtgtgggg tctccccatg cgagagtagg gaactgccag   6540
gcatcaaata aaacgaaagg ctcagtcgaa agactgggcc tttcgtttta tctgttgttt   6600
gtcggtgaac gctctcctga cgcctgatgc ggtattttct ccttacgcat ctgtgcggta   6660
tttcacaccg catatggtgc actctcagta caatctgctc tgatgccgca tagttaagcc   6720
agccccgaca cccgccaaca cccgctgacg agcttagtaa agccctcgct agattttaat   6780
gcggatgttg cgattacttc gccaactatt gcgataacaa gaaaaagcca gcctttcatg   6840
atatatctcc caatttgtgt agggcttatt atgcacgctt aaaaataata aaagcagact   6900
tgacctgata gtttggctgt gagcaattat gtgcttagtg catctaacgc ttgagttaag   6960
ccgcgccgcg aagcggcgtc ggcttgaacg aattgttaga cattatttgc cgactacctt   7020
ggtgatctcg cctttcacgt agtggacaaa ttcttccaac tgatctgcgc gcgaggccaa   7080
gcgatcttct tcttgtccaa gataagcctg tctagcttca agtatgacgg gctgatactg   7140
ggccggcagg cgctccattg cccagtcggc agcgacatcc ttcggcgcga ttttgccggt   7200
tactgcgctg taccaaatgc gggacaacgt aagcactaca tttcgctcat cgccagccca   7260
gtcgggcggc gagttccata gcgttaaggt ttcatttagc gcctcaaata gatcctgttc   7320
aggaaccgga tcaaagagtt cctccgccgc tggacctacc aaggcaacgc tatgttctct   7380
tgcttttgtc agcaagatag ccagatcaat gtcgatcgtg gggctcgaa agatacctgc   7440
aagaatgtca ttgcgctgcc attctccaaa ttgcagttcg cgcttagctg gataacgcca   7500
cggaatgatg tcgtcgtgca caacaatggt gacttctaca gcgcggagaa tctcgctctc   7560
tccagggga gccgaagttt ccaaaaggtc gttgatcaaa gctcgccgcg ttgtttcatc   7620
aagccttacg gtcaccgtaa ccagcaaatc aatatcactg tgtggcttca ggccgccatc   7680
cactgcggag ccgtacaaat gtacggccag caacgtcggt tcgagatggc gctcgatgac   7740
gccaactacc tctgatagtt gagtcgatac ttcggcgatc accgcttccc tcatgatgtt   7800
taactttgtt ttagggcgac tgccctgctg cgtaacatcg ttgctgctcc ataacatcaa   7860
acatcgaccc acggcgtaac gcgcttgctg cttggatgcc cgaggcatag actgtacccc   7920
aaaaaaacag tcataacaag ccatgaaaac cgccactgcg ccgttaccac cgctgcgttc   7980
ggtcaaggtt ctgaccagt tgcgtgagcg catacgctac ttgcattaca gcttacgaac   8040
cgaacaggct tatgtccact gggttcgtgc cttcatccgt ttccacggtg tgcgtcaccc   8100
ggcaaccttg ggcagcagcg aagtcgaggc atttctgtcc tggctggcga acgagcgcaa   8160
ggtttcggtc tccacgcatc gtcaggcatt ggcggcctcg ctgttcttct acggcaaggt   8220
gctgtgcacg gatctgccct ggcttcagga gatcggaaga cctcggccgt cgcggcgctt   8280
gccggtggtg ctgaccccgg atgaagtggt tcgcatcctc ggttttctgg aaggcgagca   8340
tcgtttgttc gcccagcttc tgtatggaac gggcatgcgg atcagtgagg gtttgcaact   8400
gcgggtcaag gatctggatt tcgatcacgg cacgatcatc gtgcgggagg gcaagggctc   8460
caaggatcgg gccttgatgt tacccgagag cttggcaccc agcctgcgcg agcaggggatca   8520
ttaattccca cgggtttgc tgcccgcaaa cgggctgttc tggtgttgct agtttgttat   8580
cagaatcgca gatccggctt cagccggttt gccggctgaa agcgctattt cttccagaat   8640
tgccatgatt ttttccccac gggaggcgtc actggctccc gtgttgtcgg cagctttgat   8700
tcgataagca gcatcgcctg tttcaggctg tctatgtgtg actgttgagc tgtaacaagt   8760
tgtctcaggt gttcaatttc atgttctagt tgctttgttt tactggtttc acctgttcta   8820
ttaggtgtta catgctgttc atctgttaca ttgtcgatct gttcatggtg aacagctttg   8880
aatgcaccaa aaactcgtaa aagctctgat gtatctatct tttttacacc gttttcatct   8940
gtgcatatgg acagttttcc ctttgatatg taacggtgaa cagttgttct acttttgttt   9000
gttagtcttg atgcttcact gatagataca agagccataa gaacctcaga tccttccgta   9060
tttagccagt atgttctcta gtgtggttcg ttgttttgc gtgagccatg agaacgaacc   9120
```

-continued

```
attgagatca tacttacttt gcatgtcact caaaaatttt gcctcaaaac tggtgagctg   9180
aatttttgca gttaaagcat cgtgtagtgt ttttcttagt ccgttatgta ggtaggaatc   9240
tgatgtaatg gttgttggta ttttgtcacc attcattttt atctggttgt tctcaagttc   9300
ggttacgaga tccatttgtc tatctagttc aacttggaaa atcaacgtat cagtcgggcg   9360
gcctcgctta tcaaccacca atttcatatt gctgtaagtg tttaaatctt tacttattgg   9420
tttcaaaacc cattggttaa gccttttaaa ctcatggtag ttattttcaa gcattaacat   9480
gaacttaaat tcatcaaggc taatctctat atttgccttg tgagttttct tttgtgttag   9540
ttcttttaat aaccactcat aaatcctcat agagtatttg ttttcaaaag acttaacatg   9600
ttccagatta tattttatga attttttaa ctggaaaaga taaggcaata tctcttcact   9660
aaaaactaat tctaatttt cgcttgagaa cttggcatag tttgtccact ggaaaatctc   9720
aaagccttta accaaaggat tcctgatttc cacagttctc gtcatcagct ctctggttgc   9780
tttagctaat acaccataag cattttccct actgatgttc atcatctgag cgtattggtt   9840
ataagtgaac gataccgtcc gttctttcct tgtagggtt tcaatcgtgg ggttgagtag   9900
tgccacacag cataaaatta gcttggtttc atgctccgtt aagtcatagc gactaatcgc   9960
tagttcattt gctttgaaaa caactaattc agacatacat ctcaattggt ctaggtgatt   10020
ttaat                                                                 10025

SEQ ID NO: 63          moltype = DNA  length = 11469
FEATURE                Location/Qualifiers
misc_feature           1..11469
                       note = Synthetic polynucleotide
source                 1..11469
                       mol_type = other DNA
                       organism = synthetic construct SEQUENCE: 63
cactatacca attgagatgg gctagtcaat gataattact agtccttttc ctttgagttg   60
tgggtatctg taaattctgc tagacctttg ctggaaaaact tgtaaattct gctagaccct  120
ctgtaaattc cgctagacct ttgtgtgttt tttttgttta tattcaagtg gttataattt   180
atagaataaa gaaagaataa aaaaagataa aaagaataga tcccagccct gtgtataact   240
cactacttta gtcagttccg cagtattaca aaaggatgtc gcaaacgctg tttgctcctc   300
tacaaaacag accttaaaac cctaaaggcg tcggcatccg cttacagaca agctgtgacc   360
gtctccggga gctgcatgtg tcagaggttt tcaccgtcat caccgaaacg cgcgaggcag   420
cagatcaatt cgcgcgcgaa ggcgaagcgg catgcattta cgttgacacc atcgaatggt   480
gcaaaacctt tcgcggtatg gcatgatagc gcccggaaga gagtcaattc agggtggtga   540
atgtgaaacc agtaacgtta tacgatgtcg cagaatatgc cggtgtctct tatcagaccg   600
tttcccgcgt ggtgaaccag gccagccacg tttctgcgaa aacgcgggaa aaagtggaag   660
cggcgatggc ggagctgaat tacattccca accgcgtggc acaacaactg gcgggcaaac   720
agtcgttgct gattggcgtt gccacctcca gtctggccct gcacgcgccg tcgcaaattg   780
tcgcggcgat taaatctcgc gccgatcaac tgggtgccag cgtggtggtg tcgatggtag   840
aacgaagcgg cgtcgaagcc tgtaaagcgg cggtgcacaa tcttctcgcg caacgcgtca   900
gtgggctgat cattaactat ccgctggatg accaggatgc cattgctgtg gaagctgcct   960
gcactaatgt tccggcgtta tttcttgatg tctctgacca gacacccatc aacagtatta   1020
ttttctccca tgaagacggt acgcgactgg gcgtggagca ttgggtcacc   1080
agcaaatcgc gctgttagcg ggcccattaa gttctgtctc ggcgcgtctg cgtctggctg  1140
gctggcataa atatctcact cgcaatcaaa ttcagccgat agcggaacgg gaaggcgact  1200
ggagtgccat gtccggtttt caacaaacca tgcaaatgct gaatgagggc atcgttccca  1260
ctgcgatgct ggttgccaac gatcagatgg cgctgggcgc aatgcgcgcc attaccgagt  1320
ccgggctgcg cgttggtgcg gatatctcgg tagtgggata cgacgatacc gaagacagct  1380
catgttatat cccgccgtta accaccatca aacaggattt tcgcctgctg gggcaaacca  1440
gcgtggaccg cttgctgcaa ctctctcagg ccaggcggt gaagggcaat cagctgttgc  1500
ccgtctcact ggtgaaaaga aaaaccaccc tggcgcccaa tacgcaaacc gcctctccc   1560
gcgcgttggc cgattcatta atgcagctgg cacgacaggt ttcccgactg gaaagcgggc  1620
agtgagcgca acgcaattaa tgtaagttag cgcgaattga tctggtttga cagcttatca  1680
tcgactgcac ggtgcaccaa tgcttctggc gtcaggcagc catcggaagc tgtggtatgg  1740
ctgtgcaggt cgtaaatcac tgcataattc gtgtcgctca aggcgcactc ccgttctgga  1800
taatgttttt tgcgccgaca tcataacggt tctggcaaat attctgaaat gagctgttga  1860
caattaatca tccggctcgt ataatgtgtg gaattgtgag cggataacaa tttcacacag  1920
gaaacagcgc cgctgagaaa aagcgaagcg gcactgctct ttaacaattt atcagacaat  1980
ctgtgtgggc actcgaccgg aattatcgat taactttatt attaaaaatt aaagaggtat  2040
atattaatgt atcgattaaa taaggaggaa taaaccatga aacgtctcgg aaccctggac  2100
gcctcctggc tggcggttga atctgaagac accccgatgc atgtgggtac gcttcagatt  2160
ttctcactgc cggaaggcgc accagaaacc ttcctgcgtg acatggtcac tcgaatgaaa  2220
gaggccggc atgtggcacc accctgggga tacaaactgg cctggtctgg tttcctcggg  2280
cgcgtgatcg ccccggcctg gaaagtcgat aaggatatcg atctggatta tcacgtgatt  2340
cactcagccc tgcctcgccc cggcggggag cgcgaactgg gtattctggt atcccgactg  2400
cactctaacc ccctggattt ttcccgccct ctttgggaat gccacgttat tgaaggcctg  2460
gagaataacc gttttgccct ttacaccaaa atgcaccact cgatgattga cggcatcagc  2520
ggcgtgcgac tgatgcagag ggtgctcacc accgatcccg aacgctgcaa tatgccaccg  2580
ccctggacgg tacgcccaca ccaacgccgt ggtgcaaaaa ccgacaaaga ggccagccgt  2640
cccgcagcgg tttcccaggc aatggacgcc ctgaagctcc aggcagacat ggcccccagg  2700
ctgtggcagg ccggcaatcg cctggtgcat tcggttcgac acccggaaga cggactgacc  2760
gcgcccttca ctgaccggt ttcggtgctc aataccgggg ttaccgcgca gcgacgtttt  2820
gccacccagc attatcaact ggaccggctg aaaaacctgg cccatgcttc cggcggttcc  2880
ttgaacgaca tcgtgcttta cctgtgtggc accgcattgc gcgctttct ggctgagcag  2940
aacaatctgc cagacacccc gctgacggct ggtataccgg tgaatatccg gccggcagac  3000
gacgagggta cgggcaccca gatcagtttt atgattgcct cgctggccac cgacgaagct  3060
gatccgttga accgcctgca acagatcaaa acctcgaccc cgacgggcca ggagcacctg  3120
cagaaacttc caaaaagtgc cctgacccag tacaccatgc tgctgatgtc accctacatt  3180
ctgcaattga tgtcaggtct cggggggagg atgcgaccag tcttcaacgt gaccatttcc  3240
```

-continued

```
aacgtgcccg gcccggaagg cacgctgtat tatgaaggag cccggcttga ggccatgtat   3300
ccggtatcgc taatcgctca cggcggcgc ctgaacatca cctgcctgag ctatgccgga     3360
tcgctgaatt tcggttttac cggctgtcgg gatacgctgc cgagcatgca gaaactggcg    3420
gtttataccg gtgaagctct ggatgagctg gaatcgctga ttctgccacc caagaagcgc   3480
gcccgaaccc gcaagtaact cgaggaggaa aactaaatga ccatttcctc acctttgatt   3540
gacgtcgcca accttccaga catcaacacc actgccggca agatcgccga ccttaaggct   3600
cgccgcgcgg aagcccattt ccccatgggt gaaaaggcag tagagaaggt ccacgctgct    3660
ggacgcctca ctgcccgtga gcgcttggat tacttactcg atgagggctc cttcatcgag   3720
accgatcagc tggctcgcca ccgcaccacc gctttcggcc tgggcgctaa gcgtcctgca    3780
accgacggca tcgtgaccgg ctggggcacc attgatggac gcgaagtctg catcttctcg    3840
caggacggca ccgtattcgg tggcgcgctt ggtgaggtgt acggcgaaaa gatgatcaag    3900
atcatggagc tggcaatcga caccggccgc ccattgatcg gtctttacga aggcgctggc    3960
gctcgtattc aggacggcgc tgtctccctg gacttcattt cccagacctt ctaccaaaac    4020
attcaggctt ctggcgttat cccacagatc tccgtcatca tgggcgcatg tgcaggtggc   4080
aacgcttacg gcccagctct gaccgacttc gtggtcatgg tggacaagac ctccaagatg   4140
ttcgttaccg gcccagacgt gatcaagacc gtcaccggcg aggaaatcac ccaggaagag    4200
cttggcggag caaccaccca catggtgacc gctggtaact cccactacac cgctgcgacc   4260
gatgaggaag cactggattg ggtacaggac ctggtgtcct tcctcccatc caacaatcgc   4320
tcctacgcac cgatggaaga cttcgacgag gaagaaggcg gcgttgaaga aaacatcacc   4380
gctgacgatc tgaagctcga cgagatcatc ccagattccg cgaccgttcc ttacgacgtc   4440
cgcgatgtca tcgaatgcct caccgacgat ggcgaatacc tggaaatcca ggcagaccgc   4500
gcagaaaacg ttgttattgc attcggccgc atcgaaggcc agtccgttgg cttttgttcc   4560
aaccagccaa cccagttcgc tggctgcctg gacatcgact cctctgagaa ggcagctcgc   4620
ttcgtccgca cctgcgacgc gttcaacatc ccaatcgtca tgcttgtcga cgtccccggc   4680
ttcctcccag gcgcaggcca ggagtacggt ggcattctgc gtcgtggcgc aaagctgctc   4740
tacgcatacg gcgaagcaac cgttccaaag atcaccgtca ccatgcgtaa ggcttacggc   4800
ggagcgtact gcgtgatggg ttccaagggc ttgggctctg acatcaacct tgcatggcca   4860
accgcacaga tcgccgtcat gggcgctgct ggcgcagttg gattcatcta ccgcaaggag   4920
ctcatggcag ctgatgccaa gggcctcgat accgtagctc tggctaagtc cttcgagcgc   4980
gagtatgaag accacatgct caacccgtac cacgctgcag aagtggcct gatcgacgcc    5040
gtgatcctgc caagcgaaac ccgcggacag atttcccgca accttcgcct gctcaagcac   5100
aagaacgtca ctcgccctgc tcgcaagcac ggcaacatgc cactgtaagg aggaaaacta    5160
aatgtcagtc gagactcgca agatcaccaa ggttcttgtc gctaaccgtg gtgagattgc    5220
aatccgcgtg ttccgtgcag ctcgagatga aggcatcgga tctgtcgccg tctacgcaga    5280
gccagatgca gatgcaccat tcgtgtcata tgcagacgag gcttttgccc tcggtggcca   5340
aacatccgct gagtcctacc ttgtcattga caagatcatc gatgcggccc gcaagtccgg   5400
cgccgacgcc atccacccc gctacggct cctcgcagaa aacgctgact cgcagaagc     5460
agtcatcaac gaaggcctga tctggattgg accttcacct gagtccatcc gctccctcgg   5520
cgacaaggtc accgctcgcc acatcgcaga taccgccaag gctccaatgg ctcctggcac    5580
caaggaacca gtaaaagacg cagcagaagt tgtggctttc gctgaagaat tcggtctccc    5640
aatcgccatc aaggcagctt tcggtggcgg cggacgtggc atgaaggttg cctacaagat   5700
ggaagaagtc gctgacctct tcgagtccgc aacccgtgaa gcaaccgcag cgttcggccg    5760
cggcgagtgc ttcgtggagc gctacctgga caaggcacgc acgttgagg ctcaggtcat     5820
cgccgataag cacggcaacg ttgttgtcgc cggaacccgt gactgctccc tgcagcgccg    5880
tttcagaag ctcgtcgaag aagcaccagc accattcctc accgatgacc agcgcgagcg     5940
tctccactcc tccgcgaagg ctatctgtaa ggaagctggc tactacggtg caggcaccgt   6000
tgagtacctc gttggctcg acggcctgat ctccttcctc gaggtcaaca cccgcctcca    6060
ggtggaacac ccagtcaccg aagagaccac cggcatcgac ctggtccgcg aaatgttccg   6120
catcgcagaa ggccacgagc tctccatcaa ggaagatcca gctccacgcg gccacgcatt   6180
cgagttccgc atcaacggcg aagacgctgg ctccaacttc atgcctgcac caggcaagat   6240
caccagctac cgcgagccac agggcccagg cgtccgcatg gactccggtg tcgttgaagg   6300
ttccgaaatc tccggacagt tcgactccat gctggcaaag ctgatcgttt ggggcgacac    6360
ccgcgagcag gctctccagc gctcccgccg tgcacttgca gagtacgttg tcgagggcat    6420
gccaaccgtt atcccattcc accagcacat cgtggaaaac ccagcattcg tgggcaacga   6480
cgaaggcttc gagatctaca ccaagtggat cgaagaggtt tgggataacc caatcgcacc    6540
ttacgttgac gcttccgagc tcgacgaaga tgaggacaag accccagcac agaaggttgt   6600
tgtggagatc aacggccgtc gcgttgaggt tgcactccca ggcgatctgg cactcggtgg    6660
caccgctggt cctaagaaga aggccaagaa gcgtcgcgca ggtggtgcaa aggctggcgt   6720
atccggcgat gcagtggcag ctccaatgca gggcactgtc atcaaggtca acgtcgaaga   6780
aggcgctgaa gtcaacgaag gcgacaccgt tgttgtcctc gaggctatga agatggaaaa    6840
ccctgtgaag gctcataagt ccggaaccgt aaccggcctt actgtcgctg caggcgaggg   6900
tgtcaacaag ggcgttgttc tcctcgagat caagtaatct agaggaggaa aactaaatga    6960
atgttgacat tagccgctct cgtgaaccgt tgaacgtgga actgttgaaa gaaaaactgc   7020
tgcagaacgg tgatttcggt caagtgatct acgagaaggt caccggctct accaatgcgg    7080
acctgctggc tctggcgggc agcggcgctc caaactggac cgtcaagact gttgaatttc   7140
aggaccacgc ccgtggccgt ctgggtcgtc cgtgagcgc accggaggt tcccaaacca     7200
tcgtcagcgt tctggtccaa ctgagcattg atcaggtgga ccgtattggt acgatcccgc    7260
tggccgcagg cttggctgtt atggatgcgc tgaatgatct gggcgtggag ggtgcaggcc   7320
tgaaatggcc gaacgatgtt cagatccacg gtaagaagtt gtgcggtatt ctggttgaag    7380
caaccggctt cgactccact ccgaccgtgg ttatcggttg gggtacgaat atctcgttga    7440
cgaaagaaga gctgccggtc ccgcacgcga ccagcctggc cctggaggt gttgaagttg     7500
accgtacgac gttcctgatt aacatgctga cccatctgca tacccgtctg gatcagtggc   7560
agggtccgtc tgtggactgg ctggatgact atcgcgcggt ttgtagcagc attggccaag   7620
atgtgcgtgt cctgctgcct ggtgacaaag agctgctggg cgagatt ggcgtggcaa     7680
ccggtggtgca gatccgtgtg cgcgacgcca gcggcacggc ccacacgctg aatgcgggtg   7740
aaatcacgca tctgcgtttg caataagttt aaacggtctc cagcttggct gttttggcgg    7800
atgagagaag attttcagcc tgatacagat taaatcagaa cgcagaagcg gtctgataaa   7860
acagaatttg cctggcggca gtagcgcggt ggtcccacct gaccccatgc cgaactcaga   7920
agtgaaacgc cgtagcgccg atggtagtgt ggggtctccc catgcgagag tagggaactg   7980
```

```
ccaggcatca aataaaacga aaggctcagt cgaaagactg ggcctttcgt tttatctgtt   8040
gtttgtcggt gaacgctctc ctgacgcctg atgcggtatt ttctccttac gcatctgtgc   8100
ggtatttcac accgcatatg gtgcactctc agtacaatct gctctgatgc cgcatagtta   8160
agccagcccc gacacccgcc aacacccgct gacgagctta gtaaagccct cgctagattt   8220
taatgcggat gttgcgatta cttcgccaac tattgcgata acaagaaaaa gccagccttt   8280
catgatatat ctcccaattt gtgtagggct tattatgcac gcttaaaaat aataaaagca   8340
gacttgacct gatagtttgg ctgtgagcaa ttatgtgctt agtgcatcta acgcttgagt   8400
taagccgcgc cgcgaagcgg cgtcggcttg aacgaattgt tagacattat ttgccgacta   8460
ccttggtgat ctcgcctttc acgtagtgga caaattcttc caactgatct gcgcgcgagg   8520
ccaagcgatc ttcttcttgt ccaagataag cctgtctagc ttcaagtatg acgggctgat   8580
actgggccgg caggcgctcc attgcccagt cggcagcgac atccttcggc gcgatttttgc   8640
cggttactgc gctgtaccaa atgcgggaca acgtaagcac tacatttcgc tcatcgccag   8700
cccagtcggg cggcgagttc catagcgtta aggtttcatt tagcgcctca aatagatcct   8760
gttcaggaac cggatcaaag agttcctccg ccgctgacc taccaaggca acgctatgtt   8820
ctcttgcttt tgtcagcaag atagccagat caatgtcgat cgtggctggc tcgaagatac   8880
ctgcaaggaat gtcattgcgc tgccattctc caaattgcag ttcgcgctta gctggataac   8940
gccacggaat gatgtcgtcg tgcacaacaa tggtgacttc tacagcgcgg agaatctcgc   9000
tctctccagg ggaagccgaa gtttccaaaa ggtcgttgat caaagctcgc cgcgttgttt   9060
catcaagcct tacggtcacc gtaaccagca aatcaatatc actgtgtggc ttcaggccgc   9120
catccactgc ggagccgtac aaatgtacgg ccagcaacgt cggttcgaga tggcgctcga   9180
tgacgccaac tacctctgat agttgagtcg atacttcggc gatcaccgct tccctcatga   9240
tgtttaactt tgtttaggg cgactgccct gctgcgtaac atcgttgctg ctccataaca   9300
tcaaacatcg acccacggcg taacgcgctt gctgcttgga tgcccgaggc atagactgta   9360
ccccaaaaaa acagtcataa caagccatga aaaccgccac tgcgccgtta ccaccgctgc   9420
gttcggtcaa ggttctggac cagttgcgtg agcgcatacg ctacttgcat tacagcttac   9480
gaaccgaaca ggcttatgtc cactgggttc gtgccttcat ccgtttccac ggtgtgcgtc   9540
acccggcaac cttgggcagc agcgaagtcg aggcatttct gtcctggctg gcgaacgagc   9600
gcaaggtttc ggtctccacg catcgtcagg cattggcggc cttgctgttc ttctacggca   9660
aggtgctgtg cacggatctg ccctggcttc aggagatcgg aagacctcgg ccgtcgcggc   9720
gcttgccggt ggtgctgacc ccggatgaag tggttcgcat cctcggtttt ctggaaggcg   9780
agcatcgttt gttcgcccag cttctgtatg gaacgggcat gcggatcagt gagggtttgc   9840
aactgcgggt caaggatctg gatttcgatc acggcacgat catcgtgcgg gagggcaagg   9900
gctccaagga tcgggccttg atgttacccg agagcttggc acccagcctg cgcgagcagg   9960
ggaattaatt cccacgggtt ttgctgcccg caaacgggct gttctggtgt tgctagtttg   10020
ttatcagaat cgcagatccg gcttcagccg gtttgccggc tgaaagcgct atttcttcca   10080
gaattgccat gatttttttcc ccacgggagg cgtcactggc tcccgtgttg tcggcagctt   10140
tgattcgata agcagcatcg cctgtttcag gctgtctatg tgtgactgtt gagctgtaac   10200
aagttgtctc aggtgttcaa tttcatgttc tagttgcttt gttttactgg tttcacctgt   10260
tctattaggt gttacatgct gttcatctgt tacattgtcg atctgttcat ggtgaacagc   10320
tttgaatgca ccaaaaactc gtaaaagctc tgatgtatct atcttttta caccgttttc   10380
atctgtgcat atggacagtt ttccctttga tatgtaacgg tgaacagttg ttctactttt   10440
gtttgttagt cttgatgctt cactgataga tacaagagcc ataagaacct cagatccttc   10500
cgtatttagc cagtatgttc tctagtgtgg ttcgttgttt ttcgtgagc catgagaacg   10560
aaccattgag atcatactta ctttgcatgt cactcaaaaa ttttgcctca aaactggtga   10620
gctgaatttt tgcagttaaa gcatcgtgta gtgtttttct tagtccgtta tgtaggtagg   10680
aatctgatgt aatggttgtt ggtattttgt caccattcat ttttatctgg ttgttctcaa   10740
gttcggttac gagatccatt tgtctatcta gttcaacttg gaaaatcaac gtatcagtcg   10800
ggcggcctcg cttatcaacc accaatttca tattgctgta agtgtttaaa tctttactta   10860
ttggtttcaa aacccattgg ttaagccttt taaactcatg gtagttattt tcaagcatta   10920
acatgaactt aaattcatca aggctaatct ctatatttgc cttgtgagtt ttcttttgtg   10980
ttagttcttt taataaccac tcataaatcc tcatagagta tttgttttca aaagacttaa   11040
catgttccag attatatttt atgaattttt ttaactggaa aagataaggc aatatctctt   11100
cactaaaaac taattctaat ttttcgcttg agaacttggc atagtttgtc cactggaaaa   11160
tctcaaagcc tttaaccaaa ggattcctga tttccacagt tctcgtcatc agctctctgg   11220
ttgctttagc taatacacca taagcatttt ccctactgat gttcatcatc tgagcgtatt   11280
ggttataagt gaacgatacc gtccgttctt tccttgtagg gtttttcaatc gtgggttga   11340
gtagtgccac acagcataaa attagcttgg tttcatgctc cgttaagtca tagcgactaa   11400
tcgctagttc atttgctttg aaaacaacta attcagacat acatctcaat tggtctaggt   11460
gattttaat                                                           11469
```

SEQ ID NO: 64        moltype = AA  length = 1173
FEATURE              Location/Qualifiers
source               1..1173
                     mol_type = protein
                     organism = Mycobacterium smegmatis SEQUENCE: 64
```
MTSDVHDATD GVTETALDDE QSTRRIAELY ATDPEFAAAA PLPAVVDAAH KPGLRLAEIL   60
QTLFTGYGDR PALGYRAREL ATDEGGRTVT RLLPRFDTLT YAQVWSRVQA VAAALRHNFA  120
QPIYPGDAVA TIGFASPDYL TLDLVCAYLG LVSVPLQHNA PVSRLAPILA EVEPRILTVS  180
AEYLDLAVES VRDVNSVSQL VVFDHHPEVD DHRDALARAR EQLAGKGIAV TTLDAIADEG  240
AGLPAEPIYT ADHDQRLAMI LYTSGSTGAP KGAMYTEAMV ARLWTMSFIT GDPTPVINVN  300
FMPLNHLGGR IPISTAVQNG GTSYFVPESD MSTLFEDLAL VRPTELGLVP RVADMLYQHH  360
LATVDRLVTQ GADELTAEKQ AGAELREQVL GGRVITGFVS TAPLAAEMRA FLDITLGAHI  420
VDGYGLTETG AVTRDGVIVR PPVIDYKLID VPELGYFSTD KPYPRGELLV RSQTLTPGYY  480
KRPEVTASVF DRDGYYHTGD VMAETAPDHL VYVDRRNNVL KLAQGEFVAV ANLEAVFSGA  540
ALVRQIFVYG NSERSPLLAV VVPTEALEQ YDPAALKAAL ADSLQRTARD AELQSYEVPA  600
DFIVETEPFS AANGLLSGVG KLLRPNLKDR YGQRLEQMYA DIAATQANQL RELRRAAATQ  660
PVIDTLTQAA ATILGTGSEV ASDAHFTDLG GDSLSALTLS NLLSDFFGFE VPVGTIVNPA  720
TNLAQLAQHI EAQRTAGDRR PSFTTVHGAD ATEIRASELT LDKFIDAETL RAAPGLPKVT  780
```

-continued

```
TEPRTVLLSG ANGWLGRFLT LQWLERLAPV GGTLITIVRG RDDAAARARL TQAYDTDPEL  840
SRRFAELADR HLRVVAGDIG DPNLGLTPEI WHRLAAEVDL VVHPAALVNH VLPYRQLFGP  900
NVVGTAEVIK LALTERIKPV TYLSTVSVAM GIPDFEEDGD IRTVSPVRPL DGGYANGYGN  960
SKWAGEVLLR EAHDLCGLPV ATFRSDMILA HPRYRGQVNV PDMFTRLLLS LLITGVAPRS  1020
FYIGDGERPR AHYPGLTVDF VAEAVTTLGA QQREGYVSYD VMNPHDDGIS LDVFVDWLIR  1080
AGHPIDRVDD YDDWVRRFET ALTALPEKRR AQTVLPLLHA FRAPQAPLRG APEPTEVFHA  1140
AVRTAKVGPG DIPHLDEALI DKYIRDLREF GLI                              1173
```

PRODUCTION OF FATTY ACID DERIVATIVES

CROSS-REFERENCE TO RELATED APPLICATIONS

This application is a continuation of U.S. application Ser. No. 17/335,812 filed Jun. 1, 2021, which is divisional of U.S. application Ser. No. 15/650,285, now U.S. Pat. No. 11,060,099, filed Jul. 14, 2017, which is a divisional of U.S. application Ser. No. 14/390,378 filed Oct. 2, 2014, which is a U.S. National Stage Application under 35 U.S.C. § 371 of International Application No. PCT/US2013/035037 filed Apr. 2, 2013, which claims the benefit of U.S. Provisional Application No. 61/619,324 filed Apr. 2, 2012. The entire disclosure of each patent document listed above is incorporated by reference.

SEQUENCE LISTING

This application contains references to amino acid sequences and/or nucleic acid sequences which have been submitted concurrently herewith as the sequence listing .xml file entitled "ST26_SL_Conversion_28_Jun_2023.xml", file size 118 KiloBytes (KB), created on Jun. 28, 2023. The aforementioned sequence listing is hereby incorporated by reference in its entirety.

FIELD

The disclosure relates to recombinant host cells including strain modifications effective to improve titer, yield and/or productivity of fatty acid derivatives. The disclosure further relates to cell cultures including the recombinant host cells for the fermentative production of fatty acid derivatives and compositions thereof.

BACKGROUND

Fatty acid derivatives including fatty aldehydes, fatty alcohols, hydrocarbons (alkanes and olefins), fatty esters (e.g., waxes, fatty acid esters, or fatty esters), and ketones denote important categories of industrial chemicals and fuels. These molecules and their derivatives have numerous applications including, but not limited to, use as surfactants, lubricants, plasticizers, solvents, emulsifiers, emollients, thickeners, flavors, fragrances, and fuels. Crude petroleum is currently a primary source of raw materials for producing petrochemicals and fuels. The two main classes of raw materials derived from petroleum are short chain olefins (e.g., ethylene and propylene) and aromatics (e.g., benzene and xylene isomers). These raw materials are derived from longer chain hydrocarbons in crude petroleum by cracking it at considerable expense using a variety of methods, such as catalytic cracking, steam cracking, or catalytic reforming. These raw materials can be used to make petrochemicals such as monomers, solvents, detergents, and adhesives, which otherwise cannot be directly refined from crude petroleum. Petrochemicals, in turn, can be used to make specialty chemicals, such as plastics, resins, fibers, elastomers, pharmaceuticals, lubricants, gels, and the like. Particular specialty chemicals that can be produced from petrochemical raw materials include, but are not limited to, fatty acids, hydrocarbons, fatty aldehydes, fatty alcohols, esters, and ketones.

Hydrocarbons, for example, have many commercial uses. As such, shorter chain alkanes and alkenes are used in transportation fuels. Longer chain alkenes are used in plastics, lubricants, and synthetic lubricants. In addition, alkenes are used as a feedstock to produce alcohols, esters, plasticizers, surfactants, tertiary amines, enhanced oil recovery agents, fatty acids, thiols, alkenylsuccinic anhydrides, epoxides, chlorinated alkanes, chlorinated alkenes, waxes, fuel additives, and drag flow reducers. Similarly, esters have many commercial uses. For example, biodiesel, an alternative fuel, is made of esters (e.g., fatty acid methyl ester, fatty acid ethyl esters, etc.). Some low molecular weight esters are volatile with a pleasant odor which makes them useful as fragrances or flavoring agents. In addition, esters are used as solvents for lacquers, paints, and varnishes. Furthermore, some naturally occurring substances, such as waxes, fats, and oils are also made of esters. Esters are further used as softening agents in resins and plastics, plasticizers, flame retardants, and additives in gasoline and oil. In addition, esters can be used in the manufacture of polymers, films, textiles, dyes, and pharmaceuticals.

Aldehydes are used to produce a large number of specialty chemicals. For example, aldehydes are used to produce polymers, resins (e.g., Bakelite), dyes, flavorings, plasticizers, perfumes, pharmaceuticals, and other chemicals, some of which may be used as solvents, preservatives, or disinfectants. In addition, certain natural and synthetic compounds, such as vitamins and compounds used as hormones are aldehydes. Furthermore, many sugars contain aldehyde groups. Fatty aldehydes can be converted to fatty alcohols by chemical or enzymatic reduction. Similarly, fatty alcohols have many commercial uses as well. The shorter chain fatty alcohols are used in the cosmetic and food industries as emulsifiers, emollients, and thickeners. Due to their amphiphilic nature, fatty alcohols behave as nonionic surfactants, which are useful in personal care and household products, such as, for example, detergents. In addition, fatty alcohols are used in waxes, gums, resins, pharmaceutical salves and lotions, lubricating oil additives, textile antistatic and finishing agents, plasticizers, cosmetics, industrial solvents, and solvents for fats. Fatty alcohols such as aliphatic alcohols include a chain of 8 to 22 carbon atoms. Fatty alcohols usually have an even number of carbon atoms and a single alcohol group (—OH) attached to the terminal carbon. Some are unsaturated and some are branched. They are widely used in industrial chemistry. Most fatty alcohols in nature are found as waxes which are esters with fatty acids and fatty alcohols. They are produced by bacteria, plants and animals. Currently, fatty alcohols are produced via catalytic hydrogenation of fatty acids produced from natural sources, such as coconut oil, palm oil, palm kernel oil, tallow and lard, or by chemical hydration of alpha-olefins produced from petrochemical feedstocks. Fatty alcohols derived from natural sources have varying chain lengths. The chain length of fatty alcohols is important and specific to particular applications. Dehydration of fatty alcohols to alpha-olefins can also be accomplished by chemical catalysis.

Due to the inherent challenges posed by exploring, extracting, transporting and refining petroleum for use in chemical- and fuel products, there is a need in the art for a an alternate source which can be produced economically and efficiently for the use of chemical- and fuel production. Moreover, the burning of petroleum-based fuels has become a serious hazard to the environment, especially in light of the ever increasing population inhabiting the planet. Thus, there is a need for a petroleum replacement that does not cause the type of environmental damage created by exploring, extracting, transporting and refining petroleum.

One option of producing renewable petroleum is by engineering host cells to produce renewable petroleum products. Biologically derived fuels and chemicals offer advantages over petroleum based fuels. Biologically derived chemicals such as hydrocarbons (e.g., alkanes, alkenes, or alkynes), fatty alcohols, esters, fatty acids, fatty aldehydes, and ketones are directly converted from biomass to the desired chemical product. However, in order for the use of biologically-derived fatty acid derivatives from fermentable sugars or biomass to be commercially viable as a source for production of renewable chemicals and fuels, the process must be optimized for efficient conversion and recovery of product. The development of biologically derived fuels and chemicals has been one focus of research and development in recent years. Still, there remains a considerable need for improvements in the relevant processes and products in order for biologically-derived fuels and chemicals to become a commercially viable option. Areas that need improvement include the energy efficiency of the production process and the final product yield. The current disclosure addresses this need.

SUMMARY

One aspect of the disclosure provides a recombinant host cell having a genetically engineered polynucleotide sequence, wherein the polynucleotide sequence codes for one or more polypeptides that have a specific enzymatic activity. The polynucleotide sequence is exogenous or endogenous to the host cell. As such, the disclosure provides a recombinant host cell having a genetically engineered polynucleotide sequence encoding one or more polypeptides, wherein the polypeptides have activity selected from the group including, but not limited to, 3-hydroxydecanoyl-[acp] dehydratase (E.C. 4.2.1.60) activity; β-ketoacyl-ACP synthase I (E.C. 2.3.1.41) activity; β-ketoacyl-ACP synthase II (E.C. 2.3.1.179) activity; [acp] S-malonyltransferase {malonyl-CoA-ACP transacylase} (E.C. 2.3.1.39) activity; 3-oxoacyl-{β-ketoacyl}-ACP reductase (E.C. 1.1.1.100) activity; β-ketoacyl-ACP synthase III (E.C. 2.3.1.180) activity; enoyl-ACP reductase (NADH) (E.C. 1.3.1.9) activity; enoyl-ACP reductase (NADPH) (E.C. 1.3.1.10) activity; 3-hydroxy-acyl-[acp] dehydratase (E.C. 4.2.1.59) activity; and trans-2, cis-3-decenoyl-ACP isomerase (E.C. 5.3.3.14) activity, wherein the recombinant host cell produce a fatty acid derivative composition at a higher titer, yield or productivity than a corresponding wild type host cell when cultured in a medium containing a carbon source under conditions effective to express the polynucleotide. In a related aspect, the recombinant host cell produces the fatty acid derivative composition at a higher titer, yield and/or productivity when the polypeptide is expressed in combination with at least one other polypeptide of the enzymatic activity. In another aspect, the recombinant host cell produces the fatty acid derivative composition at a higher titer, yield or productivity when the polypeptide is expressed in combination with at least five other polypeptides of the enzymatic activity. In yet another aspect, the recombinant host cell produces the fatty acid derivative composition at a higher titer, yield or productivity when expressed in combination with at least two or three or four or five or six or more polypeptides of the enzymatic activity. In another related aspect, the recombinant host cell includes one or more genetically engineered polynucleotide sequences that further code for a polypeptide that is an acyl carrier protein (ACP). ACP can be in expressed in combination with one or more of the polypeptides that code for any of the enzymatic activities, wherein the ACP further increases the titer, yield and/or productivity of the recombinant host cell when cultured under appropriate conditions. In yet another related aspect, a genetically engineered polynucleotide sequence further encodes a polypeptide that has accABCD activity (E.C. 6.4.1.2). accABCD can be in expressed in combination with one or more of the polypeptides that code for any of the enzymatic activities, wherein the accABCD further increases the titer, yield and/or productivity of the recombinant host cell when cultured under appropriate conditions.

Another aspect of the disclosure provides a recombinant host cell having a genetically engineered polynucleotide sequence encoding one or more polypeptides, wherein the polypeptides have enzymatic activity including, but not limited to, trans-2, cis-3-decenoyl-ACP isomerase activity (fabA or fabM); β-ketoacyl-ACP synthase I (fabB); malonyl-CoA-ACP transacylase (fabD); β-ketoacyl-ACP synthase I (fabF or fabB); β-ketoacyl-ACP reductase (fabG); β-ketoacyl-ACP synthase III (fabH); enoyl-ACP reductase (fabI or fabL or fabV or fabK); and 3-hydrox-acyl-[acp] dehydratase (fabA or fabZ); trans-2-enoyl-ACP reductase II (fabK). In a related aspect, the polypeptide is selected from fabA, fabB, fabD, fabF, fabG, fabH, fabI, fabL, fabV, fabZ, fabM, and fabK and or combinations thereof. In yet another related aspect, the polypeptide is selected from FabA from *Salmonella typhimurium* (NP_460041); FabB from *Escherichia coli* (NP_416826); FabD from *Salmonella typhimurium* (NP_460164); FabG from *Salmonella typhimurium* (NP_460165); FabH from *Salmonella typhimurium* (NP_460163); FabZ from *Salmonella typhimurium* (NP_459232); FabM from *Streptococcus mutans* (AAN59379); FabK from *Streptococcus pneumoniae* (AAF98273); FabV from *Vibrio cholera* (YP_001217283); FabF from *Clostridium acetobutylicum* (NP_350156); FabI from *Bacillus subtillis* subsp. *subtilis* str. 168 (NP_389054); FabL from *Bacillus subtillis* subsp. *subtilis* str. 168 (NP_388745); FabI from *Acinetobacter* sp. ADP1 (YP_047630); FabI from *Marinobacter aquaeoli* VT8 (YP_958813); FabI from *Rhodococcus opacus* B4 (YP_002784194); FabH from *Acinetobacter* sp. ADP1 (YP_046731); FabH from *Marinobacter aquaeoli* VT8 (YP_958649); and FabH from *Rhodococcus opacus* B4 (YP_00278448) or combinations thereof.

The disclosure further contemplates a recombinant host cell having a genetically engineered polynucleotide sequence encoding an ACP polypeptide, wherein the recombinant host cell produces a fatty acid derivative composition at a higher titer, yield or productivity than a corresponding wild type host cell when cultured in a medium containing a carbon source under conditions effective to express the ACP polypeptide. In a related aspect, the genetically engineered polynucleotide sequence further encodes a polypeptide that has phosphopantetheinyl transferase (E.C. 2.7.8.7) activity. Herein, the genetically engineered polynucleotide sequence includes a sfp gene coding encoding a phosphopantetheinyl transferase (E.C. 2.7.8.7). In a related aspect, a genetically engineered polynucleotide sequence further encodes a polypeptide that has accABCD activity (E.C. 6.4.1.2). ACP can be in expressed in combination with accABCD and/or a phosphopantetheinyl transferase, wherein the combination of any of the expressed polypeptides further leads to increases in the titer, yield and/or productivity of the recombinant host cell when cultured under appropriate conditions. In another related aspect, ACP is derived from the same organism as a terminal pathway enzyme expressed in the recombinant host cell, wherein the terminal enzyme cleaves any acyl-ACP species that is part of the fatty acid biosynthetic pathway. The ACP is exogenous or endogenous to the host cell.

The disclosure further encompasses a recombinant host cell including a genetically engineered polynucleotide sequence including a transposon, wherein insertion of the transposon into a yjP gene affects a second gene flanking the yjP gene, wherein the second gene codes for a polynucleotide that is up- or down regulated, and wherein the up- or down regulated polynucleotide codes for a polypeptide that affects production of a fatty acid derivative composition when the host cell is cultured in a medium containing a carbon source under conditions effective to express the polypeptide. The yjP gene can be flanked by genes on either side. In a related aspect, the insertion of the transposon into the yjP gene results in inactivation of the yjP gene or a polynucleotide thereof, which affects one or more of the genes flanking the yijP gene, wherein the flanking gene or genes code for a polypeptide that affects production of a fatty acid derivative composition when the host cell is cultured in a medium containing a carbon source under conditions effective to express the polypeptide. In one related aspect, the flanking gene includes polynucleotides including, but not limited to, ppc, yjO, frwD, pflC, pflD or argE.

Another aspect of the disclosure provides a recombinant host cell including a genetically engineered polynucleotide sequence encoding a phosphoenolpyruvate carboxylase (ppc) polypeptide, wherein the recombinant host cell produces a fatty acid derivative composition at a higher titer, yield or productivity than a corresponding wild type host cell when cultured in a medium containing a carbon source under conditions effective to express the ppc polypeptide.

Still, another aspect of the disclosure provides a cell culture that includes any of the recombinant host cells presented herein (supra). The recombinant host cell is cultured in a medium such that the recombinant host cell produces fatty acid derivative compositions according to the genetic engineering methods presented herein (supra). In a related aspect, the fatty acid derivative compositions produced by the recombinant host cells of the present disclosure include, but are not limited to, fatty acids, fatty esters, fatty alcohols, fatty aldehydes, alkanes, terminal olefins, internal olefins, and ketones. In another related aspect, the fatty acid derivative is a C6, C8, C10, C12, C13, C14, C15, C16, C17, or C18 fatty acid derivative. In yet another related aspect, the fatty acid derivative is a C10:1, C12:1, C14:1, C16:1, or C18:1 unsaturated fatty acid derivative. In a further related aspect, the fatty acid derivative composition comprises one or more of C8, C10, C12, C14, C16, and C18 fatty acid derivatives. The fatty acid derivative compositions produced by the cell cultures containing the recombinant host cells of the present disclosure include fatty acids, fatty aldehydes, fatty alcohols, fatty esters, alkanes, terminal olefins, internal olefins, and ketones. The disclosure further encompasses fatty acid derivative compositions that include fatty acid derivatives having a double bond at position 7 in the carbon chain between C7 and C8 from the reduced end of the fatty alcohol; fatty acid derivative compositions including unsaturated fatty acid derivatives; fatty acid derivative compositions including saturated fatty acid derivatives; and fatty acid derivative compositions including branched chain fatty acid derivatives.

The disclosure further contemplates a cell culture containing any of the recombinant host cells presented herein, wherein the recombinant host cells have a titer that is at least about 5% greater than the titer of the corresponding wild type host cells when cultured under the same conditions as the recombinant host cells. Herein, the recombinant host cells have a titer of from about 1 g/L to about 250 g/L, and more specifically from about 90 g/L to about 120 g/L. In a related aspect, the recombinant host cells have a yield that is at least about 10% to about 40%. In one aspect, the recombinant host cells have a yield of about 25%. Still encompassed herein is a cell culture containing any one of the recombinant host cells presented herein, wherein the productivity of the cell culture ranges from about 0.7 mg/L/hr to about 3 g/L/hr or higher.

Another aspect of the disclosure provides methods of making a recombinant host cell, including genetically engineering the recombinant host cell such that the cell expresses a polypeptide sequence that is encoded by one or more polynucleotide sequences under specific culture conditions, wherein the polynucleotide sequence codes for one or more polypeptides that have a specific enzymatic activity.

BRIEF DESCRIPTION OF THE DRAWINGS

The present disclosure is best understood when read in conjunction with the accompanying figures, which serve to illustrate the preferred embodiments. It is understood, however, that the disclosure is not limited to the specific embodiments disclosed in the figures.

FIG. 1 presents an exemplary biosynthetic pathway for use in production of acyl CoA as a precursor to fatty acid derivatives in a recombinant microorganism. The cycle is initiated by condensation of malonyl-ACP and acetyl-CoA.

(FIG. 12A) and 37° C. (FIG. 12B).

DETAILED DESCRIPTION

General Overview

Figure 2:
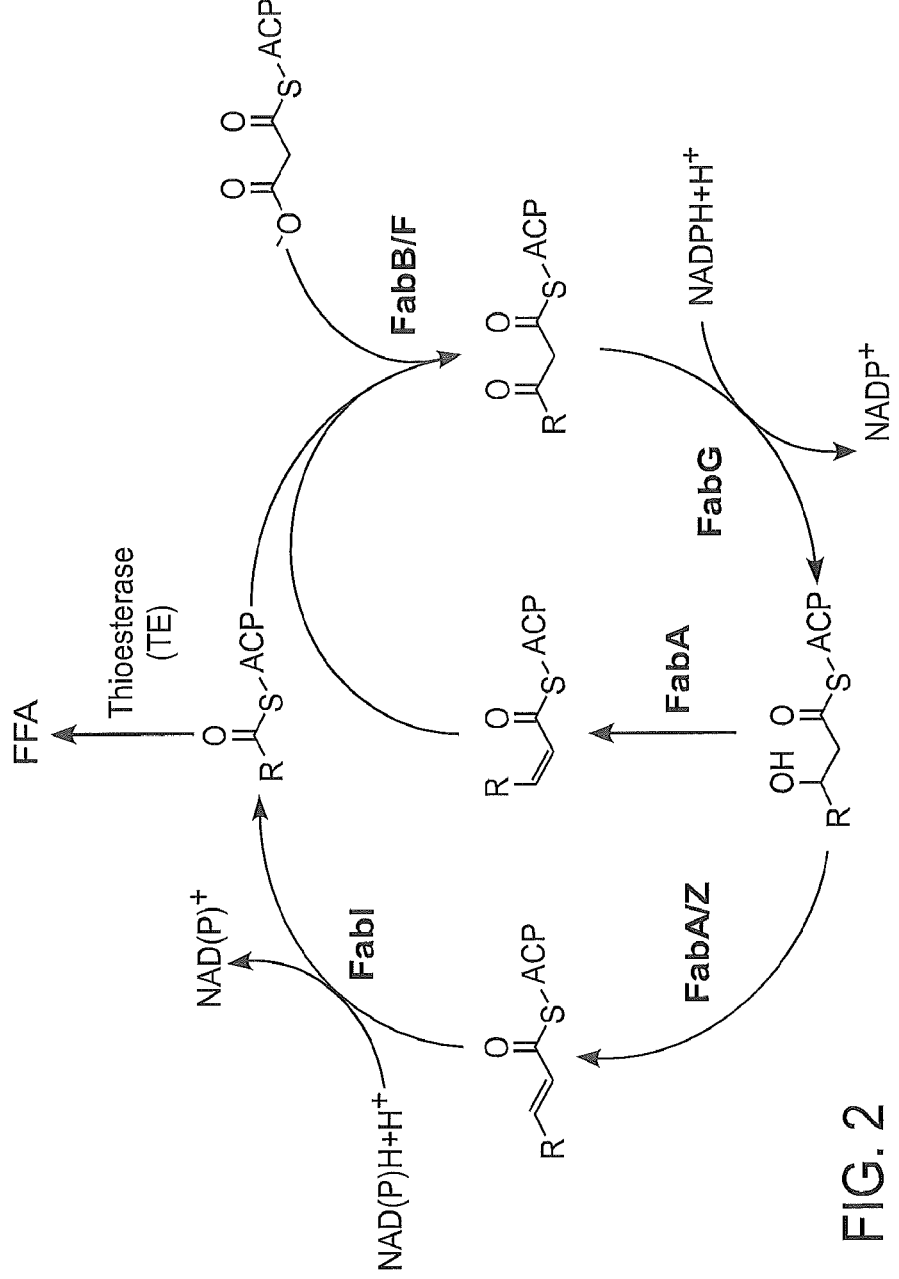
FIG. 2 presents an exemplary fatty acid biosynthetic cycle, where malonyl-ACP is produced by the transacylation of malonyl-CoA to malonyl-ACP (catalyzed by malonyl-CoA:ACP transacylase (fabD)); then β-ketoacyl-ACP synthase III (fabH) initiates condensation of malonyl-ACP with acetyl-CoA. Elongation cycles begin with the condensation of malonyl-ACP and an acyl-ACP catalyzed by β-ketoacyl-ACP synthase I (fabB) and β-ketoacyl-ACP synthase II (fabF) to produce a β-keto-acyl-ACP, then the β-keto-acyl-ACP is reduced by β-ketoacyl-ACP reductase (fabG) to produce a β-hydroxy-acyl-ACP, which is dehydrated to a trans-2-enoyl-acyl-ACP by β-hydroxyacyl-ACP dehydratase (fabA or fabZ). FabA can also isomerize trans-2-enoyl-acyl-ACP to cis-3-enoyl-acyl-ACP, which can bypass fabI and can used by fabB (typically for up to an aliphatic chain length of C16) to produce β-keto-acyl-ACP. The final step in each cycle is catalyzed by enoyl-ACP reductase (fabI) that converts trans-2-enoyl-acyl-ACP to acyl-ACP. In the methods described herein, termination of fatty acid synthesis occurs by thioesterase removal of the acyl group from acyl-ACP to release free fatty acids (FFA). Thioesterases (e.g., tesA) hydrolyze thioester bonds, which occur between acyl chains and ACP through sulfydryl bonds.

The disclosure is based, at least in part, on the discovery that modification of various aspects of the fatty acid biosynthetic pathway in a recombinant host cell facilitates enhanced production of fatty acid derivatives by the host cell. The disclosure relates to compositions of fatty acid derivatives having desired characteristics and methods for producing the same. Further, the disclosure relates to recombinant host cells (e.g., microorganisms), cultures of recombinant host cells, methods of making and using recombinant host cells, for example, use of cultured recombinant host cells in the fermentative production of fatty acid derivatives having desired characteristics.

More specifically, the production of a desired fatty acid derivative composition (e.g., acyl-CoA, fatty acids, fatty aldehydes, short and long chain alcohols, hydrocarbons, fatty alcohols, esters (e.g., waxes, fatty acid esters, or fatty esters), terminal olefins, internal olefins, and ketones is enhanced by modifying the expression of one or more genes involved in a biosynthetic pathway for fatty acid, fatty ester, alkane, alkene, olefin, or fatty alcohol, production, degradation and/or secretion. The disclosure provides recombinant host cells which have been engineered to provide enhanced fatty acid biosynthesis relative to non-engineered or native host cells (e.g., wild type host cells that function as control cells), which is accomplished, for example, through strain improvements. As such, the disclosure identifies polynucleotides useful in the recombinant host cells, methods, and compositions of the disclosure. It will be generally recognized that absolute sequence identity to such polynucleotides is not necessary. For example, changes in a particular polynucleotide sequence can be made and the encoded polypeptide screened for activity. Such changes typically comprise conservative mutations and silent mutations (e.g., codon optimization). Genetically engineered or modified polynucleotides and encoded variant polypeptides can be screened for a desired function, including but not limited to, increased catalytic activity, increased stability, or decreased inhibition (e.g., decreased feedback inhibition), using methods known in the art.

The disclosure identifies enzymatic activities involved in various steps (i.e., reactions) of the fatty acid biosynthetic pathways described herein according to Enzyme Classification (EC) number, and provides exemplary polypeptides (e.g., enzymes) categorized by such EC numbers, and exemplary polynucleotides encoding such polypeptides. Such exemplary polypeptides and polynucleotides, which are identified herein by Accession Numbers and/or Sequence Identifier Numbers (SEQ ID NOs), are useful for engineering fatty acid pathways in parental host cells to obtain the recombinant host cells described herein. The polypeptides and polynucleotides described herein are exemplary and non-limiting. The sequences of homologues of exemplary polypeptides described herein are available to those of skill in the art through various databases (e.g., rhw Entrez databases provided by the National Center for Biotechnology Information (NCBI), the ExPasy databases provided by the Swiss Institute of Bioinformatics, the BRENDA database provided by the Technical University of Braunschweig, and the KEGG database provided by the Bioinformatics Center of Kyoto University and University of Tokyo, all which are available on the World Wide Web).

Definitions

As used in this specification and the appended claims, the singular forms "a," "an" and "the" include plural referents unless the context clearly dictates otherwise. Thus, for example, reference to "a recombinant host cell" includes two or more such recombinant host cells, reference to "a fatty alcohol" includes one or more fatty alcohols, or mixtures of fatty alcohols, reference to "a nucleic acid coding sequence" includes one or more nucleic acid coding sequences, reference to "an enzyme" includes one or more enzymes, and the like.

Accession Numbers: Sequence Accession numbers throughout this description were obtained from databases provided by the NCBI (National Center for Biotechnology Information) maintained by the National Institutes of Health, U.S.A. (which are identified herein as "NCBI Accession Numbers" or alternatively as "GenBank Accession Numbers"), and from the UniProt Knowledgebase (UniProtKB) and Swiss-Prot databases provided by the Swiss Institute of Bioinformatics (which are identified herein as "UniProtKB Accession Numbers").

Enzyme Classification (EC) Numbers: EC numbers are established by the Nomenclature Committee of the International Union of Biochemistry and Molecular Biology (IUBMB), description of which is available on the IUBMB Enzyme Nomenclature website on the World Wide Web. EC numbers classify enzymes according to the reaction they catalyze.

As used herein, the term "nucleotide" refers to a monomeric unit of a polynucleotide that consists of a heterocyclic base, a sugar, and one or more phosphate groups. The naturally occurring bases (guanine, (G), adenine, (A), cytosine, (C), thymine, (T), and uracil (U)) are typically derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleic acids are typically linked via phosphate bonds to form nucleic acids or polynucleotides, though many other linkages are known in the art (e.g., phosphorothioates, boranophosphates, and the like).

As used herein, the term "polynucleotide" refers to a polymer of ribonucleotides (RNA) or deoxyribonucleotides (DNA), which can be single-stranded or double-stranded and which can contain non-natural or altered nucleotides. The terms "polynucleotide," "nucleic acid sequence," and "nucleotide sequence" are used interchangeably herein to refer to a polymeric form of nucleotides of any length, either RNA or DNA. These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to methylated and/or capped polynucleotides. The polynucleotide can be in any form, including but not limited to, plasmid, viral, chromosomal, EST, cDNA, mRNA, and rRNA.

As used herein, the terms "polypeptide" and "protein" are used interchangeably to refer to a polymer of amino acid residues. The term "recombinant polypeptide" refers to a polypeptide that is produced by recombinant techniques, wherein generally DNA or RNA encoding the expressed protein is inserted into a suitable expression vector that is in turn used to transform a host cell to produce the polypeptide.

As used herein, the terms "homolog," and "homologous" refer to a polynucleotide or a polypeptide comprising a sequence that is at least about 50% identical to the corresponding polynucleotide or polypeptide sequence. Preferably homologous polynucleotides or polypeptides have polynucleotide sequences or amino acid sequences that have at least about 80%, 81%, 82%, 83%, 84%, 85%, 86%, 87%, 88%, 89%, 90%, 91%, 92%, 93%, 94%, 95%, 96%, 97%, 98% or at least about 99% homology to the corresponding amino acid sequence or polynucleotide sequence. As used herein the terms sequence "homology" and sequence "identity" are used interchangeably.

One of ordinary skill in the art is well aware of methods to determine homology between two or more sequences. Briefly, calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a first sequence that is aligned for comparison purposes is at least about 30%, preferably at least about 40%, more preferably at least about 50%, even more preferably at least about 60%, and even more preferably at least about 70%, at least about 75%, at least about 80%, at least about 85%, at least about 90%, at least about 95%, or about 100% of the length of a second sequence. The amino acid residues or nucleotides at corresponding amino acid positions or nucleotide positions of the first and second sequences are then compared. When a position in the first sequence is occupied by the same amino acid residue or nucleotide as the corresponding position in the second sequence, then the molecules are identical at that position. The percent homology between the two sequences is a function of the number of identical positions shared by the sequences, taking into account the number of gaps and the length of each gap, that need to be introduced for optimal alignment of the two sequences.

The comparison of sequences and determination of percent homology between two sequences can be accomplished using a mathematical algorithm, such as BLAST (Altschul et al., J. Mol. Biol., 215(3): 403-410 (1990)). The percent homology between two amino acid sequences also can be determined using the Needleman and Wunsch algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6 (Needleman and Wunsch, J. Mol. Biol., 48: 444-453 (1970)). The percent homology between two nucleotide sequences also can be determined using the GAP program in the GCG software package, using a NWSgapdna.CMP matrix and a gap weight of 40, 50, 60, 70, or 80 and a length weight of 1, 2, 3, 4, 5, or 6. One of ordinary skill in the art can perform initial homology calculations and adjust the algorithm parameters accordingly. A preferred set of parameters (and the one that should be used if a practitioner is uncertain about which parameters should be applied to determine if a molecule is within a homology limitation of the claims) are a Blossum 62 scoring matrix with a gap penalty of 12, a gap extend penalty of 4, and a frameshift gap penalty of 5. Additional methods of sequence alignment are known in the biotechnology arts (see, e.g., Rosenberg, BMC Bioinformatics, 6: 278 (2005); Altschul, et al., FEBS J., 272(20): 5101-5109 (2005)).

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6. Aqueous and non-aqueous methods are described in that reference and either method can be used. Specific hybridization conditions referred to herein are as follows: 1) low stringency hybridization conditions—6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions—6×SSC at about 45° C., followed by one or more washes in 0.2×SSC, 0.1% SDS at 60° C.; 3) high stringency hybridization conditions—6×SSC at about 45° C., followed by one or more washes in 0.2.×SSC, 0.1% SDS at 65° C.; and 4) very high stringency hybridization conditions—0.5M sodium phosphate, 7% SDS at 65° C., followed by one or more washes at 0.2×SSC, 1% SDS at 65° C. Very high stringency conditions (4) are the preferred conditions unless otherwise specified.

An "endogenous" polypeptide refers to a polypeptide encoded by the genome of the host cell (e.g., parental microbial cell) from which the recombinant cell is engineered or derived.

An "exogenous" polypeptide refers to a polypeptide which is not encoded by the genome of the parental microbial cell. A variant (i.e., mutant) polypeptide is an example of an exogenous polypeptide.

The term "heterologous" generally means derived from a different species or derived from a different organism. As used herein it refers to a nucleotide sequence or a polypeptide sequence that is not naturally present in a particular organism. Heterologous expression means that a protein or polypeptide is experimentally added to a cell that does not normally express that protein. As such, heterologous refers to the fact that a transferred protein was initially derived from a different cell type or a different species then the recipient. For example, a polynucleotide sequence endogenous to a plant cell can be introduced into a bacterial host cell by recombinant methods, and the plant polynucleotide is then a heterologous polynucleotide in a recombinant bacterial host cell.

As used herein, the term "fragment" of a polypeptide refers to a shorter portion of a full-length polypeptide or protein ranging in size from four amino acid residues to the entire amino acid sequence minus one amino acid residue. In certain embodiments of the disclosure, a fragment refers to the entire amino acid sequence of a domain of a polypeptide or protein (e.g., a substrate binding domain or a catalytic domain).

As used herein, the term "mutagenesis" refers to a process by which the genetic information of an organism is changed in a stable manner. Mutagenesis of a protein coding nucleic acid sequence produces a mutant protein. Mutagenesis also refers to changes in non-coding nucleic acid sequences that result in modified protein activity.

As used herein, the term "gene" refers to nucleic acid sequences encoding either an RNA product or a protein product, as well as operably-linked nucleic acid sequences affecting the expression of the RNA or protein (e.g., such sequences include but are not limited to promoter or enhancer sequences) or operably-linked nucleic acid sequences encoding sequences that affect the expression of the RNA or protein (e.g., such sequences include but are not limited to ribosome binding sites or translational control sequences).

Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al., Science, 236: 1237-1245 (1987)). Exemplary expression control sequences are described in, for example, Goeddel, Gene Expression Technology: Methods in Enzymology, Vol. 185, Academic Press, San Diego, Calif. (1990).

In the methods of the disclosure, an expression control sequence is operably linked to a polynucleotide sequence. By "operably linked" is meant that a polynucleotide sequence and an expression control sequence(s) are connected in such a way as to permit gene expression when the appropriate molecules (e.g., transcriptional activator proteins) are bound to the expression control sequence(s). Operably linked promoters are located upstream of the selected polynucleotide sequence in terms of the direction of transcription and translation. Operably linked enhancers can be located upstream, within, or downstream of the selected polynucleotide.

As used herein, the term "vector" refers to a nucleic acid molecule capable of transporting another nucleic acid, i.e., a polynucleotide sequence, to which it has been linked. One type of useful vector is an episome (i.e., a nucleic acid capable of extra-chromosomal replication). Useful vectors are those capable of autonomous replication and/or expression of nucleic acids to which they are linked. Vectors capable of directing the expression of genes to which they are operatively linked are referred to herein as "expression vectors." In general, expression vectors of utility in recombinant DNA techniques are often in the form of "plasmids," which refer generally to circular double stranded DNA loops that, in their vector form, are not bound to the chromosome. The terms "plasmid" and "vector" are used interchangeably herein, in as much as a plasmid is the most commonly used form of vector. However, also included are such other forms of expression vectors that serve equivalent functions and that become known in the art subsequently hereto. In some embodiments, a recombinant vector further comprises a promoter operably linked to the polynucleotide sequence. In some embodiments, the promoter is a developmentally-regulated, an organelle-specific, a tissue-specific, an inducible, a constitutive, or a cell-specific promoter. The recombinant vector typically comprises at least one sequence including (a) an expression control sequence operatively coupled to the polynucleotide sequence; (b) a selection marker operatively coupled to the polynucleotide sequence; (c) a marker sequence operatively coupled to the polynucleotide sequence; (d) a purification moiety operatively coupled to the polynucleotide sequence; (e) a secretion sequence operatively coupled to the polynucleotide sequence; and (f) a targeting sequence operatively coupled to the polynucleotide sequence. In certain embodiments, the nucleotide sequence is stably incorporated into the genomic DNA of the host cell, and the expression of the nucleotide sequence is under the control of a regulated promoter region. The expression vectors described herein include a polynucleotide sequence described herein in a form suitable for expression of the polynucleotide sequence in a host cell. It will be appreciated by those skilled in the art that the design of the expression vector can depend on such factors as the choice of the host cell to be transformed, the level of expression of polypeptide desired, etc. The expression vectors described herein can be introduced into host cells to produce polypeptides, including fusion polypeptides, encoded by the polynucleotide sequences as described herein.

Expression of genes encoding polypeptides in prokaryotes, for example, *E. coli*, is most often carried out with vectors containing constitutive or inducible promoters directing the expression of either fusion or non-fusion polypeptides. Fusion vectors add a number of amino acids to a polypeptide encoded therein, usually to the amino- or carboxy-terminus of the recombinant polypeptide. Such fusion vectors typically serve one or more of the following three purposes: (1) to increase expression of the recombinant polypeptide; (2) to increase the solubility of the recombinant polypeptide; and (3) to aid in the purification of the recombinant polypeptide by acting as a ligand in affinity purification. Often, in fusion expression vectors, a proteolytic cleavage site is introduced at the junction of the fusion moiety and the recombinant polypeptide. This enables separation of the recombinant polypeptide from the fusion moiety after purification of the fusion polypeptide. In certain embodiments, a polynucleotide sequence of the disclosure is operably linked to a promoter derived from bacteriophage T5.

In certain embodiments, the host cell is a yeast cell, and the expression vector is a yeast expression vector. Examples of vectors for expression in yeast *S. cerevisiae* include pYepSec1 (Baldari et al., EMBO J., 6: 229-234 (1987)), pMFa (Kurjan et al., Cell, 30: 933-943 (1982)), pJRY88 (Schultz et al., Gene, 54: 113-123 (1987)), pYES2 (Invitrogen Corp., San Diego, CA), and picZ (Invitrogen Corp., San Diego, CA).

In other embodiments, the host cell is an insect cell, and the expression vector is a baculovirus expression vector. Baculovirus vectors available for expression of proteins in cultured insect cells (e.g., Sf9 cells) include, for example, the pAc series (Smith et al., Mol. Cell Biol., 3: 2156-2165 (1983)) and the pVL series (Lucklow et al., Virology, 170: 31-39 (1989)).

In yet another embodiment, the polynucleotide sequences described herein can be expressed in mammalian cells using a mammalian expression vector. Other suitable expression systems for both prokaryotic and eukaryotic cells are well known in the art; see, e.g., Sambrook et al., "Molecular Cloning: A Laboratory Manual," second edition, Cold Spring Harbor Laboratory, (1989).

The term "corresponding wild type host cell" as referred to herein, means a cell that functions as a control cell. For example, if a polypeptide in a recombinant host cell is up-regulated, then the same polypeptide would exist at a lower level in the control cell. Conversely, if a polypeptide in a recombinant host cell is down-regulated, then the same polypeptide would exist at a higher level in the control cell. Furthermore, the "recombinant or engineered host cell" is a microorganism used to produce one or more of fatty acid derivatives including, for example, acyl-CoA, fatty acids, fatty aldehydes, short and long chain alcohols, hydrocarbons, fatty alcohols, esters (e.g., waxes, fatty acid esters, or fatty esters), terminal olefins, internal olefins, and ketones. In some embodiments, the recombinant host cell comprises one or more polynucleotides, each polynucleotide encoding a polypeptide having fatty acid biosynthetic enzyme activity.

As used herein "acyl-CoA" refers to an acyl thioester formed between the carbonyl carbon of alkyl chain and the sulfhydryl group of the 4'-phosphopantethionyl moiety of coenzyme A (CoA), which has the formula R—C(O)S—CoA, where R is any alkyl group having at least 4 carbon atoms.

As used herein "acyl-ACP" refers to an acyl thioester formed between the carbonyl carbon of alkyl chain and the sulfhydryl group of the phosphopantetheinyl moiety of an acyl carrier protein (ACP). The phosphopantetheinyl moiety is post-translationally attached to a conserved serine residue on the ACP by the action of holo-acyl carrier protein synthase (ACPS), a phosphopantetheinyl transferase. In some embodiments an acyl-ACP is an intermediate in the synthesis of fully saturated acyl-ACPs. In other embodiments an acyl-ACP is an intermediate in the synthesis of unsaturated acyl-ACPs. In some embodiments, the carbon chain will have about 5, 6, 7, 8, 9, 10, 11, 12, 13, 14, 15, 16, 17, 18, 19, 20, 21, 22, 23, 24, 25, or 26 carbons. Each of these acyl-ACPs are substrates for enzymes that convert them to fatty acid derivatives.

As used herein, the term "fatty acid derivative" means a "fatty acid" or a "fatty acid derivative", which may be referred to as a "fatty acid or derivative thereof". The term "fatty acid" means a carboxylic acid having the formula RCOOH. R represents an aliphatic group, preferably an alkyl group. R can comprise between about 4 and about 22 carbon atoms. Fatty acids can be saturated, monounsaturated, or polyunsaturated. A "fatty acid derivative" is a product made in part from the fatty acid biosynthetic pathway of the production host organism. "Fatty acid derivatives" includes products made in part from acyl-ACP or acyl-ACP derivatives. Exemplary fatty acid derivatives include, for example, acyl-CoA, fatty acids, fatty aldehydes, short and long chain alcohols, fatty alcohols, hydrocarbons, esters (e.g., waxes, fatty acid esters, or fatty esters), terminal olefins, internal olefins, and ketones.

A "fatty acid derivative composition" as referred to herein is produced by a recombinant host cell and typically comprises a mixture of fatty acid derivative. In some cases, the mixture includes more than one type of product (e.g., fatty acids and fatty alcohols, fatty acids and fatty acid esters or alkanes and olefins). In other cases, the fatty acid derivative compositions may comprise, for example, a mixture of fatty alcohols (or another fatty acid derivative) with various chain lengths and saturation or branching characteristics. In still other cases, the fatty acid derivative composition comprises a mixture of both more than one type of product and products with various chain lengths and saturation or branching characteristics.

As used herein, the term "fatty acid biosynthetic pathway" means a biosynthetic pathway that produces fatty acids and derivatives thereof. The fatty acid biosynthetic pathway may include additional enzymes or polypeptides with enzymatic activities besides the ones discussed herein to produce fatty acid derivatives having desired characteristics.

As used herein, "fatty aldehyde" means an aldehyde having the formula RCHO characterized by a carbonyl group (C=O). In some embodiments, the fatty aldehyde is any aldehyde made from a fatty alcohol. In certain embodiments, the R group is at least 5, at least 6, at least 7, at least 8, at least 9, at least 10, at least 11, at least 12, at least 13, at least 14, at least 15, at least 16, at least 17, at least 18, or at least 19, carbons in length. Alternatively, or in addition, the R group is 20 or less, 19 or less, 18 or less, 17 or less, 16 or less, 15 or less, 14 or less, 13 or less, 12 or less, 11 or less, 10 or less, 9 or less, 8 or less, 7 or less, or 6 or less carbons in length. Thus, the R group can have an R group bounded by any two of the above endpoints. For example, the R group can be 6-16 carbons in length, 10-14 carbons in length, or 12-18 carbons in length. In some embodiments, the fatty aldehyde is a C6, C7, C8, C9, C10, C11, C12, C13, C14, C15, C16, C17, C18, C19, C20, C21, C22, C23, C24, C25, or a C26 fatty aldehyde. In certain embodiments, the fatty aldehyde is a C6, C7, C8, C9, C10, C11, C12, C13, C14, C15, C16, C17, or C18 fatty aldehyde.

As used herein, "fatty alcohol" means an alcohol having the formula ROH. In some embodiments, the R group is at least 5, at least 6, at least 7, at least 8, at least 9, at least 10, at least 11, at least 12, at least 13, at least 14, at least 15, at least 16, at least 17, at least 18, or at least 19, carbons in length. Alternatively, or in addition, the R group is 20 or less, 19 or less, 18 or less, 17 or less, 16 or less, 15 or less, 14 or less, 13 or less, 12 or less, 11 or less, 10 or less, 9 or less, 8 or less, 7 or less, or 6 or less carbons in length. Thus, the R group can have an R group bounded by any two of the above endpoints. For example, the R group can be 6-16 carbons in length, 10-14 carbons in length, or 12-18 carbons in length. In some embodiments, the fatty alcohol is a C6, C7, C8, C9, C10, C11, C12, C13, C14, C15, C16, C17, C18, C19, C20, C21, C22, C23, C24, C25, or a C26 fatty alcohol. In certain embodiments, the fatty alcohol is a C6, C7, C8, C9, C10, C11, C12, C13, C14, C15, C16, C17, or C18 fatty alcohol.

The R group of a fatty acid derivative, for example a fatty alcohol, can be a straight chain or a branched chain. Branched chains may have more than one point of branching and may include cyclic branches. In some embodiments, the branched fatty acid, branched fatty aldehyde, or branched fatty alcohol is a C6, C7, C8, C9, C10, C11, C12, C13, C14, C15, C16, C17, C18, C19, C20, C21, C22, C23, C24, C25, or a C26 branched fatty acid, branched fatty aldehyde, or branched fatty alcohol. In particular embodiments, the branched fatty acid, branched fatty aldehyde, or branched fatty alcohol is a C6, C7, C8, C9, C10, C11, C12, C13, C14, C15, C16, C17, or C18 branched fatty acid, branched fatty aldehyde, or branched fatty alcohol. In certain embodiments, the hydroxyl group of the branched fatty acid, branched fatty aldehyde, or branched fatty alcohol is in the primary (C1) position.

In certain embodiments, the branched fatty acid derivative is an iso-fatty acid derivative, for example an iso-fatty aldehyde, an iso-fatty alcohol, or an antesio-fatty acid derivative, an anteiso-fatty aldehyde, or an anteiso-fatty alcohol. In exemplary embodiments, the branched fatty acid derivative is selected from iso-C7:0, iso-C8:0, iso-C9:0, iso-C10:0, iso-C11:0, iso-C12:0, iso-C13:0, iso-C14:0, iso-C15:0, iso-C16:0, iso-C17:0, iso-C18:0, iso-C19:0, anteiso-C7:0, anteiso-C8:0, anteiso-C9:0, anteiso-C10:0, anteiso-C11:0,anteiso-C12:0, anteiso-C13:0, anteiso-C14:0, anteiso-C15:0, anteiso-C16:0, anteiso-C17:0, anteiso-C18:0, and an anteiso-C19:0 branched fatty alcohol.

The R group of a branched or unbranched fatty acid derivative can be saturated or unsaturated. If unsaturated, the R group can have one or more than one point of unsaturation. In some embodiments, the unsaturated fatty acid derivative is a monounsaturated fatty acid derivative. In certain embodiments, the unsaturated fatty acid derivative is a C6:1, C7:1, C8:1, C9:1, C10:1, C11:1, C12:1, C13:1, C14:1, C15:1, C16:1, C17:1, C18:1, C19:1, C20:1, C21:1, C22:1, C23:1, C24:1, C25:1, or a C26:1 unsaturated fatty acid derivative. In certain embodiments, the unsaturated fatty acid derivative is a C10:1, C12:1, C14:1, C16:1, or C18:1 unsaturated fatty acid derivative. In other embodiments, the unsaturated fatty acid derivative is unsaturated at the omega-7 position. In certain embodiments, the unsaturated fatty acid derivative comprises a cis double bond.

As used herein, the term "clone" typically refers to a cell or group of cells descended from and essentially genetically identical to a single common ancestor, for example, the bacteria of a cloned bacterial colony arose from a single bacterial cell.

As used herein, the term "culture" typical refers to a liquid media comprising viable cells. In one embodiment, a culture comprises cells reproducing in a predetermined culture media under controlled conditions, for example, a culture of recombinant host cells grown in liquid media comprising a selected carbon source and nitrogen. "Culturing" or "cultivation" refers to growing a population of recombinant host cells under suitable conditions in a liquid or solid medium. In particular embodiments, culturing refers to the fermentative bioconversion of a substrate to an end-product. Culturing media are well known and individual components of such culture media are available from commercial sources, e.g., under the Difco™ and BBL™ trademarks. In one non-limiting example, the aqueous nutrient medium is a "rich medium" comprising complex sources of nitrogen, salts, and carbon, such as YP medium, comprising 10 g/L of peptone and 10 g/L yeast extract of such a medium. The host cell of a culture can be additionally engineered to assimilate carbon efficiently and use cellulosic materials as carbon sources according to methods described in U.S. Pat. Nos. 5,000,000; 5,028,539; 5,424,202; 5,482,846; 5,602,030; WO 2010127318. In addition, in some embodiments the host cell is engineered to express an invertase so that sucrose can be used as a carbon source.

As used herein, the term "under conditions effective to express a genetically engineered polynucleotide sequence" means any condition that allows a host cell to produce a desired fatty acid derivative. Suitable conditions include, for example, fermentation conditions.

As used herein, "modified" or an "altered level of" activity of a protein, for example an enzyme, in a recombinant host cell refers to a difference in one or more characteristics in the activity determined relative to the parent or native host cell. Typically differences in activity are determined between a recombinant host cell, having modified activity, and the corresponding wild-type host cell (e.g., comparison of a culture of a recombinant host cell relative to the corresponding wild-type host cell). Modified activities can be the result of, for example, modified amounts of protein expressed by a recombinant host cell (e.g., as the result of increased or decreased number of copies of DNA sequences encoding the protein, increased or decreased number of mRNA transcripts encoding the protein, and/or increased or decreased amounts of protein translation of the protein from mRNA); changes in the structure of the protein (e.g., changes to the primary structure, such as, changes to the protein's coding sequence that result in changes in substrate specificity, changes in observed kinetic parameters); and changes in protein stability (e.g., increased or decreased degradation of the protein). In some embodiments, the polypeptide is a mutant or a variant of any of the polypeptides described herein. In certain instances, the coding sequences for the polypeptides described herein are codon optimized for expression in a particular host cell. For example, for expression in *E. coli*, one or more codons can be optimized as described in, e.g., Grosjean et al., Gene 18:199-209 (1982).

The term "regulatory sequences" as used herein typically refers to a sequence of bases in DNA, operably-linked to DNA sequences encoding a protein that ultimately controls the expression of the protein. Examples of regulatory sequences include, but are not limited to, RNA promoter sequences, transcription factor binding sequences, transcription termination sequences, modulators of transcription (such as enhancer elements), nucleotide sequences that affect RNA stability, and translational regulatory sequences (such as, ribosome binding sites (e.g., Shine-Dalgarno sequences in prokaryotes or Kozak sequences in eukaryotes), initiation codons, termination codons).

The terms "altered level of expression" and "modified level of expression" are used interchangeably and mean that a polynucleotide, polypeptide, or hydrocarbon is present in a different concentration in an engineered host cell as compared to its concentration in a corresponding wild-type cell under the same conditions.

As used herein, the term "titer" refers to the quantity of fatty acid derivative produced per unit volume of host cell culture. In any aspect of the compositions and methods described herein, a fatty acid derivative is produced at a titer of about 25 mg/L, about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, about 300 mg/L, about 325 mg/L, about 350 mg/L, about 375 mg/L, about 400 mg/L, about 425 mg/L, about 450 mg/L, about 475 mg/L, about 500 mg/L, about 525 mg/L, about 550 mg/L, about 575 mg/L, about 600 mg/L, about 625 mg/L, about 650 mg/L, about 675 mg/L, about 700 mg/L, about 725 mg/L, about 750 mg/L, about 775 mg/L, about 800 mg/L, about 825 mg/L, about 850 mg/L, about 875 mg/L, about 900 mg/L, about 925 mg/L, about 950 mg/L, about 975 mg/L, about 1000 mg/L, about 1050 mg/L, about 1075 mg/L, about 1100 mg/L, about 1125 mg/L, about 1150 mg/L, about 1175 mg/L, about 1200 mg/L, about 1225 mg/L, about 1250 mg/L, about 1275 mg/L, about 1300 mg/L, about 1325 mg/L, about 1350 mg/L, about 1375 mg/L, about 1400 mg/L, about 1425 mg/L, about 1450 mg/L, about 1475 mg/L, about 1500 mg/L, about 1525 mg/L, about 1550 mg/L, about 1575 mg/L, about 1600 mg/L, about 1625 mg/L, about 1650 mg/L, about 1675 mg/L, about 1700 mg/L, about 1725 mg/L, about 1750 mg/L, about 1775 mg/L, about 1800 mg/L, about 1825 mg/L, about 1850 mg/L, about 1875 mg/L, about 1900 mg/L, about 1925 mg/L, about 1950 mg/L, about 1975 mg/L, about 2000 mg/L (2 g/L), 3 g/L, 5 g/L, 10 g/L, 20 g/L, 30 g/L, 40 g/L, 50 g/L, 60 g/L, 70 g/L, 80 g/L, 90 g/L, 100 g/L or a range bounded by any two of the foregoing values. In other embodiments, a fatty acid derivative is produced at a titer of more than 100 g/L, more than 200 g/L, more than 300 g/L, or higher, such as 500 g/L, 700 g/L, 1000 g/L, 1200 g/L, 1500 g/L, or 2000 g/L. The preferred titer of fatty acid derivative produced by a recombinant host cell according to the methods of the disclosure is from 5 g/L to 200 g/L, 10 g/L to 150 g/L, 20 g/L to 120 g/L and 30 g/L to 100 g/L. In one embodiment, the titer of fatty acid derivative produced by a recombinant host cell according to the methods of the disclosure is about 1 g/L to about 250 g/L and more particularly, 90 g/L to about 120 g/L. The titer may refer to a particular fatty acid derivative or a combination of fatty acid derivatives produced by a given recombinant host cell culture.

As used herein, the "yield of fatty acid derivative produced by a host cell" refers to the efficiency by which an input carbon source is converted to product (i.e., fatty alcohol or fatty aldehyde) in a host cell. Host cells engineered to produce fatty acid derivatives according to the methods of the disclosure have a yield of at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30% or a range bounded by any two of the foregoing values. In other embodiments, a fatty acid derivative or derivatives is produced at a yield of more than 30%, 40%, 50%, 60%, 70%, 80%, 90% or more. Alternatively, or in addition, the yield is about 30% or less, about 27% or less, about 25% or less, or about 22% or less. Thus, the yield can be bounded by any two of the above endpoints. For example, the yield of a fatty acid derivative or derivatives produced by the recombinant host cell according to the methods of the disclosure can be 5% to 15%, 10% to 25%, 10% to 22%, 15% to 27%, 18% to 22%, 20% to 28%, or 20% to 30%. In a particular embodiment, the yield of a fatty acid derivative or derivatives produced by the recombinant host cell is about 10% to about 40%. In another particular embodiment, the yield of a fatty acid derivative or derivatives produced by the recombinant host cell is about 25%. The yield may refer to a particular fatty acid derivative or a combination of fatty acid derivatives produced by a given recombinant host cell culture.

As used herein, the term "productivity" refers to the quantity of a fatty acid derivative or derivatives produced per unit volume of host cell culture per unit time. In any aspect of the compositions and methods described herein, the productivity of a fatty acid derivative or derivatives produced by a recombinant host cell is at least 100 mg/L/hour, at least 200 mg/L/hour, at least 300 mg/L/hour, at least 400 mg/L/hour, at least 500 mg/L/hour, at least 600 mg/L/hour, at least 700 mg/L/hour, at least 800 mg/L/hour, at least 900 mg/L/hour, at least 1000 mg/L/hour, at least 1100 mg/L/hour, at least 1200 mg/L/hour, at least 1300 mg/L/hour, at least 1400 mg/L/hour, at least 1500 mg/L/hour, at least 1600 mg/L/hour, at least 1700 mg/L/hour, at least 1800 mg/L/hour, at least 1900 mg/L/hour, at least 2000 mg/L/hour, at least 2100 mg/L/hour, at least 2200 mg/L/hour, at least 2300 mg/L/hour, at least 2400 mg/L/hour, or at least 2500 mg/L/hour. For example, the productivity of a fatty acid derivative or derivatives produced by a recombinant host cell according to the methods of the may be from 500 mg/L/hour to 2500 mg/L/hour, or from 700 mg/L/hour to 2000 mg/L/hour. In one particular embodiment, the yield is about 0.7 mg/L/h to about 3 g/L/h. The productivity may refer to a particular fatty acid derivative or a combination of fatty acid derivatives produced by a given recombinant host cell culture.

As used herein, the term "total fatty species" and "total fatty acid product" may be used interchangeably herein with reference to the amount of fatty alcohols, fatty aldehydes and fatty acids, as evaluated by GC-FID as described in International Patent Application Publication WO2008/119082. The same terms may be used to mean fatty esters and free fatty acids when referring to a fatty ester analysis.

As used herein, the term "glucose utilization rate" means the amount of glucose used by the culture per unit time, reported as grams/liter/hour (g/L/hr). As used herein, the term "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, and gases (e.g., CO and $CO_2$). Exemplary carbon sources include, but are not limited to, monosaccharides, such as glucose, fructose, mannose, galactose, xylose, and arabinose; oligosaccharides, such as fructo-oligosaccharide and galacto-oligosaccharide; polysaccharides such as starch, cellulose, pectin, and xylan; disaccharides, such as sucrose, maltose, cellobiose, and turanose; cellulosic material and variants such as hemicelluloses, methyl cellulose and sodium carboxymethyl cellulose; saturated or unsaturated fatty acids, succinate, lactate, and acetate; alcohols, such as ethanol, methanol, and glycerol, or mixtures thereof. The carbon source can also be a product of photosynthesis, such as glucose. In certain preferred embodiments, the carbon source is biomass. In other preferred embodiments, the carbon source is glucose. In other preferred embodiments the carbon source is sucrose.

As used herein, the term "biomass" refers to any biological material from which a carbon source is derived. In some embodiments, a biomass is processed into a carbon source, which is suitable for bioconversion. In other embodiments, the biomass does not require further processing into a carbon source. The carbon source can be converted into a biofuel. An exemplary source of biomass is plant matter or vegetation, such as corn, sugar cane, or switchgrass. Another exemplary source of biomass is metabolic waste products, such as animal matter (e.g., cow manure). Further exemplary sources of biomass include algae and other marine plants. Biomass also includes waste products from industry, agriculture, forestry, and households, including, but not limited to, fermentation waste, ensilage, straw, lumber, sewage, garbage, cellulosic urban waste, and food leftovers. The term "biomass" also refers to sources of carbon, such as carbohydrates (e.g., monosaccharides, disaccharides, or polysaccharides).

As used herein, the term "isolated," with respect to products (such as fatty acids and derivatives thereof) refers to products that are separated from cellular components, cell culture media, or chemical or synthetic precursors. The fatty acids and derivatives thereof produced by the methods described herein can be relatively immiscible in the fermentation broth, as well as in the cytoplasm. Therefore, the fatty acids and derivatives thereof can collect in an organic phase either intracellularly or extracellularly.

As used herein, the terms "purify," "purified," or "purification" mean the removal or isolation of a molecule from its environment by, for example, isolation or separation. "Substantially purified" molecules are at least about 60% free (e.g., at least about 70% free, at least about 75% free, at least about 85% free, at least about 90% free, at least about 95% free, at least about 97% free, at least about 99% free) from other components with which they are associated. As used herein, these terms also refer to the removal of contaminants from a sample. For example, the removal of contaminants can result in an increase in the percentage of fatty acid derivatives in a sample. For example, when a fatty acid derivative is produced in a recombinant host cell, the fatty acid derivative can be purified by the removal of host cell proteins. After purification, the percentage of fatty acid derivative in the sample is increased. The terms "purify," "purified," and "purification" are relative terms which do not require absolute purity. Thus, for example, when a fatty acid derivative is produced in recombinant host cells, a purified fatty acid derivative is a fatty acid derivative that is substantially separated from other cellular components (e.g., nucleic acids, polypeptides, lipids, carbohydrates, or other hydrocarbons).

Strain Improvements

In order generate a high titer, yield, and/or productivity of fatty acid derivatives, a number of modifications were made to the production host cells. FadR is a key regulatory factor involved in fatty acid degradation and fatty acid biosynthetic pathways (Cronan et al., Mol. Microbiol., 29(4): 937-943 (1998)). The *E. coli* ACS enzyme FadD and the fatty acid transport protein FadL are components of a fatty acid uptake system. FadL mediates transport of fatty acids into the bacterial cell, and FadD mediates formation of acyl-CoA esters. When no other carbon source is available, exogenous fatty acids are taken up by bacteria and converted to acyl-CoA esters, which can bind to the transcription factor FadR and depress the expression of the fad genes that encode proteins responsible for fatty acid transport (FadL), activation (FadD), and β-oxidation (FadA, FadB, FadE, and FadH). When alternative sources of carbon are available, bacteria synthesize fatty acids as acyl-ACPs, which are used for phospholipid synthesis, but are not substrates for β-oxidation. Thus, acyl-CoA and acyl-ACP are both independent sources of fatty acids that can result in different end-products (Caviglia et al., *J. Biol. Chem.*, 279(12): 1163-1169 (2004)).

Figure 1:
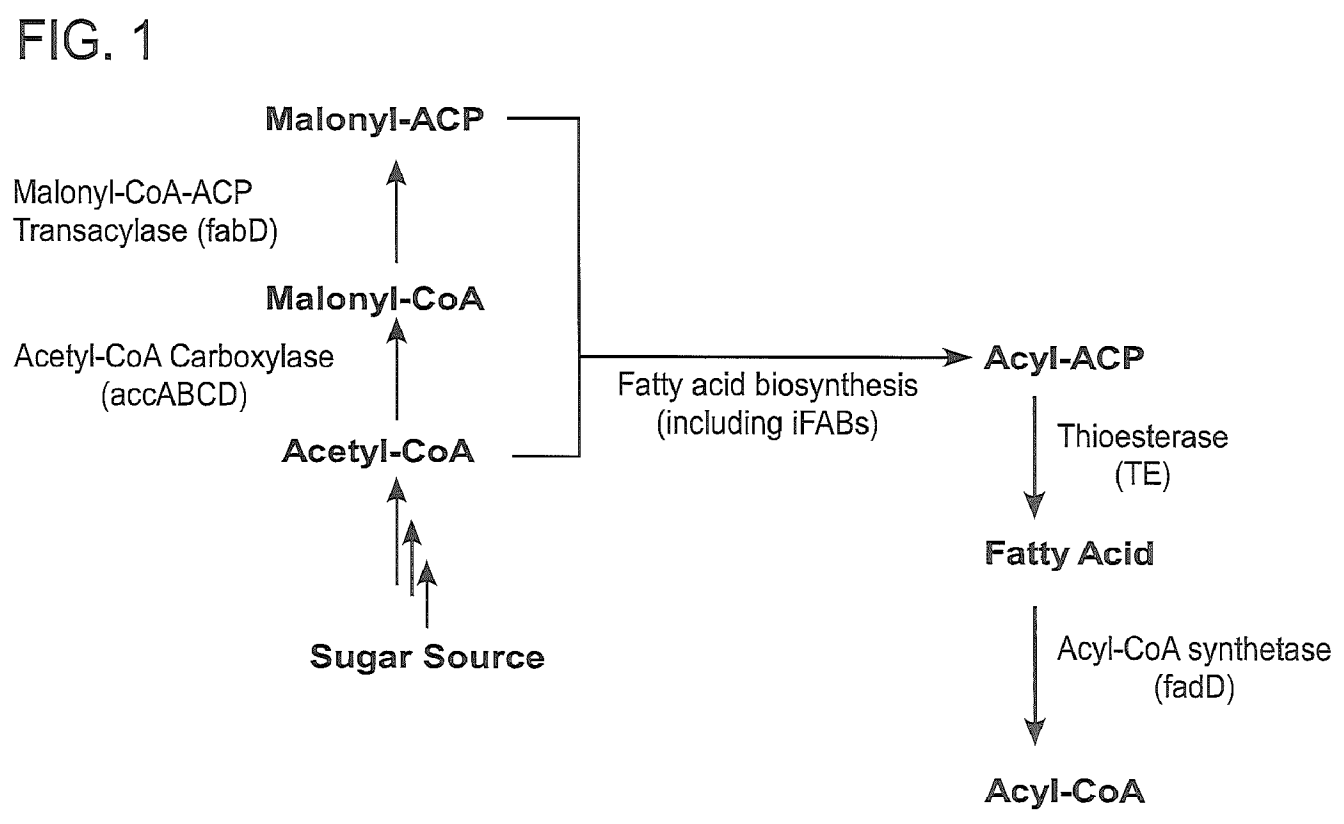

There are conflicting speculations in the art as to the factors that can limit fatty acid biosynthesis in host cells, such as *E. coli*. One suggestion is that a limitation of the main precursors for fatty acid biosynthesis, for example, acetyl-CoA and malonyl-CoA can result in decreased synthesis of fatty acid derivatives. One approach to increasing the flux through fatty acid biosynthesis is to manipulate various enzymes in the pathway (see FIGS. 1 and 2). Example 3 describes studies which show construction of fab operons that encode enzymes in the biosynthetic pathway for conversion of malonyl-CoA into acyl-ACPs and integration into the chromosome of an *E. coli* host cell. Without wanting to be bound by theory, this may increase the flux of fatty acid biosynthesis. The supply of acyl-ACPs from acetyl-CoA via the acetyl-CoA carboxylase (acc) complex and fatty acid biosynthetic (fab) pathway is another step that may limit the rate of fatty acid derivative production (see FIG. 3). Example 2 shows the effect of overexpression of an optimized version of *E. coli Corynebacterium glutamicum* accABCD (±birA) demonstrated that such genetic modifications can lead to increased production of acetyl-coA and malonyl-CoA in *E. coli*.

In another approach, mutations in the rph and ilvG genes in the *E. coli* host cell were shown to result in higher free fatty acid (FFA) production, which translated into higher production of fatty alcohol as shown in Example 4. In still another approach, transposon mutagenesis and high-throughput screening was carried out to find beneficial mutations that increase the titer or yield. As shown in Example 5, a transposon insertion in the yijP gene can improve the fatty alcohol yield in shake flask and fed-batch fermentations.

Generation of Fatty Acid Derivatives by Recombinant Host Cells

Figure 5:
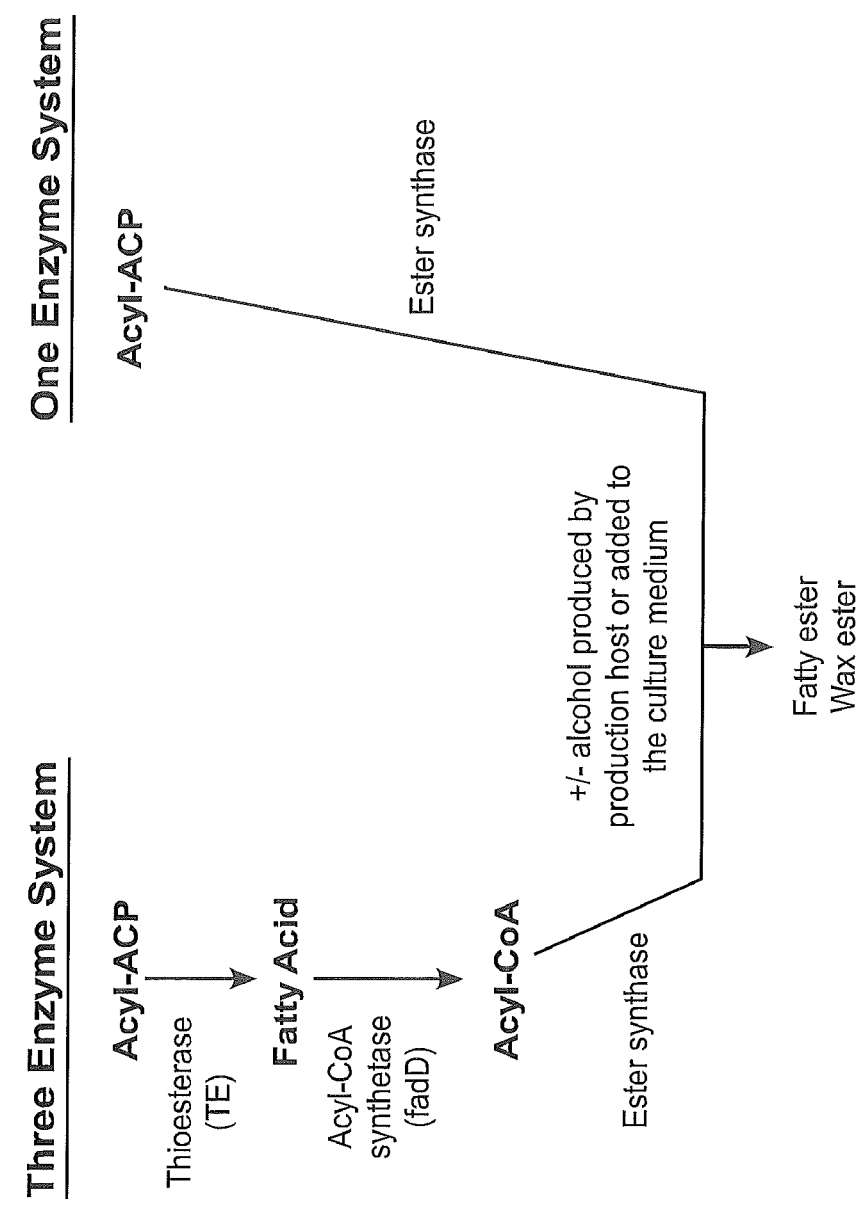
FIG. 5 presents an overview of two exemplary biosynthetic pathways for production of fatty esters starting with acyl-ACP, where the production of fatty esters is accomplished by a one-enzyme system or a three-enzyme-system.

The present disclosure provides numerous examples of polypeptides (i.e., enzymes) having activities suitable for use in the fatty acid biosynthetic pathways described herein. Such polypeptides are collectively referred to herein as "fatty acid biosynthetic polypeptides" or "fatty acid biosynthetic enzymes". Non-limiting examples of fatty acid pathway polypeptides suitable for use in recombinant host cells of the disclosure are provided herein. In some embodiments, the disclosure includes a recombinant host cell including a polynucleotide sequence which encodes a fatty acid biosynthetic polypeptide. The polynucleotide sequence, which includes an open reading frame encoding a fatty acid biosynthetic polypeptide and operably-linked regulatory sequences, can be integrated into a chromosome of the recombinant host cells, incorporated in one or more plasmid expression systems resident in the recombinant host cell, or both. In one embodiment, a fatty acid biosynthetic polynucleotide sequence encodes a polypeptide which is endogenous to the parental host cell (i.e., the control cell) of the recombinant host cell that is being engineered. Some such endogenous polypeptides are overexpressed in the recombinant host cell. In another embodiment, the fatty acid biosynthetic polynucleotide sequence encodes an exogenous or heterologous polypeptide. In other words, the polypeptide encoded by the polynucleotide is exogenous to the parental host cell. In yet another embodiment, the genetically modified host cell overexpresses a gene encoding a polypeptide (protein) that increases the rate at which the host cell produces the substrate of a fatty acid biosynthetic enzyme, i.e., a fatty acyl-thioester substrate. In certain embodiments, the enzyme encoded by the expressed gene is directly involved in fatty acid biosynthesis. Such recombinant host cells may be further engineered to include a polynucleotide sequence encoding one or more fatty acid biosynthetic polypeptides (i.e., enzymes involved in fatty acid biosynthesis). Examples of such polypeptides are polypeptides or proteins having thioesterase activity, wherein the recombinant host cell synthesizes fatty acids; or having thioesterase activity and carboxylic acid reductase (CAR) activity, wherein the recombinant host cell synthesizes fatty aldehydes and fatty alcohols; or having thioesterase activity, carboxylic acid reductase activity and alcohol dehydrogenase activity wherein the recombinant host cell synthesizes fatty alcohols; or having acyl-CoA reductase (AAR) activity wherein the recombinant host cell synthesizes fatty aldehydes and fatty alcohols; or having acyl-CoA reductase (AAR) activity and alcohol dehydrogenase activity wherein the recombinant host cell synthesizes fatty alcohols; or having fatty alcohol forming acyl-CoA reductase (FAR) activity, wherein the recombinant host cell synthesizes fatty alcohols; or having thioesterase activity, carboxylic acid reductase activity and aldehyde decarbonylase activity, wherein the recombinant host cell synthesizes alkanes; or having acyl-CoA reductase activity and aldehyde decarbonylase activity, wherein the recombinant host cell synthesizes alkanes; or having ester synthase activity wherein the recombinant host cell synthesizes fatty esters (e.g., one enzyme system; see FIG. 5); or having thioesterase activity, acyl-CoA synthase activity and ester synthase activity wherein the recombinant host cell synthesizes fatty esters (e.g., three enzyme system; see FIG. 5); or having OleA activity, wherein the recombinant host cell synthesizes aliphatic ketones; or having OleABCD activity, wherein the recombinant host cell synthesizes internal olefins; or having thioesterase activity and decarboxylase activity, wherein the recombinant host cell synthesizes terminal olefins; or combinations thereof. In some embodiments, at least one polypeptide encoded by a fatty acid biosynthetic polynucleotide is an exogenous (or heterologous) polypeptide (e.g., a polypeptide originating from an organism other than the parental host cell, or a variant of a polypeptide native to the parental microbial cell) or an endogenous polypeptide (i.e., a polypeptide native to the parental host cell) wherein the endogenous polypeptide is overexpressed in the recombinant host cell.

Table 1 below provides a listing of exemplary proteins which can be expressed in recombinant host cells to facilitate production of particular fatty acid derivatives.

TABLE 1

| Gene Designations | | | | | |
|---|---|---|---|---|---|
| Gene Designation | Source Organism | Enzyme Name | Accession No. | EC Number | Exemplary Use |
| 1. Fatty Acid Production Increase/Product Production Increase | | | | | |
| accA | E. coli, Lactococci | Acetyl-CoA carboxylase, subunit A (carboxyltransferase alpha) | AAC73296, NP_414727 | 6.4.1.2 | increase Malonyl-CoA production |
| accB | E. coli, Lactococci | Acetyl-CoA carboxylase, subunit B (BCCP: biotin carboxyl carrier protein) | NP_417721 | 6.4.1.2 | increase Malonyl-CoA production |
| accC | E. coli, Lactococci | Acetyl-CoA carboxylase, subunit C (biotin carboxylase) | NP_417722 | 6.4.1.2, 6.3.4.14 | increase Malonyl-CoA production |
| accD | E. coli, Lactococci | Acetyl-CoA carboxylase, subunit D (carboxyltransferase beta) | NP_416819 | 6.4.1.2 | increase Malonyl-CoA production |
| fadD | E. coli W3110 | acyl-CoA synthase | AP_002424 | 2.3.1.86, 6.2.1.3 | increase Fatty acid production |
| fabA | E. coli K12 | β-hydroxydecanoyl thioester dehydratase/ isomerase | NP_415474 | 4.2.1.60 | increase fatty acyl-ACP/CoA production |

TABLE 1-continued

| Gene Designation | Source Organism | Enzyme Name | Accession No. | EC Number | Exemplary Use |
|---|---|---|---|---|---|
| | | Gene Designations | | | |
| fabB | E. coli | 3-oxoacyl-[acyl-carrier-protein] synthase I | BAA16180 | 2.3.1.41 | increase fatty acyl-ACP/CoA production |
| fabD | E. coli K12 | [acyl-carrier-protein] S-malonyltransferase | AAC74176 | 2.3.1.39 | increase fatty acyl-ACP/CoA production |
| fabF | E. coli K12 | 3-oxoacyl-[acyl-carrier-protein] synthase II | AAC74179 | 2.3.1.179 | increase fatty acyl-ACP/CoA production |
| fabG | E. coli K12 | 3-oxoacyl-[acyl-carrier protein] reductase | AAC74177 | 1.1.1.100 | increase fatty acyl-ACP/CoA production |
| fabH | E. coli K12 | 3-oxoacyl-[acyl-carrier-protein] synthase III | AAC74175 | 2.3.1.180 | increase fatty acyl-ACP/CoA production |
| fabI | E. coli K12 | enoyl-[acyl-carrier-protein] reductase | NP_415804 | 1.3.1.9 | increase fatty acyl-ACP/CoA production |
| fabR | E. coli K12 | Transcriptional Repressor | NP_418398 | none | modulate unsaturated fatty acid production |
| fabV | Vibrio cholerae | enoyl-[acyl-carrier-protein] reductase | YP_001217283 | 1.3.1.9 | increase fatty acyl-ACP/CoA production |
| fabZ | E. coli K12 | (3R)-hydroxymyristol acyl carrier protein dehydratase | NP_414722 | 4.2.1.- | increase fatty acyl-ACP/CoA production |
| fadE | E. coli K13 | acyl-CoA dehydrogenase | AAC73325 | 1.3.99.3, 1.3.99.- | reduce fatty acid degradation |
| fadR | E. coli | transcriptional regulatory protein | NP_415705 | none | Block or reverse fatty acid degradation |
| | | 2. Chain Length Control | | | |
| tesA (with or without leader sequence) | E. coli | thioesterase-leader sequence is amino acids 1-26 | P0ADA1 | 3.1.2.-, 3.1.1.5 | C18 Chain Length |
| tesA (without leader sequence) | E. coli | thioesterase | AAC73596, NP_415027 | 3.1.2.-, 3.1.1.5 | C18:1 Chain Length |
| tesA (mutant of E. coli thioesterase I complexed with octanoic acid) | E. coli | thioesterase | L109P | 3.1.2.-, 3.1.1.5 | <C18 Chain Length |
| fatB1 | Umbellularia californica | thioesterase | Q41635 | 3.1.2.14 | C12:0 Chain Length |
| fatB2 | Cuphea hookeriana | thioesterase | AAC49269 | 3.1.2.14 | C8:0-C10:0 Chain Length |
| fatB3 | Cuphea hookeriana | thioesterase | AAC72881 | 3.1.2.14 | C14:0-C16:0 Chain Length |
| fatB | Cinnamomum camphora | thioesterase | Q39473 | 3.1.2.14 | C14:0 Chain Length |
| fatB | Arabidopsis thaliana | thioesterase | CAA85388 | 3.1.2.14 | C16:1 Chain Length |
| fatA1 | Helianthus annuus | thioesterase | AAL79361 | 3.1.2.14 | C18:1 Chain Length |
| atfata | Arabidopsis thaliana | thioesterase | NP_189147, NP_193041 | 3.1.2.14 | C18:1 Chain Length |
| fatA | Brassica juncea | thioesterase | CAC39106 | 3.1.2.14 | C18:1 Chain Length |
| fatA | Cuphea hookeriana | thioesterase | AAC72883 | 3.1.2.14 | C18:1 Chain Length |
| tes | Photbacterium profundum | thioesterase | YP_130990 | 3.1.2.14 | Chain Length |
| tesB | E. coli | thioesterase | NP_414986 | 3.1.2.14 | Chain Length |
| fadM | E. coli | thioesterase | NP_414977 | 3.1.2.14 | Chain Length |
| yciA | E. coli | thioesterase | NP_415769 | 3.1.2.14 | Chain Length |
| ybgC | E. coli | thioesterase | NP_415264 | 3.1.2.14 | Chain Length |
| | | 3. Saturation Level Control* | | | |
| Sfa | E. coli | Suppressor of fabA | AAN79592, AAC44390 | none | increase monounsaturated fatty acids |

TABLE 1-continued

Gene Designations

| Gene Designation | Source Organism | Enzyme Name | Accession No. | EC Number | Exemplary Use |
|---|---|---|---|---|---|
| fabA | *E. coli* K12 | β-hydroxydecanoyl thioester dehydratase/ isomerase | NP_415474 | 4.2.1.60 | produce unsaturated fatty acids |
| GnsA | *E. coli* | suppressors of the secG null mutation | ABD18647.1 | none | increase unsaturated fatty acid esters |
| GnsB | *E. coli* | suppressors of the secG null mutation | AAC74076.1 | none | increase unsaturated fatty acid esters |
| fabB | *E. coli* | 3-oxoacyl-[acyl-carrier-protein] synthase I | BAA16180 | 2.3.1.41 | modulate unsaturated fatty acid production |
| des | *Bacillus subtilis* | D5 fatty acyl desaturase | O34653 | 1.14.19 | modulate unsaturated fatty acid production |
| 4. Product Output: Wax Production | | | | | |
| AT3G51970 | *Arabidopsis thaliana* | long-chain-alcohol O-fatty-acyltransferase | NP_190765 | 2.3.1.26 | wax production |
| ELO1 | *Pichia angusta* | Fatty acid elongase | BAD98251 | 2.3.1.- | produce very long chain length fatty acids |
| plsC | *Saccharomyces cerevisiae* | acyltransferase | AAA16514 | 2.3.1.51 | wax production |
| DAGAT/ DGAT | *Arabidopsis thaliana* | diacylglycerol acyltransferase | AAF19262 | 2.3.1.20 | wax production |
| hWS | *Homo sapiens* | acyl-CoA wax alcohol acyltransferase | AAX48018 | 2.3.1.20 | wax production |
| aft1 | *Acinetobacter* sp. ADP1 | bifunctional wax ester synthase/acyl-CoA:diacylglycerol acyltransferase | AAO17391 | 2.3.1.20 | wax production |
| ES9 | *Marinobacter hydrocarbonoclasticus* | wax ester synthase | ABO21021 | 2.3.1.20 | wax production |
| mWS | *Simmondsia chinensis* | wax ester synthase | AAD38041 | 2.3.1.- | wax production |
| 5. Product Output: Fatty Alcohol Output | | | | | |
| | | thioesterases (see above) | | | increase fatty acid/fatty alcohol production |
| BmFAR | *Bombyxmori* | FAR (fatty alcohol forming acyl-CoA reductase) | BAC79425 | 1.1.1.- | convert acyl-CoA to fatty alcohol |
| acr1 | *Acinetobacter* sp. ADP1 | acyl-CoA reductase | YP_047869 | 1.2.1.42 | reduce fatty acyl-CoA to fatty aldehydes |
| yqhD | *E. coli* W3110 | alcohol dehydrogenase | AP_003562 | 1.1.-.- | reduce fatty aldehydes to fatty alcohols; increase fatty alcohol production |
| alrA | *Acinetobacter* sp. ADP1 | alcohol dehydrogenase | CAG70252 | 1.1.-.- | reduce fatty aldehydes to fatty alcohols |
| BmFAR | *Bombyxmori* | FAR (fatty alcohol forming acyl-CoA reductase) | BAC79425 | 1.1.1.- | reduce fatty acyl-CoA to fatty alcohol |
| GTNG_1865 | *Geobacillusthermodenitrificans* NG80-2 | Long-chain aldehyde dehydrogenase | YP_001125970 | 1.2.1.3 | reduce fatty aldehydes to fatty alcohols |
| AAR | *Synechococcus elongatus* | Acyl-ACP reductase | YP_400611 | 1.2.1.42 | reduce fatty acyl-ACP/CoA to fatty aldehydes |
| carB | *Mycobacterium smegmatis* | carboxylic acid reductase protein | YP_889972 | 6.2.1.3, 1.2.1.42 | reduce fatty acids to fatty aldehyde |
| FadD | *E. coli* K12 | acyl-CoA synthetase | NP_416319 | 6.2.1.3 | activates fatty acids to fatty acyl-CoAs |
| atoB | *Erwiniacarotovora* | acetyl-CoA acetyltransferase | YP_049388 | 2.3.1.9 | production of butanol |
| hbd | *Butyrivibriofibrisolvens* | Beta-hydroxybutyryl-CoA dehydrogenase | BAD51424 | 1.1.1.157 | production of butanol |

TABLE 1-continued

| Gene Designations | | | | | |
| --- | --- | --- | --- | --- | --- |
| Gene Designation | Source Organism | Enzyme Name | Accession No. | EC Number | Exemplary Use |
| CPE0095 | *Clostridium perfringens* | crotonasebutyryl-CoA dehydryogenase | BAB79801 | 4.2.1.55 | production of butanol |
| bcd | *Clostridium beijerinckii* | butyryl-CoA dehydryogenase | AAM14583 | 1.3.99.2 | production of butanol |
| ALDH | *Clostridium beijerinckii* | coenzyme A-acylating aldehyde dehydrogenase | AAT66436 | 1.2.1.3 | production of butanol |
| AdhE | *E. coli* CFT073 | aldehyde-alcohol dehydrogenase | AAN80172 | 1.1.1.1 1.2.1.10 | production of butanol |
| | | 6. Fatty Alcohol Acetyl Ester Output | | | |
| | | thioesterases (see above) | | | modify output |
| acr1 | *Acinetobacter* sp. ADP1 | acyl-CoA reductase | YP_047869 | 1.2.1.42 | modify output |
| yqhD | *E. Coli* K12 | alcohol dehydrogenase | AP_003562 | 1.1.-.- | modify output |
| AAT | *Fragaria x ananassa* | alcohol O-acetyltransferase | AAG13130 | 2.3.1.84 | modify output |
| | | 7. Product Export | | | |
| AtMRP5 | *Arabidopsis thaliana* | Arabidopsis thaliana multidrug resistance-associated | NP_171908 | none | modify product export amount |
| AmiS2 | *Rhodococcus* sp. | ABC transporter AmiS2 | JC5491 | none | modify product export amount |
| AtPGP1 | *Arabidopsis thaliana* | *Arabidopsis thaliana* p glycoprotein 1 | NP_181228 | none | modify product export amount |
| AcrA | *CandidatusProtochlamydiaamoebophila* UWE25 | putative multidrug-efflux transport protein acrA | CAF23274 | none | modify product export amount |
| AcrB | *CandidatusProtochlamydiaamoebophila* UWE25 | probable multidrug-efflux transport protein, acrB | CAF23275 | none | modify product export amount |
| TolC | *Francisellatularensis* subsp. *novicida* | Outer membrane protein [Cell envelope biogenesis, | ABD59001 | none | modify product export amount |
| AcrE | *Shigellasonnei* Ss046 | transmembrane protein affects septum formation and cell membrane permeability | YP_312213 | none | modify product export amount |
| AcrF | *E. coli* | Acriflavine resistance protein F | P24181 | none | modify product export amount |
| tll1619 | *Thermosynechococcus elongatus* [BP-1] | multidrug efflux transporter | NP_682409.1 | none | modify product export amount |
| tll0139 | *Thermosynechococcus elongatus* [BP-1] | multidrug efflux transporter | NP_680930.1 | none | modify product export amount |
| | | 8. Fermentation | | | |
| replication checkpoint genes | | | | | increase output efficiency |
| umuD | *Shigellasonnei* Ss046 | DNA polymerase V, subunit | YP_310132 | 3.4.21.- | increase output efficiency |
| umuC | *E. coli* | DNA polymerase V, subunit | ABC42261 | 2.7.7.7 | increase output efficiency |
| pntA, pntB | *Shigellaflexneri* | NADH:NADPH transhydrogenase (alpha and beta subunits) | P07001, P0AB70 | 1.6.1.2 | increase output efficiency |

TABLE 1-continued

Gene Designations

| Gene Designation | Source Organism | Enzyme Name | Accession No. | EC Number | Exemplary Use |
|---|---|---|---|---|---|
| 9. Other | | | | | |
| fabK | *Streptococcus pneumoniae* | trans-2-enoyl-ACP reductase II | AAF98273 | 1.3.1.9 | Contributes to fatty acid biosynthesis |
| fabL | *Bacillus licheniformis* DSM 13 | enoyl-(acyl carrier protein) reductase | AAU39821 | 1.3.1.9 | Contributes to fatty acid biosynthesis |
| fabM | *Streptococcus mutans* | trans-2, cis-3-decenoyl-ACP isomerase | DAA05501 | 4.2.1.17 | Contributes to fatty acid biosynthesis |

Production of Fatty Acids

The recombinant host cells may include one or more polynucleotide sequences that comprise an open reading frame encoding a thioesterase, e.g., having an Enzyme Commission number of EC 3.1.1.5 or EC 3.1.2.—(for example, EC 3.1.2.14), together with operably-linked regulatory sequences that facilitate expression of the protein in the recombinant host cells. In the recombinant host cells, the open reading frame coding sequences and/or the regulatory sequences are modified relative to the corresponding wild-type gene encoding the thioesterase. The activity of the thioesterase in the recombinant host cell is modified relative to the activity of the thioesterase expressed from the corresponding wild-type gene in a corresponding host cell. In some embodiments, a fatty acid derivative composition including fatty acids is produced by culturing a recombinant cell in the presence of a carbon source under conditions effective to express the thioesterase. In related embodiments, the recombinant host cell comprises a polynucleotide encoding a polypeptide having thioesterase activity, and one or more additional polynucleotides encoding polypeptides having other fatty acid biosynthetic enzyme activities. In some such instances, the fatty acid produced by the action of the thioesterase is converted by one or more enzymes having a different fatty acid biosynthetic enzyme activity to another fatty acid derivative, such as, for example, a fatty ester, fatty aldehyde, fatty alcohol, or a hydrocarbon.

The chain length of a fatty acid, or a fatty acid derivative made therefrom, can be selected for by modifying the expression of particular thioesterases. The thioesterase will influence the chain length of fatty acid derivatives produced. The chain length of a fatty acid derivative substrate can be selected for by modifying the expression of selected thioesterases (EC 3.1. 2.14 or EC 31.1.5). Hence, host cells can be engineered to express, overexpress, have attenuated expression, or not express one or more selected thioesterases to increase the production of a preferred fatty acid derivative substrate. For example, $C_{10}$ fatty acids can be produced by expressing a thioesterase that has a preference for producing $C_{10}$ fatty acids and attenuating thioesterases that have a preference for producing fatty acids other than $C_{10}$ fatty acids (e.g., a thioesterase which prefers to produce C14 fatty acids). This would result in a relatively homogeneous population of fatty acids that have a carbon chain length of 10. In other instances, $C_{14}$ fatty acids can be produced by attenuating endogenous thioesterases that produce non-$C_{14}$ fatty acids and expressing the thioesterases that use $C_{14}$-ACP. In some situations, $C_{12}$ fatty acids can be produced by expressing thioesterases that use $C_{12}$-ACP and attenuating thioesterases that produce non-$C_{12}$ fatty acids. For example, $C_{12}$ fatty acids can be produced by expressing a thioesterase that has a preference for producing $C_{12}$ fatty acids and attenuating thioesterases that have a preference for producing fatty acids other than $C_{12}$ fatty acids. This would result in a relatively homogeneous population of fatty acids that have a carbon chain length of 12. The fatty acid derivatives are recovered from the culture medium with substantially all of the fatty acid derivatives produced extracellularly. The fatty acid derivative composition produced by a recombinant host cell can be analyzed using methods known in the art, for example, GC-FID, in order to determine the distribution of particular fatty acid derivatives as well as chain lengths and degree of saturation of the components of the fatty acid derivative composition. Acetyl-CoA, malonyl-CoA, and fatty acid overproduction can be verified using methods known in the art, for example, by using radioactive precursors, HPLC, or GC-MS subsequent to cell lysis. Additional non-limiting examples of thioesterases and polynucleotides encoding them for use in the fatty acid pathway are provided in PCT Publication Application No. WO2010/075483, expressly incorporated by reference herein.

Production of Fatty Aldehydes

Figure 4:
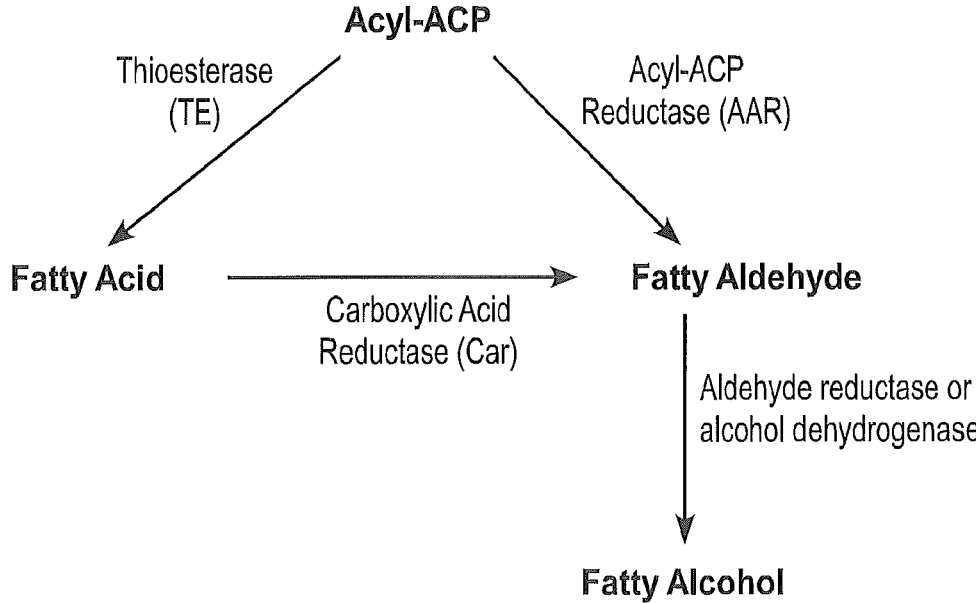
FIG. 4 presents an overview of an exemplary biosynthetic pathway for production of fatty alcohol starting with acyl-ACP, where the production of fatty aldehyde is catalyzed by the enzymatic activity of acyl-ACP reductase (AAR) or thioesterase (TE) and carboxylic acid reductase (Car). The fatty aldehyde is converted to fatty alcohol by aldehyde reductase (also referred to as alcohol dehydrogenase).

In one embodiment, the recombinant host cell produces a fatty aldehyde. In some embodiments, a fatty acid produced by the recombinant host cell is converted into a fatty aldehyde. In some embodiments, the fatty aldehyde produced by the recombinant host cell is then converted into a fatty alcohol or a hydrocarbon. In some embodiments, native (endogenous) fatty aldehyde biosynthetic polypeptides, such as aldehyde reductases, are present in the host cell (e.g., *E. coli*) and are effective to convert fatty aldehydes to fatty alcohols. In other embodiments, a native (endogenous) fatty aldehyde biosynthetic polypeptide is overexpressed. In still other embodiments, an exogenous fatty aldehyde biosynthetic polypeptide is introduced into a recombinant host cell and expressed or overexpressed. A native or recombinant host cell may comprise a polynucleotide encoding an enzyme having fatty aldehyde biosynthesis activity (e.g., a fatty aldehyde biosynthetic polypeptide or a fatty aldehyde biosynthetic polypeptide or enzyme). A fatty aldehyde is produced when the fatty aldehyde biosynthetic enzyme is expressed or overexpressed in the host cell. A recombinant host cell engineered to produce a fatty aldehyde will typically convert some of the fatty aldehyde to a fatty alcohol. In some embodiments, a fatty aldehyde is produced by expressing or overexpressing in the recombinant host cell a polynucleotide encoding a polypeptide having fatty aldehyde biosynthetic activity such as carboxylic acid reductase (CAR) activity. CarB, is an exemplary carboxylic acid reductase. In practicing the disclosure, a gene encoding a carboxylic acid reductase polypeptide may be expressed or overexpressed in the host cell. In some embodiments, the CarB polypeptide has the amino acid sequence of SEQ ID NO: 7. In other embodiments, the CarB polypeptide is a variant or mutant of SEQ ID NO: 7. Examples of carboxylic acid reductase (CAR) polypeptides and polynucleotides encoding them include, but are not limited to FadD9 (EC 6.2.1.-, UniProtKB Q50631, GenBank NP_217106, SEQ ID NO: 34), CarA (GenBank ABK75684), CarB (GenBank YP889972; SEQ ID NO: 33) and related polypeptides described in PCT Publication No. WO2010/042664 and U.S. Pat. No. 8,097,439, each of which is expressly incorporated by reference herein. In some embodiments the recombinant host cell further comprises a polynucleotide encoding a thioesterase. In some embodiments, the fatty aldehyde is produced by expressing or overexpressing in the recombinant host cell a polynucleotide encoding a fatty aldehyde biosynthetic polypeptide, such as a polypeptide having acyl-ACP reductase (AAR) activity. Expression of acyl-ACP reductase in a recombinant host cell results in the production of fatty aldehydes and fatty alcohols (see FIG. 4). Native (endogenous) aldehyde reductases present in a recombinant host cell (e.g., *E. coli*), can convert fatty aldehydes into fatty alcohols. Exemplary acyl-ACP reductase polypeptides are described in PCT Publication Nos. WO2009/140695 and WO/2009/140696, both of which are expressly incorporated by reference herein. A composition comprising fatty aldehydes (a fatty aldehyde composition) is produced by culturing a host cell in the presence of a carbon source under conditions effective to express the fatty aldehyde biosynthetic enzyme. In some embodiments, the fatty aldehyde composition comprises fatty aldehydes and fatty alcohols. Typically, the fatty aldehyde composition is recovered from the extracellular environment of the recombinant host cell, i.e., the cell culture medium.

Production of Fatty Alcohols

In some embodiments, the recombinant host cell includes a polynucleotide encoding a polypeptide (an enzyme) having fatty alcohol biosynthetic activity (a fatty alcohol biosynthetic polypeptide or a fatty alcohol biosynthetic enzyme), and a fatty alcohol is produced by the recombinant host cell. A composition comprising fatty alcohols (a fatty alcohol composition) may be produced by culturing the recombinant host cell in the presence of a carbon source under conditions effective to express a fatty alcohol biosynthetic enzyme. In some embodiments, the fatty alcohol composition comprises fatty alcohols, however, a fatty alcohol composition may comprise other fatty acid derivatives. Typically, the fatty alcohol composition is recovered from the extracellular environment of the recombinant host cell, i.e., the cell culture medium. In one approach, recombinant host cells have been engineered to produce fatty alcohols by expressing a thioesterase, which catalyzes the conversion of acyl-ACPs into free fatty acids (FFAs) and a carboxylic acid reductase (CAR), which converts free fatty acids into fatty aldehydes. Native (endogenous) aldehyde reductases present in the host cell (e.g., *E. coli*) can convert the fatty aldehydes into fatty alcohols. In some embodiments, native (endogenous) fatty aldehyde biosynthetic polypeptides, such as aldehyde reductases present in the host cell, may be sufficient to convert fatty aldehydes to fatty alcohols. However, in other embodiments, a native (endogenous) fatty aldehyde biosynthetic polypeptide is overexpressed and in still other embodiments, an exogenous fatty aldehyde biosynthetic polypeptide is introduced into a recombinant host cell and expressed or overexpressed. In some embodiments, the fatty alcohol is produced by expressing or overexpressing in the recombinant host cell a polynucleotide encoding a polypeptide having fatty alcohol biosynthetic activity which converts a fatty aldehyde to a fatty alcohol. For example, an alcohol dehydrogenase (aldehyde reductase, e.g., EC 1.1.1.1), may be used in practicing the disclosure. As used herein, an alcohol dehydrogenase refers to a polypeptide capable of catalyzing the conversion of a fatty aldehyde to an alcohol (e.g., a fatty alcohol). One of ordinary skill in the art will appreciate that certain alcohol dehydrogenases are capable of catalyzing other reactions as well, and these non-specific alcohol dehydrogenases also are encompassed by the alcohol dehydrogenase. Examples of alcohol dehydrogenase polypeptides useful in accordance with the disclosure include, but are not limited to AlrA of *Acinetobacter* sp. M-1 (SEQ ID NO: 3) or AlrA homologs such as AlrAadp1 (SEQ ID NO: 4) and endogenous *E. coli* alcohol dehydrogenases such as YjgB, (AAC77226) (SEQ ID NO: 5), DkgA (NP_417485), DkgB (NP_414743), YdjL (AAC74846), YdjJ (NP_416288), AdhP (NP_415995), YhdH (NP_417719), YahK (NP_414859), YphC (AAC75598), YqhD (446856) and YbbO [AAC73595.1]. Additional examples are described in International Patent Application Publication Nos. WO 2007/136762, WO2008/119082 and WO 2010/062480, each of which is expressly incorporated by reference herein. In certain embodiments, the fatty alcohol biosynthetic polypeptide has aldehyde reductase or alcohol dehydrogenase activity (EC 1.1.1.1).

In another approach, recombinant host cells have been engineered to produce fatty alcohols by expressing fatty alcohol forming acyl-CoA reductases or fatty acyl reductases (FARs) which convert fatty acyl-thioester substrates (e.g., fatty acyl-CoA or fatty acyl-ACP) to fatty alcohols. In some embodiments, the fatty alcohol is produced by expressing or overexpressing a polynucleotide encoding a polypeptide having fatty alcohol forming acyl-CoA reductase (FAR) activity in a recombinant host cell. Examples of FAR polypeptides useful in accordance with this embodiment are described in PCT Publication No. WO2010/062480 which is expressly incorporated by reference herein. Fatty alcohol may be produced via an acyl-CoA dependent pathway utilizing fatty acyl-ACP and fatty acyl-CoA intermediates and an acyl-CoA independent pathway utilizing fatty acyl-ACP intermediates but not a fatty acyl-CoA intermediate. In particular embodiments, the enzyme encoded by the over expressed gene is selected from a fatty acid synthase, an acyl-ACP thioesterase, a fatty acyl-CoA synthase and an acetyl-CoA carboxylase. In some embodiments, the protein encoded by the over expressed gene is endogenous to the host cell. In other embodiments, the protein encoded by the overexpressed gene is heterologous to the host cell. Fatty alcohols are also made in nature by enzymes that are able to reduce various acyl-ACP or acyl-CoA molecules to the corresponding primary alcohols. See also, U.S. Patent Publication Nos. 20100105963, and 20110206630 and U.S. Pat. No. 8,097,439, expressly incorporated by reference herein. Strategies to increase production of fatty alcohols by recombinant host cells include increased flux through the fatty acid biosynthetic pathway by overexpression of native fatty acid biosynthetic genes and/or expression of exogenous fatty acid biosynthetic genes from different organisms in the production host such that fatty alcohol biosynthesis is increased.

Production of Esters

As used herein, the term "fatty ester" may be used with reference to an ester. A fatty ester as referred to herein can be any ester made from a fatty acid, for example a fatty acid ester. In some embodiments, a fatty ester contains an A side and a B side. As used herein, an "A side" of an ester refers to the carbon chain attached to the carboxylate oxygen of the ester. As used herein, a "B side" of an ester refers to the carbon chain comprising the parent carboxylate of the ester. In embodiments where the fatty ester is derived from the fatty acid biosynthetic pathway, the A side is contributed by an alcohol, and the B side is contributed by a fatty acid. Any alcohol can be used to form the A side of the fatty esters. For example, the alcohol can be derived from the fatty acid biosynthetic pathway. Alternatively, the alcohol can be produced through non-fatty acid biosynthetic pathways. Moreover, the alcohol can be provided exogenously. For example, the alcohol can be supplied in the fermentation broth in instances where the fatty ester is produced by an organism. Alternatively, a carboxylic acid, such as a fatty acid or acetic acid, can be supplied exogenously in instances where the fatty ester is produced by an organism that can also produce alcohol. The carbon chains comprising the A side or B side can be of any length. In one embodiment, the A side of the ester is at least about 1, 2, 3, 4, 5, 6, 7, 8, 10, 12, 14, 16, or 18 carbons in length. When the fatty ester is a fatty acid methyl ester, the A side of the ester is 1 carbon in length. When the fatty ester is a fatty acid ethyl ester, the A side of the ester is 2 carbons in length. The B side of the ester can be at least about 4, 6, 8, 10, 12, 14, 16, 18, 20, 22, 24, or 26 carbons in length. The A side and/or the B side can be straight or branched chain. The branched chains can have one or more points of branching. In addition, the branched chains can include cyclic branches. Furthermore, the A side and/or B side can be saturated or unsaturated. If unsaturated, the A side and/or B side can have one or more points of unsaturation. In one embodiment, the fatty ester is produced biosynthetically. In this embodiment, first the fatty acid is activated. Non-limiting examples of "activated" fatty acids are acyl-CoA, acyl ACP, and acyl phosphate. Acyl-CoA can be a direct product of fatty acid biosynthesis or degradation. In addition, acyl-CoA can be synthesized from a free fatty acid, a CoA, and an adenosine nucleotide triphosphate (ATP). An example of an enzyme which produces acyl-CoA is acyl-CoA synthase. In some embodiments, the recombinant host cell comprises a polynucleotide encoding a polypeptide, e.g., an enzyme having ester synthase activity, (ester synthase polypeptide or an ester synthase).

A fatty ester is produced by a reaction catalyzed by the ester synthase polypeptide expressed or overexpressed in the recombinant host cell. In some embodiments, a composition comprising fatty esters fatty ester is produced by culturing the recombinant cell in the presence of a carbon source under conditions effective to express an ester synthase. In some embodiments, the fatty ester composition is recovered from the cell culture. Ester synthase polypeptides include, for example, an ester synthase polypeptide classified as EC 2.3.1.75, or any other polypeptide which catalyzes the conversion of an acyl-thioester to a fatty ester, including, without limitation, a thioesterase, an ester synthase, an acyl-CoA:alcohol transacylase, an acyltransferase, or a fatty acyl-CoA:fatty alcohol acyltransferase. For example, the polynucleotide may encode wax/dgat, a bifunctional ester synthase/acyl-CoA:diacylglycerol acyltransferase from *Simmondsia chinensis, Acinetobacter* sp. Strain ADP, *Alcanivorax borkumensis, Pseudomonas aeruginosa, Fundibacter jadensis, Arabidopsis thaliana*, or *Alkaligenes eutrophus*. In a particular embodiment, the ester synthase polypeptide is an *Acinetobacter* sp. diacylglycerol O-acyltransferase (wax-dgaT; UniProtKB Q8GGG1, GenBank AA017391) or *Simmondsia chinensis* wax synthase (UniProtKB Q9XGY6, GenBank AAD38041. In another embodiment, the ester synthase polypeptide is for example ES9 (a wax ester synthase from *Marinobacter hydrocarbonoclasticus* DSM 8798, UniProtKB A3RE51 (SEQ ID NO: 6); ES8 of *Marinobacter hydrocarbonoclasticus* DSM8789 (GenBank Accession No. AB021021; SEQ ID NO:7); GenBank AB021021, encoded by the ws2 gene; or ES376 (another wax ester synthase derived from *Marinobacter hydrocarbonoclasticus* DSM 8798, UniProtKB A3RE50, GenBank ABO21020, encoded by the ws1 gene. In a particular embodiment, the polynucleotide encoding the ester synthase polypeptide is overexpressed in the recombinant host cell. In some embodiments, a fatty acid ester is produced by a recombinant host cell engineered to express three fatty acid biosynthetic enzymes: a thioesterase enzyme, an acyl-CoA synthetase (fadD) enzyme and an ester synthase enzyme (e.g., three enzyme system; see FIG. 5). In other embodiments, a fatty acid ester is produced by a recombinant host cell engineered to express one fatty acid biosynthetic enzyme, an ester synthase enzyme (e.g., one enzyme system; see FIG. 5). Non-limiting examples of ester synthase polypeptides and polynucleotides encoding them suitable for use in these embodiments include those described in PCT Publication Nos. WO2007/136762 and WO2008/119082, and WO/2011/038134 (three enzyme system) and WO/2011/038132 (one enzyme system), each of which is expressly incorporated by reference herein. The recombinant host cell may produce a fatty ester, such as a fatty acid methyl ester, a fatty acid ethyl ester or a wax ester in the extracellular environment of the host cells.

Production of Hydrocarbons

Figure 6:
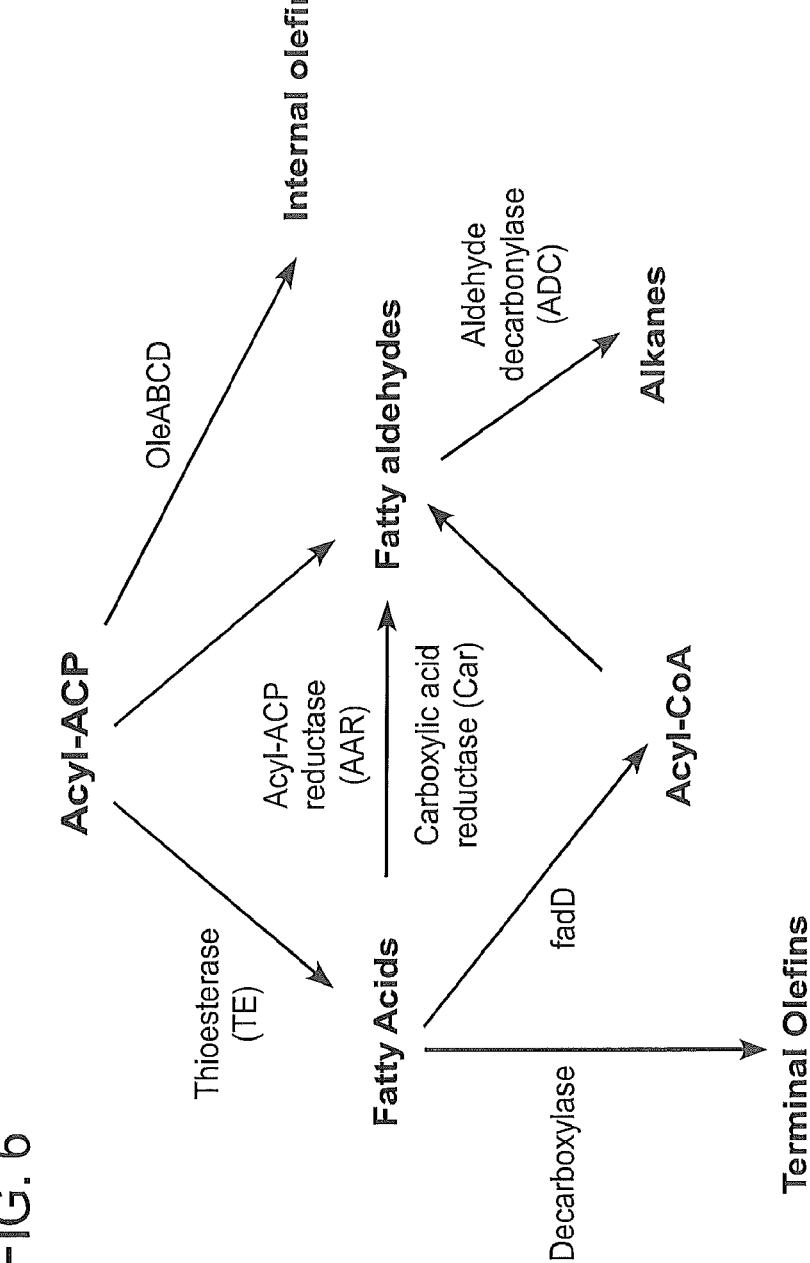
FIG. 6 presents an overview of exemplary biosynthetic pathways for production of hydrocarbons starting with acyl-ACP; the production of internal olefins is catalyzed by the enzymatic activity of OleABCD; the production of alkanes is catalyzed by the enzymatic conversion of fatty aldehydes to alkanes by way of aldehyde decarbonylase (ADC); and the production of terminal olefins is catalyzed by the enzymatic conversion of fatty acids to terminal olefins by a decarboxylase.

This aspect of the disclosure is based, at least in part, on the discovery that altering the level of expression of a fatty aldehyde biosynthetic polypeptide, for example, an acyl-ACP reductase polypeptide (EC 6.4.1.2) and a hydrocarbon biosynthetic polypeptide, e.g., a decarbonylase in a recombinant host cell facilitates enhanced production of hydrocarbons by the recombinant host cell. In one embodiment, the recombinant host cell produces a hydrocarbon, such as an alkane or an alkene (e.g., a terminal olefin or an internal olefin) or a ketone. In some embodiments, a fatty aldehyde produced by a recombinant host cell is converted by decarbonylation, removing a carbon atom to form a hydrocarbon. In other embodiments, a fatty acid produced by a recombinant host cell is converted by decarboxylation, removing a carbon atom to form a terminal olefin. In some embodiments, an acyl-ACP intermediate is converted by decarboxylation, removing a carbon atom to form an internal olefin or a ketone (see FIG. 6). In some embodiments, the recombinant host cell comprises a polynucleotide encoding a polypeptide (an enzyme) having hydrocarbon biosynthetic activity (a hydrocarbon biosynthetic polypeptide or a hydrocarbon biosynthetic enzyme), and the hydrocarbon is produced by expression or overexpression of the hydrocarbon biosynthetic enzyme in a recombinant host cell. An alkane biosynthetic pathway from cyanobacteria consisting of an acyl-acyl carrier protein reductase (AAR) and an aldehyde decarbonylase (ADC), which together convert intermediates of fatty acid metabolism to alkanes and alkenes has been used to engineer recombinant host cells for the production of hydrocarbons (FIG. 6). The second of two reactions in the pathway through which saturated acyl-ACPs are converted to alkanes in cyanobacteria entails scission of the C1-C2 bond of a fatty aldehyde intermediate by the enzyme aldehyde decarbonylase (ADC), a ferritin-like protein with a binuclear metal cofactor of unknown composition. In some embodiments, the hydrocarbon is produced by expressing or overexpressing in the recombinant host cell a polynucleotide encoding a polypeptide having hydrocarbon biosynthetic activity such as an aldehyde decarbonylase (ADC) activity (e.g., EC 4.1.99.5). Exemplary polynucleotides encoding an aldehyde decarbonylase useful in accordance with this embodiment include, but are not limited to, those described in PCT Publication Nos. WO2008/119082 and WO2009/140695 which are expressly incorporated by reference herein and those sequences presented in Table 2 below. In some embodiments the recombinant host cell further comprises a polynucleotide encoding a fatty aldehyde biosynthesis polypeptide. In some embodiments the recombinant host cell further comprises a polynucleotide encoding an acyl-ACP reductase. See, for example, Table 2 below.

TABLE 2

Exemplary Hydrocarbon Biosynthetic Polynucleotides and Polypeptides

| Protein name | Polypeptide sequence | Nucleotide sequence | Sequence |
|---|---|---|---|
| Decarbonylase (ADC) | SEQ ID NO: 35 | SEQ ID NO: 36 | *Synechococcus elongatus* PCC7942 YP.sub.--400610 (Synpcc7942.sub.--1593) |
| Acyl-ACP Reductase (AAR) | SEQ ID NO: 37 | SEQ ID NO: 38 | *Synechococcus elongatus* PCC7942 YP_400611 (Synpcc7942_1594) |
| Decarbonylase (ADC) | SEQ ID NO: 39 | SEQ ID NO: 40 | *Prochlorococcus mariunus* CCMP1986 PMM0532 |
| Acyl-ACP Reductase (AAR) | SEQ ID NO: 41 | SEQ ID NO: 42 | *Prochlorococcus marinus* CCMP1986 PMM0533 (NP_892651) |

In some embodiments, a composition comprising is produced by culturing the recombinant cell in the presence of a carbon source under conditions effective to express the Acyl-CoA reductase and decarbonylase polynucleotides. In some embodiments, the hydrocarbon composition comprises saturated and unsaturated hydrocarbons. However, a hydrocarbon composition may comprise other fatty acid derivatives. Typically, the hydrocarbon composition is recovered from the extracellular environment of the recombinant host cell, i.e., the cell culture medium. As used herein, an alkane refers to saturated hydrocarbons or compounds that consist only of carbon (C) and hydrogen (H), wherein these atoms are linked together by single bonds (i.e., they are saturated compounds). Olefins and alkenes refer to hydrocarbons containing at least one carbon-to-carbon double bond (i.e., they are unsaturated compounds). Terminal olefins, α-olefins, terminal alkenes, and 1-alkenes refer to the same compounds with reference to α-olefins or alkenes with a chemical formula CxH2x, distinguished from other olefins with a similar molecular formula by linearity of the hydrocarbon chain and the position of the double bond at the primary or alpha position. In some embodiments, a terminal olefin is produced by expressing or overexpressing in the recombinant host cell a polynucleotide encoding a hydrocarbon biosynthetic polypeptide, such as a polypeptide having decarboxylase activity as described, for example, in PCT Publication No. WO2009/085278 which is expressly incorporated by reference herein. In some embodiments the recombinant host cell further comprises a polynucleotide encoding a thioesterase. In other embodiments, a ketone is produced by expressing or overexpressing in the recombinant host cell a polynucleotide encoding a hydrocarbon biosynthetic polypeptide, such as a polypeptide having OleA activity as described, for example, in PCT Publication No.

WO2008/147781, which is expressly incorporated by reference herein. In related embodiments, an internal olefin is produced by expressing or overexpressing in the recombinant host cell a polynucleotide encoding a hydrocarbon biosynthetic polypeptide, such as a polypeptide having OleCD or OleBCD activity together with a polypeptide having OleA activity as described, for example, in PCT Publication No. WO2008/147781, expressly incorporated by reference herein.

Recombinant Host Cells and Cell Cultures

Strategies to increase production of fatty acid derivatives by recombinant host cells include increased flux through the fatty acid biosynthetic pathway by overexpression of native fatty acid biosynthetic genes and expression of exogenous fatty acid biosynthetic genes from different organisms in the production host. As used herein, a recombinant host cell or engineered host cell refers to a host cell whose genetic makeup has been altered relative to the corresponding wild-type host cell, for example, by deliberate introduction of new genetic elements and/or deliberate modification of genetic elements naturally present in the host cell. The offspring of such recombinant host cells also contain these new and/or modified genetic elements. In any of the aspects of the disclosure described herein, the host cell can be selected from the group consisting of a plant cell, insect cell, fungus cell (e.g., a filamentous fungus, such as *Candida* sp., or a budding yeast, such as *Saccharomyces* sp.), an algal cell and a bacterial cell. In one preferred embodiment, recombinant host cells are recombinant microorganisms. Examples of host cells that are microorganisms, include but are not limited to cells from the genus *Escherichia, Bacillus, Lactobacillus, Zymomonas, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia,* or *Streptomyces.* In some embodiments, the host cell is a Gram-positive bacterial cell. In other embodiments, the host cell is a Gram-negative bacterial cell. In some embodiments, the host cell is an *E. coli* cell. In other embodiments, the host cell is a *Bacillus lentus* cell, a *Bacillus brevis* cell, a *Bacillus stearothermophilus* cell, a *Bacillus licheniformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell. In other embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus* fumigates cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcus opacus* cell, a *Rhizomucor miehei* cell, or a *Mucor michei* cell. In yet other embodiments, the host cell is a *Streptomyces lividans* cell or a *Streptomyces murinus* cell. In yet other embodiments, the host cell is an Actinomycetes cell. In some embodiments, the host cell is a *Saccharomyces cerevisiae* cell. In other embodiments, the host cell is a cell from a eukaryotic plant, algae, cyanobacterium, green-sulfur bacterium, green non-sulfur bacterium, purple sulfur bacterium, purple non-sulfur bacterium, extremophile, yeast, fungus, an engineered organism thereof, or a synthetic organism. In some embodiments, the host cell is light-dependent or fixes carbon. In some embodiments, the host cell has autotrophic activity. In some embodiments, the host cell has photoautotrophic activity, such as in the presence of light. In some embodiments, the host cell is heterotrophic or mixotrophic in the absence of light. In certain embodiments, the host cell is a cell from *Arabidopsis thaliana, Panicum virgatum, Miscanthus giganteus, Zea mays, Botryococcuse braunii, Chlamydomonas reinhardtii, Dunaliela salina, Synechococcus* Sp. PCC 7002, *Synechococcus* Sp. PCC 7942, *Synechocystis* Sp. PCC 6803, *Thermosynechococcus elongates* BP-1, *Chlorobium tepidum, Chlorojlexus auranticus, Chromatiumm vinosum, Rhodospirillum rubrum, Rhodobacter capsulatus, Rhodopseudomonas palusris, Clostridium ljungdahlii, Clostridiuthermocellum, Penicillium chrysogenum, Pichia pastoris, Saccharomyces cerevisiae, Schizosaccharomyces pombe, Pseudomonas fluorescens,* or *Zymomonas mobilis.*

Production of Fatty Acid Derivative Compositions by Recombinant Host cells

A large variety of fatty acid derivatives can be produced by recombinant host cells comprising strain improvements as described herein, including, but not limited to, fatty acids, acyl-CoA, fatty aldehydes, short and long chain alcohols, hydrocarbons (e.g., alkanes, alkenes or olefins, such as terminal or internal olefins), fatty alcohols, esters (e.g., wax esters, fatty acid esters (e.g., methyl or ethyl esters)), and ketones. In some embodiments of the present disclosure, the higher titer of fatty acid derivatives in a particular composition is a higher titer of a particular type of fatty acid derivative (e.g., fatty alcohols, fatty acid esters, or hydrocarbons) produced by a recombinant host cell culture relative to the titer of the same fatty acid derivatives produced by a control culture of a corresponding wild-type host cell. In such cases, the fatty acid derivative compositions may comprise, for example, a mixture of the fatty alcohols with a variety of chain lengths and saturation or branching characteristics. In other embodiments of the present disclosure, the higher titer of fatty acid derivatives in a particular compositions is a higher titer of a combination of different fatty acid derivatives (for example, fatty aldehydes and alcohols, or fatty acids and esters) relative to the titer of the same fatty acid derivative produced by a control culture of a corresponding wild-type host cell.

Engineering Host Cells

In some embodiments, a polynucleotide (or gene) sequence is provided to the host cell by way of a recombinant vector, which comprises a promoter operably linked to the polynucleotide sequence. In certain embodiments, the promoter is a developmentally-regulated, an organelle-specific, a tissue-specific, an inducible, a constitutive, or a cell-specific promoter. In some embodiments, the recombinant vector includes at least one sequence including, but not limited to, (a) an expression control sequence operatively coupled to the polynucleotide sequence; (b) a selection marker operatively coupled to the polynucleotide sequence; (c) a marker sequence operatively coupled to the polynucleotide sequence; (d) a purification moiety operatively coupled to the polynucleotide sequence; (e) a secretion sequence operatively coupled to the polynucleotide sequence; and (f) a targeting sequence operatively coupled to the polynucleotide sequence. The expression vectors described herein include a polynucleotide sequence described herein in a form suitable for expression of the polynucleotide sequence in a host cell. It will be appreciated by those skilled in the art that the design of the expression vector can depend on such factors as the choice of the host cell to be transformed, the level of expression of polypeptide desired, etc. The expression vectors described herein can be introduced into host cells to produce polypeptides, including fusion polypeptides, encoded by the polynucleotide sequences as described herein. Expression of genes encoding polypeptides in prokaryotes, for example, *E. coli*, is most often carried out with vectors containing constitutive or inducible promoters directing the expression of either fusion or non-fusion polypeptides. Fusion vectors add a number of amino acids to a polypeptide encoded therein, usually to the amino- or carboxy-terminus of the recombinant polypeptide. Such fusion vectors typically serve one or more of the following three purposes (1) to increase expression of the recombinant polypeptide; (2) to increase the solubility of the recombinant polypeptide; and (3) to aid in the purification of the recombinant polypeptide by acting as a ligand in affinity purification. Often, in fusion expression vectors, a proteolytic cleavage site is introduced at the junction of the fusion moiety and the recombinant polypeptide. This enables separation of the recombinant polypeptide from the fusion moiety after purification of the fusion polypeptide. Examples of such enzymes, and their cognate recognition sequences, include Factor Xa, thrombin, and enterokinase. Exemplary fusion expression vectors include pGEX (Pharmacia Biotech, Inc., Piscataway, NJ; Smith et al., Gene, 67: 31-40 (1988)), pMAL (New England Biolabs, Beverly, MA), and pRITS (Pharmacia Biotech, Inc., Piscataway, N.J.), which fuse glutathione S-transferase (GST), maltose E binding protein, or protein A, respectively, to the target recombinant polypeptide. Examples of inducible, non-fusion *E. coli* expression vectors include pTrc (Amann et al., Gene (1988) 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident k prophage harboring a T7 gn1 gene under the transcriptional control of the lacUV 5 promoter. Suitable expression systems for both prokaryotic and eukaryotic cells are well known in the art; see, e.g., Sambrook et al., "Molecular Cloning: A Laboratory Manual," second edition, Cold Spring Harbor Laboratory, (1989). Examples of inducible, non-fusion *E. coli* expression vectors include pTrc (Amann et al., Gene, 69: 301-315 (1988)) and PET 11d (Studier et al., Gene Expression Technology: Methods in Enzymology 185, Academic Press, San Diego, CA, pp. 60-89 (1990)). In certain embodiments, a polynucleotide sequence of the disclosure is operably linked to a promoter derived from bacteriophage T5. In one embodiment, the host cell is a yeast cell. In this embodiment, the expression vector is a yeast expression vector. Vectors can be introduced into prokaryotic or eukaryotic cells via a variety of art-recognized techniques for introducing foreign nucleic acid (e.g., DNA) into a host cell. Suitable methods for transforming or transfecting host cells can be found in, for example, Sambrook et al. (supra). For stable transformation of bacterial cells, it is known that, depending upon the expression vector and transformation technique used, only a small fraction of cells will take-up and replicate the expression vector. In order to identify and select these transformants, a gene that encodes a selectable marker (e.g., resistance to an antibiotic) can be introduced into the host cells along with the gene of interest. Selectable markers include those that confer resistance to drugs such as, but not limited to, ampicillin, kanamycin, chloramphenicol, or tetracycline. Nucleic acids encoding a selectable marker can be introduced into a host cell on the same vector as that encoding a polypeptide described herein or can be introduced on a separate vector. Cells stably transformed with the introduced nucleic acid can be identified by growth in the presence of an appropriate selection drug.

Host Cells

As used herein, an engineered or recombinant host cell is a cell used to produce a fatty acid derivative composition as further described herein. A host cell is referred to as an engineered host cell or a recombinant host cell if the expression of one or more polynucleotides or polypeptides in the host cell are altered or modified as compared to their expression in a corresponding wild-type host cell (e.g., control cell) under the same conditions. In any of the aspects of the disclosure described herein, the host cell can be selected from the group consisting of a eukaryotic plant, algae, cyanobacterium, green-sulfur bacterium, green non-sulfur bacterium, purple sulfur bacterium, purple non-sulfur bacterium, extremophile, yeast, fungus, engineered organisms thereof, or a synthetic organism. In some embodiments, the host cell is light dependent or fixes carbon. In some embodiments, the host cell has autotrophic activity. Various host cells can be used to produce fatty acid derivatives, as described herein.

Mutants or Variants

In some embodiments, the polypeptide is a mutant or a variant of any of the polypeptides described herein. The terms mutant and variant as used herein refer to a polypeptide having an amino acid sequence that differs from a wild-type polypeptide by at least one amino acid. For example, the mutant can comprise one or more of the following conservative amino acid substitutions: replacement of an aliphatic amino acid, such as alanine, valine, leucine, and isoleucine, with another aliphatic amino acid; replacement of a serine with a threonine; replacement of a threonine with a serine; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue. In some embodiments, the mutant polypeptide has about 1, 2, 3, 4, 5, 6, 7, 8, 9, 10, 15, 20, 30, 40, 50, 60, 70, 80, 90, 100, or more amino acid substitutions, additions, insertions, or deletions. Preferred fragments or mutants of a polypeptide retain some or all of the biological function (e.g., enzymatic activity) of the corresponding wild-type polypeptide. In some embodiments, the fragment or mutant retains at least 75%, at least 80%, at least 90%, at least 95%, or at least 98% or more of the biological function of the corresponding wild-type polypeptide. In other embodiments, the fragment or mutant retains about 100% of the biological function of the corresponding wild-type polypeptide. Guidance in determining which amino acid residues may be substituted, inserted, or deleted without affecting biological activity may be found using computer programs well known in the art, for example, LASERGENE™ software (DNASTAR, Inc., Madison, WI). In yet other embodiments, a fragment or mutant exhibits increased biological function as compared to a corresponding wild-type polypeptide. For example, a fragment or mutant may display at least a 10%, at least a 25%, at least a 50%, at least a 75%, or at least a 90% improvement in enzymatic activity as compared to the corresponding wild-type polypeptide. In other embodiments, the fragment or mutant displays at least 100% (e.g., at least 200%, or at least 500%) improvement in enzymatic activity as compared to the corresponding wild-type polypeptide. It is understood that the polypeptides described herein may have additional conservative or non-essential amino acid substitutions, which do not have a substantial effect on the polypeptide function. Whether or not a particular substitution will be tolerated (i.e., will not adversely affect desired biological function, such as carboxylic acid reductase activity) can be determined as described in Bowie et al. (Science, 247: 1306-1310 (1990)). A conservative amino acid substitution is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

Variants can be naturally occurring or created in vitro. In particular, such variants can be created using genetic engineering techniques, such as site directed mutagenesis, random chemical mutagenesis, Exonuclease III deletion procedures, or standard cloning techniques. Alternatively, such variants, fragments, analogs, or derivatives can be created using chemical synthesis or modification procedures. Methods of making variants are well known in the art. These include procedures in which nucleic acid sequences obtained from natural isolates are modified to generate nucleic acids that encode polypeptides having characteristics that enhance their value in industrial or laboratory applications. In such procedures, a large number of variant sequences having one or more nucleotide differences with respect to the sequence obtained from the natural isolate are generated and characterized. Typically, these nucleotide differences result in amino acid changes with respect to the polypeptides encoded by the nucleic acids from the natural isolates. For example, variants can be prepared by using random and site-directed mutagenesis. Random and site-directed mutagenesis are described in, for example, Arnold, Curr. Opin. Biotech., 4: 450-455 (1993). Random mutagenesis can be achieved using error prone PCR (see, e.g., Leung et al., Technique, 1: 11-15 (1989); and Caldwell et al., PCR Methods Applic., 2: 28-33 (1992)). In error prone PCR, PCR is performed under conditions where the copying fidelity of the DNA polymerase is low, such that a high rate of point mutations is obtained along the entire length of the PCR product. Briefly, in such procedures, nucleic acids to be mutagenized (e.g., a polynucleotide sequence encoding a carboxylic reductase enzyme) are mixed with PCR primers, reaction buffer, $MgCl_2$, $MnCl_2$, Taq polymerase, and an appropriate concentration of dNTPs for achieving a high rate of point mutation along the entire length of the PCR product. For example, the reaction can be performed using 20 fmoles of nucleic acid to be mutagenized, 30 pmole of each PCR primer, a reaction buffer comprising 50 mM KCl, 10 mM Tris HCl (pH 8.3), 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR can be performed for 30 cycles of 94° C. for 1 min, 45° C. for 1 min, and 72° C. for 1 min. However, it will be appreciated that these parameters can be varied as appropriate. The mutagenized nucleic acids are then cloned into an appropriate vector, and the activities of the polypeptides encoded by the mutagenized nucleic acids are evaluated. Site-directed mutagenesis can be achieved using oligonucleotide-directed mutagenesis to generate site-specific mutations in any cloned DNA of interest. Oligonucleotide mutagenesis is described in, for example, Reidhaar-Olson et al., Science, 241: 53-57 (1988). Briefly, in such procedures a plurality of double stranded oligonucleotides bearing one or more mutations to be introduced into the cloned DNA are synthesized and inserted into the cloned DNA to be mutagenized (e.g., a polynucleotide sequence encoding a CAR polypeptide). Clones containing the mutagenized DNA are recovered, and the activities of the polypeptides they encode are assessed. Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, for example, U.S. Pat. No. 5,965,408. Still another method of generating variants is sexual PCR mutagenesis. In sexual PCR mutagenesis, forced homologous recombination occurs between DNA molecules of different, but highly related, DNA sequences in vitro as a result of random fragmentation of the DNA molecule based on sequence homology. This is followed by fixation of the crossover by primer extension in a PCR reaction. Sexual PCR mutagenesis is described in, for example, Stemmer, Proc. Natl. Acad. Sci., U.S.A., 91: 10747-10751 (1994). Variants can also be created by in vivo mutagenesis. In some embodiments, random mutations in a nucleic acid sequence are generated by propagating the sequence in a bacterial strain, such as an *E. coli* strain, which carries mutations in one or more of the DNA repair pathways. Such "mutator" strains have a higher random mutation rate than that of a wild-type strain. Propagating a DNA sequence (e.g., a polynucleotide sequence encoding a CAR polypeptide) in one of these strains will eventually generate random mutations within the DNA. Mutator strains suitable for use for in vivo mutagenesis are described in, for example, International Patent Application Publication No. WO1991/016427. Variants can also be generated using cassette mutagenesis. In cassette mutagenesis, a small region of a double-stranded DNA molecule is replaced with a synthetic oligonucleotide "cassette" that differs from the native sequence. The oligonucleotide often contains a completely and/or partially randomized native sequence. Recursive ensemble mutagenesis can also be used to generate variants. Recursive ensemble mutagenesis is an algorithm for protein engineering (i.e., protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in, for example, Arkin et al., Proc. Natl. Acad. Sci., U.S.A., 89: 7811-7815 (1992). In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in, for example, Delegrave et al., Biotech. Res, 11: 1548-1552 (1993). In some embodiments, variants are created using shuffling procedures wherein portions of a plurality of nucleic acids that encode distinct polypeptides are fused together to create chimeric nucleic acid sequences that encode chimeric polypeptides as described in, for example, U.S. Pat. Nos. 5,965,408 and 5,939,250. Insertional mutagenesis is mutagenesis of DNA by the insertion of one or more bases. Insertional mutations can occur naturally, mediated by virus or transposon, or can be artificially created for research purposes in the lab, e.g., by transposon mutagenesis. When exogenous DNA is integrated into that of the host, the severity of any ensuing mutation depends entirely on the location within the host's genome wherein the DNA is inserted. For example, significant effects may be evident if a transposon inserts in the middle of an essential gene, in a promoter region, or into a repressor or an enhancer region. Transposon mutagenesis and high-throughput screening was done to find beneficial mutations that increase the titer or yield of a fatty acid derivative or derivatives.

Culture Recombinant Host Cells and Cell Cultures/Fermentation

As used herein, the term "fermentation" broadly refers to the conversion of organic materials into target substances by host cells, for example, the conversion of a carbon source by recombinant host cells into fatty acids or derivatives thereof by propagating a culture of the recombinant host cells in a media comprising the carbon source. As used herein, the term "conditions permissive for the production" means any conditions that allow a host cell to produce a desired product, such as a fatty acid or a fatty acid derivative. Similarly, the term "conditions in which the polynucleotide sequence of a vector is expressed" means any conditions that allow a host cell to synthesize a polypeptide. Suitable conditions include, for example, fermentation conditions. Fermentation conditions can comprise many parameters, including but not limited to temperature ranges, levels of aeration, feed rates and media composition. Each of these conditions, individually and in combination, allows the host cell to grow. Fermentation can be aerobic, anaerobic, or variations thereof (such as micro-aerobic). Exemplary culture media include broths or gels. Generally, the medium includes a carbon source that can be metabolized by a host cell directly. In addition, enzymes can be used in the medium to facilitate the mobilization (e.g., the depolymerization of starch or cellulose to fermentable sugars) and subsequent metabolism of the carbon source. For small scale production, the engineered host cells can be grown in batches of, for example, about 100 mL, 500 mL, 1 L, 2 L, 5 L, or 10 L; fermented; and induced to express a desired polynucleotide sequence, such as a polynucleotide sequence encoding a CAR polypeptide. For large scale production, the engineered host cells can be grown in batches of about 10 L, 100 L, 1000 L, 10,000 L, 100,000 L, and 1,000,000 L or larger; fermented; and induced to express a desired polynucleotide sequence. Alternatively, large scale fed-batch fermentation may be carried out. The fatty acid derivative compositions described herein are found in the extracellular environment of the recombinant host cell culture and can be readily isolated from the culture medium. A fatty acid derivative may be secreted by the recombinant host cell, transported into the extracellular environment or passively transferred into the extracellular environment of the recombinant host cell culture. The fatty acid derivative is isolated from a recombinant host cell culture using routine methods known in the art.

Products Derived From Recombinant Host Cells

As used herein, "fraction of modern carbon" or fM has the same meaning as defined by National Institute of Standards and Technology (NIST) Standard Reference Materials (SRMs4990B and 4990C, known as oxalic acids standards HOxI and HOxII, respectively. The fundamental definition relates to 0.95 times the 14C/12C isotope ratio HOxI (referenced to AD 1950). This is roughly equivalent to decay-corrected pre-Industrial Revolution wood. For the current living biosphere (plant material), fM is approximately 1.1. Bioproducts (e.g., the fatty acid derivatives produced in accordance with the present disclosure) comprising biologically produced organic compounds, and in particular, the fatty acid derivatives produced using the fatty acid biosynthetic pathway herein, have not been produced from renewable sources and, as such, are new compositions of matter. These new bioproducts can be distinguished from organic compounds derived from petrochemical carbon on the basis of dual carbon-isotopic fingerprinting or $^{14}C$ dating. Additionally, the specific source of biosourced carbon (e.g., glucose vs. glycerol) can be determined by dual carbon-isotopic fingerprinting (see, e.g., U.S. Pat. No. 7,169,588, which is herein incorporated by reference). The ability to distinguish bioproducts from petroleum based organic compounds is beneficial in tracking these materials in commerce. For example, organic compounds or chemicals comprising both biologically based and petroleum based carbon isotope profiles may be distinguished from organic compounds and chemicals made only of petroleum based materials. Hence, the bioproducts herein can be followed or tracked in commerce on the basis of their unique carbon isotope profile. Bioproducts can be distinguished from petroleum based organic compounds by comparing the stable carbon isotope ratio ($^{13}C/^{12}C$) in each sample. The $^{13}C/^{12}C$ ratio in a given bioproduct is a consequence of the $^{13}C/^{12}C$ ratio in atmospheric carbon dioxide at the time the carbon dioxide is fixed. It also reflects the precise metabolic pathway. Regional variations also occur. Petroleum, C3 plants (the broadleaf), C4 plants (the grasses), and marine carbonates all show significant differences in $^{13}C/^{12}C$ and the corresponding $\delta^{13}C$ values. Furthermore, lipid matter of C3 and C4 plants analyze differently than materials derived from the carbohydrate components of the same plants as a consequence of the metabolic pathway. Within the precision of measurement, $^{13}C$ shows large variations due to isotopic fractionation effects, the most significant of which for bioproducts is the photosynthetic mechanism. The major cause of differences in the carbon isotope ratio in plants is closely associated with differences in the pathway of photosynthetic carbon metabolism in the plants, particularly the reaction occurring during the primary carboxylation (i.e., the initial fixation of atmospheric $CO_2$). Two large classes of vegetation are those that incorporate the "C3" (or Calvin-Benson) photosynthetic cycle and those that incorporate the "C4" (or Hatch-Slack) photosynthetic cycle. In C3 plants, the primary $CO_2$ fixation or carboxylation reaction involves the enzyme ribulose-1,5-diphosphate carboxylase, and the first stable product is a 3-carbon compound. C3 plants, such as hardwoods and conifers, are dominant in the temperate climate zones. In C4 plants, an additional carboxylation reaction involving another enzyme, phosphoenol-pyruvate carboxylase, is the primary carboxylation reaction. The first stable carbon compound is a 4-carbon acid that is subsequently decarboxylated. The $CO_2$ thus released is refixed by the C3 cycle. Examples of C4 plants are tropical grasses, corn, and sugar cane. Both C4 and C3 plants exhibit a range of $^{13}C/^{12}C$ isotopic ratios, but typical values are about −7 to about −13 per mil for C4 plants and about −19 to about −27 per mil for C3 plants (see, e.g., Stuiver et al., Radiocarbon 19:355 (1977)). Coal and petroleum fall generally in this latter range. The 13C measurement scale was originally defined by a zero set by Pee Dee Belemnite (PDB) limestone, where values are given in parts per thousand deviations from this material. The "δ13C" values are expressed in parts per thousand (per mil), abbreviated, ‰, and are calculated as follows:

$$\delta^{13}C(‰)=[(^{13}C/^{12}C)sample-(^{13}C/^{12}C)standard]/(^{13}C/^{12}C)standard \times 1000$$

Since the PDB reference material (RM) has been exhausted, a series of alternative RMs have been developed in cooperation with the IAEA, USGS, NIST, and other selected international isotope laboratories. Notations for the per mil deviations from PDB is $\delta^{13}C$. Measurements are made on $CO_2$ by high precision stable ratio mass spectrometry (IRMS) on molecular ions of masses 44, 45, and 46. The compositions described herein include bioproducts produced by any of the methods described herein, including, for example, fatty aldehyde and alcohol products. Specifically, the bioproduct can have a $\delta^{13}C$ of about −28 or greater, about −27 or greater, −20 or greater, −18 or greater, −15 or greater, −13 or greater, −10 or greater, or −8 or greater. For example, the bioproduct can have a $\delta^{13}C$ of about −30 to about −15, about −27 to about −19, about −25 to about −21, about −15 to about −5, about −13 to about −7, or about −13 to about −10. In other instances, the bioproduct can have a $\delta^{13}C$ of about −10, −11, −12, or −12.3. Bioproducts produced in accordance with the disclosure herein, can also be distinguished from petroleum based organic compounds by comparing the amount of $^{14}C$ in each compound. Because $^{14}C$ has a nuclear half-life of 5730 years, petroleum based fuels containing "older" carbon can be distinguished from bioproducts which contain "newer" carbon (see, e.g., Currie, "Source Apportionment of Atmospheric Particles", Characterization of Environmental Particles, J. Buffle and H. P. van Leeuwen, Eds., 1 of Vol. I of the IUPAC Environmental Analytical Chemistry Series (Lewis Publishers, Inc.) 3-74, (1992)). The basic assumption in radiocarbon dating is that the constancy of $^{14}C$ concentration in the atmosphere leads to the constancy of $^{14}C$ in living organisms. However, because of atmospheric nuclear testing since 1950 and the burning of fossil fuel since 1850, $^{14}C$ has acquired a second, geochemical time characteristic. Its concentration in atmospheric $CO_2$, and hence in the living biosphere, approximately doubled at the peak of nuclear testing, in the mid-1960s. It has since been gradually returning to the steady-state cosmogenic (atmospheric) baseline isotope rate ($^{14}C/^{12}C$) of about 1.2×10-12, with an approximate relaxation "half-life" of 7-10 years. (This latter half-life must not be taken literally; rather, one must use the detailed atmospheric nuclear input/decay function to trace the variation of atmospheric and biospheric $^{14}C$ since the onset of the nuclear age.) It is this latter biospheric $^{14}C$ time characteristic that holds out the promise of annual dating of recent biospheric carbon. $^{14}C$ can be measured by accelerator mass spectrometry (AMS), with results given in units of "fraction of modern carbon" (fM). fM is defined by National Institute of Standards and Technology (NIST) Standard Reference Materials (SRMs) 4990B and 4990C. As used herein, "fraction of modern carbon" or "fM" has the same meaning as defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), fM is approximately 1.1. The compositions described herein include bioproducts that can have an fM $^{14}C$ of at least about 1. For example, the bioproduct of the disclosure can have an fM $^{14}$C of at least about 1.01, an fM $^{14}$C of about 1 to about 1.5, an fM $^{14}$C of about 1.04 to about 1.18, or an fM $^{14}$C of about 1.111 to about 1.124.

Another measurement of $^{14}$C is known as the percent of modern carbon (pMC). For an archaeologist or geologist using $^{14}$C dates, AD 1950 equals "zero years old". This also represents 100 pMC. "Bomb carbon" in the atmosphere reached almost twice the normal level in 1963 at the peak of thermo-nuclear weapons. Its distribution within the atmosphere has been approximated since its appearance, showing values that are greater than 100 pMC for plants and animals living since AD 1950. It has gradually decreased over time with today's value being near 107.5 pMC. This means that a fresh biomass material, such as corn, would give a 14C signature near 107.5 pMC. Petroleum based compounds will have a pMC value of zero. Combining fossil carbon with present day carbon will result in a dilution of the present day pMC content. By presuming 107.5 pMC represents the $^{14}$C content of present day biomass materials and 0 pMC represents the $^{14}$C content of petroleum based products, the measured pMC value for that material will reflect the proportions of the two component types. For example, a material derived 100% from present day soybeans would give a radiocarbon signature near 107.5 pMC. If that material was diluted 50% with petroleum based products, it would give a radiocarbon signature of approximately 54 pMC. A biologically based carbon content is derived by assigning "100%" equal to 107.5 pMC and "0%" equal to 0 pMC. For example, a sample measuring 99 pMC will give an equivalent biologically based carbon content of 93%. This value is referred to as the mean biologically based carbon result and assumes all the components within the analyzed material originated either from present day biological material or petroleum based material. A bioproduct comprising one or more fatty acid derivatives as described herein can have a pMC of at least about 50, 60, 70, 75, 80, 85, 90, 95, 96, 97, 98, 99, or 100. In other instances, a fatty acid derivative described herein can have a pMC of between about 50 and about 100; about 60 and about 100; about 70 and about 100; about 80 and about 100; about 85 and about 100; about 87 and about 98; or about 90 and about 95. In yet other instances, a fatty acid derivative described herein can have a pMC of about 90, 91, 92, 93, 94, or 94.2.

Screening Fatty Acid Derivative Compositions Produced by Recombinant Host Cells

To determine if conditions are sufficient to allow expression, a host cell can be cultured, for example, for about 4, 8, 12, 24, 36, or 48 hours. During and/or after culturing, samples can be obtained and analyzed to determine if the conditions allow expression. For example, the host cells in the sample or the medium in which the host cells were grown can be tested for the presence of a desired product. When testing for the presence of a product, assays, such as, but not limited to, TLC, HPLC, GC/FID, GC/MS, LC/MS, MS, can be used. Recombinant host cell cultures are screened at the 96 well plate level, 1 liter and 5 liter tank level and in a 1000 L pilot plant using a GC/FID assay for "total fatty species".

Utility of Fatty Acid Derivative Compositions

A fatty acid is a carboxylic acid with a long aliphatic tail (chain), which is either saturated or unsaturated. Most naturally occurring fatty acids have a chain of an even number of carbon atoms, from 4 to 28. Fatty acids are usually derived from triglycerides. When they are not attached to other molecules, they are known as "free" fatty acids. Fatty acids are usually produced industrially by the hydrolysis of triglycerides, with the removal of glycerol.

Palm, soybean, rapeseed, coconut oil and sunflower oil are currently the most common sources of fatty acids. The majority of fatty acids derived from such sources are used in human food products. Coconut oil and palm kernel oil (consist mainly of 12 and 14 carbon fatty acids). These are particularly suitable for further processing to surfactants for washing and cleansing agents as well as cosmetics. Palm, soybean, rapeseed, and sunflower oil, as well as animal fats such as tallow, contain mainly long-chain fatty acids (e.g., C18, saturated and unsaturated) which are used as raw materials for polymer applications and lubricants. Ecological and toxicological studies suggest that fatty acid-derived products based on renewable resources have more favorable properties than petrochemical-based substances. Fatty aldehydes are used to produce many specialty chemicals. For example, aldehydes are used to produce polymers, resins (e.g., Bakelite), dyes, flavorings, plasticizers, perfumes, pharmaceuticals, and other chemicals, some of which may be used as solvents, preservatives, or disinfectants. In addition, certain natural and synthetic compounds, such as vitamins and hormones, are aldehydes, and many sugars contain aldehyde groups. Fatty aldehydes can be converted to fatty alcohols by chemical or enzymatic reduction. Fatty alcohols have many commercial uses. Worldwide annual sales of fatty alcohols and their derivatives are in excess of U.S. $1 billion. The shorter chain fatty alcohols are used in the cosmetic and food industries as emulsifiers, emollients, and thickeners. Due to their amphiphilic nature, fatty alcohols behave as nonionic surfactants, which are useful in personal care and household products, such as, for example, detergents. In addition, fatty alcohols are used in waxes, gums, resins, pharmaceutical salves and lotions, lubricating oil additives, textile antistatic and finishing agents, plasticizers, cosmetics, industrial solvents, and solvents for fats. The disclosure also provides a surfactant composition or a detergent composition comprising a fatty alcohol produced by any of the methods described herein. One of ordinary skill in the art will appreciate that, depending upon the intended purpose of the surfactant or detergent composition, different fatty alcohols can be produced and used. For example, when the fatty alcohols described herein are used as a feedstock for surfactant or detergent production, one of ordinary skill in the art will appreciate that the characteristics of the fatty alcohol feedstock will affect the characteristics of the surfactant or detergent composition produced. Hence, the characteristics of the surfactant or detergent composition can be selected for by producing particular fatty alcohols for use as a feedstock. A fatty alcohol-based surfactant and/or detergent composition described herein can be mixed with other surfactants and/or detergents well known in the art. In some embodiments, the mixture can include at least about 10%, at least about 15%, at least about 20%, at least about 30%, at least about 40%, at least about 50%, at least about 60%, or a range bounded by any two of the foregoing values, by weight of the fatty alcohol. In other examples, a surfactant or detergent composition can be made that includes at least about 5%, at least about 10%, at least about 20%, at least about 30%, at least about 40%, at least about 50%, at least about 60%, at least about 70%, at least about 80%, at least about 85%, at least about 90%, at least about 95%, or a range bounded by any two of the foregoing values, by weight of a fatty alcohol that includes a carbon chain that is 8, 9, 10, 11, 12, 13, 14, 15, 16, 17, 18, 19, 20, 21, or 22 carbons in length. Such surfactant or detergent compositions also can include at least one additive, such as a microemulsion or a surfactant or detergent from non-microbial sources such as plant oils or petroleum, which can be present in the amount of at least about 5%, at least about 10%, at least about 15%, at least about 20%, at least about 30%, at least about 40%, at least about 50%, at least about 60%, at least about 70%, at least about 80%, at least about 85%, at least about 90%, at least about 95%, or a range bounded by any two of the foregoing values, by weight of the fatty alcohol. Esters have many commercial uses. For example, biodiesel, an alternative fuel, is comprised of esters (e.g., fatty acid methyl esters, fatty acid ethyl esters, etc.). Some low molecular weight esters are volatile with a pleasant odor, which makes them useful as fragrances or flavoring agents. In addition, esters are used as solvents for lacquers, paints, and varnishes. Furthermore, some naturally occurring substances, such as waxes, fats, and oils are comprised of esters. Esters are also used as softening agents in resins and plasticizers, flame retardants, and additives in gasoline and oil. In addition, esters can be used in the manufacture of polymers, films, textiles, dyes, and pharmaceuticals. Hydrocarbons have many commercial uses. For example, shorter chain alkanes are used as fuels. Longer chain alkanes (e.g., from five to sixteen carbons) are used as transportation fuels (e.g., gasoline, diesel, or aviation fuel). Alkanes having more than sixteen carbon atoms are important components of fuel oils and lubricating oils. Even longer alkanes, which are solid at room temperature, can be used, for example, as a paraffin wax. In addition, longer chain alkanes can be cracked to produce commercially valuable shorter chain hydrocarbons. Like short chain alkanes, short chain alkenes are used in transportation fuels. Longer chain alkenes are used in plastics, lubricants, and synthetic lubricants. In addition, alkenes are used as a feedstock to produce alcohols, esters, plasticizers, surfactants, tertiary amines, enhanced oil recovery agents, fatty acids, thiols, alkenylsuccinic anhydrides, epoxides, chlorinated alkanes, chlorinated alkenes, waxes, fuel additives, and drag flow reducers. Ketones are used commercially as solvents. For example, acetone is frequently used as a solvent, but it is also a raw material for making polymers. Ketones are also used in lacquers, paints, explosives, perfumes, and textile processing. In addition, ketones are used to produce alcohols, alkenes, alkanes, imines, and enamines. Lubricants are typically composed of olefins, particularly polyolefins and alpha-olefins. Lubricants can either be refined from crude petroleum or manufactured using raw materials refined from crude petroleum. Obtaining these specialty chemicals from crude petroleum requires a significant financial investment as well as a great deal of energy. It is also an inefficient process because frequently the long chain hydrocarbons in crude petroleum are cracked to produce smaller monomers. These monomers are then used as the raw material to manufacture the more complex specialty chemicals. The disclosure is further illustrated by the following examples. The examples are provided for illustrative purposes only. They are not to be construed as limiting the scope or content of the disclosure in any way.

EXAMPLES

Example 1

Production Host Modifications—Attenuation of Acyl-CoA Dehydrogenase

This example describes the construction of a genetically engineered host cell wherein the expression of a fatty acid degradation enzyme is attenuated.

The fadE gene of *Escherichia coli* MG1655 (an *E. coli* K strain) was deleted using the Lambda Red (also known as the Red-Driven Integration) system described by Datsenko et al., Proc. Natl. Acad. Sci. USA 97: 6640-6645 (2000), with the following modifications:

The following two primers were used to create the deletion of fadE:

```
Del-fadE-F
                                    (SEQ ID NO: 9)
5'-AAAAACAGCAACAATGTGAGCTTTGTTGTAATTATATTGTAAACATA TTGATTCCGGGGATCCGTCGACC;
and Del-fadE-R
                                    (SEQ ID NO: 10)
5'-AAACGGAGCCTTTCGGCTCCGTTATTCATTTACGCGGCTTCAACTTT

CCTGTAGGCTGGAGCTGCTTC
```

The Del-fadE-F and Del-fadE-R primers were used to amplify the kanamycin resistance (KmR) cassette from plasmid pKD13 (described by Datsenko et al., supra) by PCR. The PCR product was then used to transform electrocompetent *E. coli* MG1655 cells containing pKD46 (described in Datsenko et al., supra) that had been previously induced with arabinose for 3-4 hours. Following a 3-hour outgrowth in a super optimal broth with catabolite repression (SOC) medium at 37° C., the cells were plated on Luria agar plates containing 50 μg/mL of Kanamycin. Resistant colonies were identified and isolated after an overnight incubation at 37° C. Disruption of the fadE gene was confirmed by PCR amplification using primers fadE-L2 and fadE-R1, which were designed to flank the *E. coli* fadE gene.

The fadE deletion confirmation primers were:

```
    fadE-L2
                                    (SEQ ID NO: 11)
    5'-CGGGCAGGTGCTATGACCAGGAC;
    and fadE-R1
                                    (SEQ ID NO: 12)
    5'-CGCGGCGTTGACCGGCAGCCTGG
```

Figure 7:
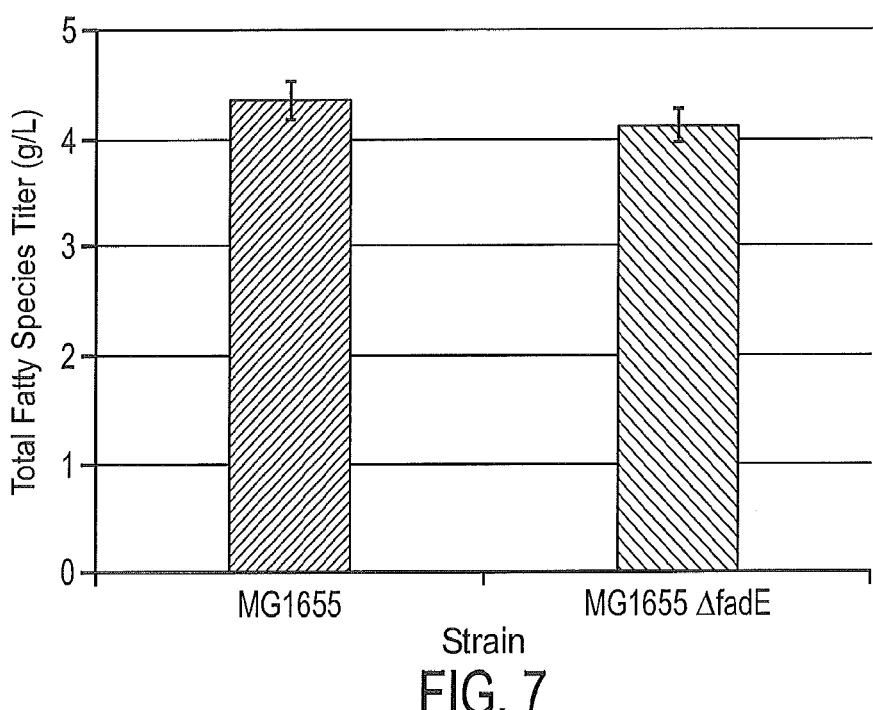
FIG. 7 illustrates fatty acid derivative (Total Fatty Species) production by the MG1655 E. coli strain with the fadE gene attenuated (i.e., deleted) compared to fatty acid derivative production by E. coli MG1655. The data presented in FIG. 7 shows that attenuation of the fadE gene did not affect fatty acid derivative production.

After the fadE deletion was confirmed, a single colony was used to remove the KmR marker using the pCP20 plasmid as described by Datsenko et al., supra. The resulting MG1655 *E. coli* strain with the fadE gene deleted and the KmR marker removed was named *E. coli* MG1655 ΔfadE, or *E. coli* MG 1655 D1. Fatty acid derivative (total fatty species) production by the MG1655 *E. coli* strain with the fadE gene deleted was compared to fatty acid derivative production by *E. coli* MG1655. The deletion of the fadE gene did not affect fatty acid derivative production (FIG. 7). A number of exemplary host cell strains are described herein, examples of which are described below in Table 3.

TABLE 3

| Genetic Characterization of *E. coli* Strains | |
| --- | --- |
| Strain | Genetic Characterization |
| DV2 | MG1655 F−, λ−, ilvG−, rfb-50, rph-1, ΔfhuA::FRT, ΔfadE::FRT |
| DV2.1 | DV2 fabB::fabB[A329V] |
| D178 | DV2.1 entD::FRT_P$_{T5}$_entD |
| EG149 | D178 ΔinsH-11::(P$_{LACUV5}$-iFAB138 |
| V642 | EG149 rph+ |
| SL313 | V642 lacIZ::P$_{A1}$_'tesA/pDG109 |
| V668 | V642 ilvG+ |

TABLE 3-continued

| Genetic Characterization of *E. coli* Strains | |
| --- | --- |
| Strain | Genetic Characterization |
| LC397 | V668 lacIZ::P$_{TRC}$_'tesA(var)_kan |
| SL571 | V668 lacIZ:: P$_{TRC}$_'tesA(var)_FRT |
| LC942 | SL571 attTn7::P$_{TRC}$_'tesA(var) |
| DG16 | LC942/pLC56 |
| V940 | LC397/pV171.1 |
| D851 | SL571 yijP::Tn5-cat/pV171.1 |
| BD64 | DV2 ΔinsH-11::P$_{LACUV5}$-iFAB138 loxP_P$_{TS}$_fadR |
| DAM1 | DV2 attTn7::P$_{TRC}$_tesA_fadD |
| Shu.002 | DV2 ΔinsH-11::P$_{TS}$-iFAB138 loxP_P$_{TS}$_fadR |

Plasmids: pDG109, pLC56 and pV171.1 both are pCL_P$_{trc}$_carB_tesA_alrA_fabB_fadR operon with variable expression of carB and tesA. iFAB138 is SEQ ID NO: 19.

Example 2

Figure 3:
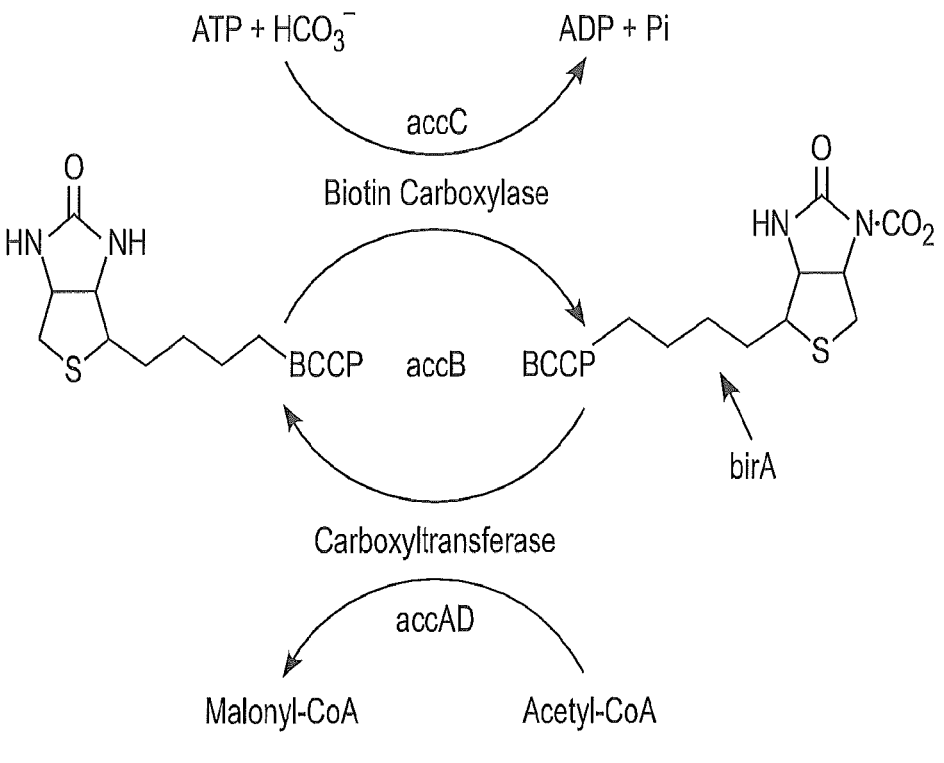
FIG. 3 illustrates the structure and function of the acetyl-CoA carboxylase (accABCD) enzyme complex. BirA biotinylates accB, the biotin carboxyl carrier protein, which is part of the acetyl-CoA carboxylase enzyme complex.

Increased Flux Through the Fatty Acid Synthesis Pathway—
Acetyl CoA Carboxylase Mediated
Fatty Ester Production:

The main precursors for fatty acid biosynthesis are malonyl-CoA and acetyl-CoA (FIG. 1). It has been suggested that these precursors limit the rate of fatty acid biosynthesis in *E. coli*. In this example, synthetic acc operons [*Corynebacterium glutamicum* accABCD (±birA)] were overexpressed and the genetic modifications led to increased acetyl-coA and malonyl-CoA production in *E. coli*. In one approach, in order to increase malonyl-CoA levels, an acetyl-CoA carboxylase enzyme complex from *Corynebacterium glutamicum* (*C. glutamicum*) was overexpressed in *E. coli*. Acetyl-CoA carboxylase (acc) consists of four discrete subunits, accA, accB, accC and accD (FIG. 3). The advantage of *C. glutamicum* acc is that two subunits are expressed as fusion proteins, accCB and accDA, respectively, which facilitates its balanced expression. Additionally, *C. glutamicum* birA, which biotinylates the accB subunit (FIG. 3) was overexpressed. Exemplary *C. glutamicum* birA DNA sequences are presented as SEQ ID NO: 55 and SEQ ID NO: 56. A *C. glutamicum* birA protein sequence is presented as SEQ ID NO: 57.

Figure 8:
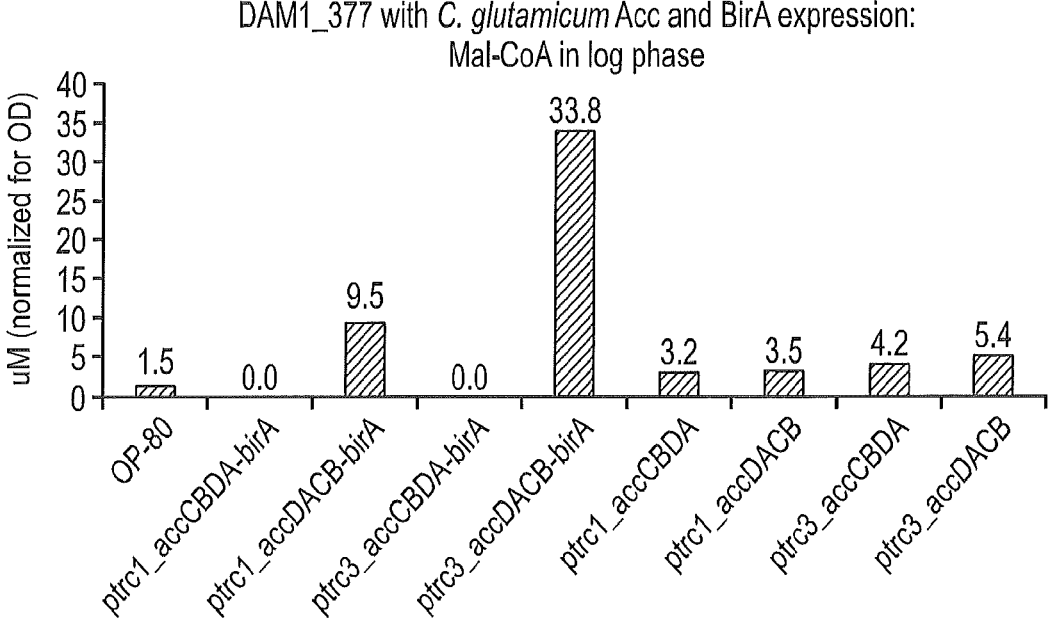
FIG. 8 shows malonyl-CoA levels in DAM1_i377 in log phase, expressing eight different C. glutamicum acetyl-CoA carboxylase (Acc) operon constructs.

The synthetic operons of the *C. glutamicum* acc genes were cloned in the following way in OP80 (see WO2008/119082 as incorporated-by-reference herein) Ptrc1-accDACB, Ptrc3-accDACB, Ptrc1-accCBDA and Ptrc3-CBDA. Ptrc1 and Ptrc3 are derivatives of the commonly used Ptrc promoter, which allow attenuated transcription of target genes. Note that the native sequences were amplified from the chromosomal DNA as they showed favorable codon usage (only the codon for Arg6 in accCB was changed). The *C. glutamicum* birA gene was codon optimized and obtained by gene synthesis. It was cloned downstream of the acc genes in all four operon constructs. Below we refer to the operon configuration accDACB as accD- and the operon configuration accDACB+birA as accD+. The resulting plasmids were transformed into *E. coli* DAM1_i377, which contains integrated copies (i) of leaderless thioesterase 'tesA and acyl-CoA synthetase fadD from *E. coli* and Ester synthase 9 (ES9) from *Marinobacter hydrocarbonoclasticus* (SEQ ID NO: 6). All genes are controlled by Ptrc promoters. The strains were grown in 5NBT media (described below) in shake flasks and were analyzed for malonyl-CoA using short chain-CoA assay described below. FIG. 8 shows that six of the eight *C. glutamicum* acc±birA constructs showed elevated levels of malonyl-CoA in logarithmic phase demonstrating their functionality in *E. coli*. It was noted that coexpression of birA further increased malonyl-CoA levels in the ptrc1/3_accDACB strains, in particular with the plasmid containing the Ptrc3-accDACB-birA operon configuration (plasmid pAS119.50 D; SEQ ID NO: 62).

Figure 9:
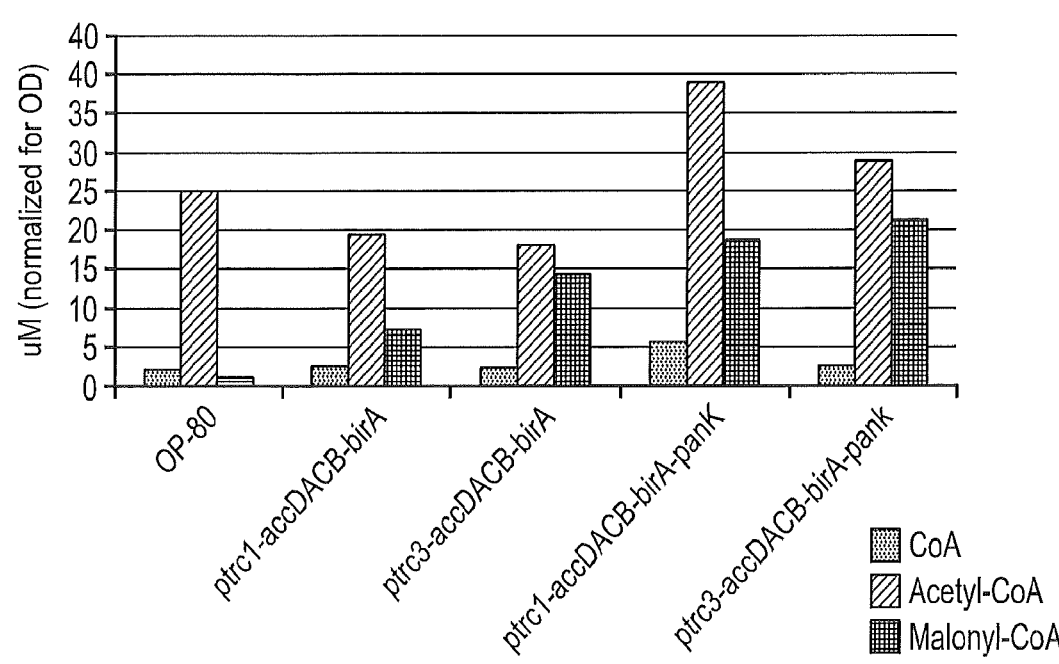
FIG. 9 shows intracellular short chain-CoA levels in E. coli DAM1_i377 in log phase expressing ptrc1/3_acc-DACB-birA±panK operon constructs. accDACB+birA is also referred to herein as accD+.

In order to test the effect of combining panK and acc-birA overexpression, the optimized panK gene was cloned downstream of birA in ptrc1/3_accDACB-birA. Pantothenate kinase panK (or CoaA) catalyzes the first step in the biosynthesis of coenzyme A, an essential cofactor that is involved in many reactions, e.g., the formation of acetyl-CoA, the substrate for acetyl-CoA carboxylase. The resulting plasmids were transformed into DAM1_i377, grown in 5NBT (+TVS1) media in shake flasks, and the strains were analyzed for short-chain-CoAs using the method described below. As shown in FIG. 9, in log phase panK coexpression further increased malonyl-CoA levels and also increased acetyl-CoA levels demonstrating that panK can further increase the malonyl-CoA levels. The impact of coexpressing an acetyl-CoA carboxylase enzyme complex on fatty ester production was evaluated by expressing ester synthase 9 (SEQ ID NO: 6) with and without acc genes in another *E. coli* production host. More specifically, plasmids OP80 (vector control), pDS57 (with ES9), pDS57-accD- (with ES9 and accDACB) or pDS57-accD+ (with ES9 and accDACB-birA; SEQ ID NO: 63) were transformed into *E. coli* strain DV2 and the corresponding transformants were selected on LB plates supplemented with 100 mg/L of spectinomycin.

Figure 10:
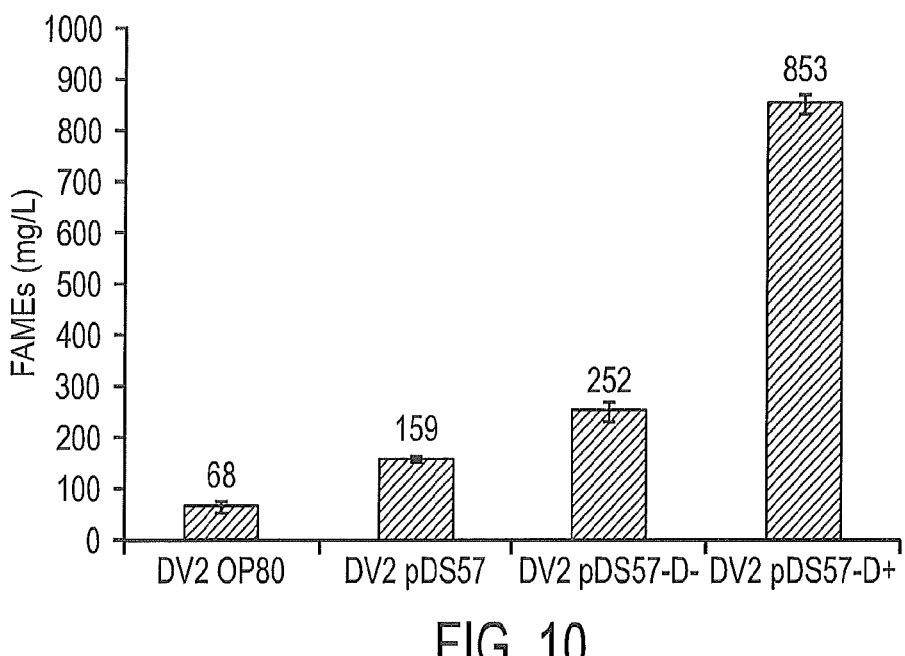
FIG. 10 shows fatty acid methyl ester (FAME) production in E. coli strain DV2 expressing ester synthase 9 from M. hydrocarbonoclasticus and components of an acetyl-CoA carboxylase complex from C. glutamicum.

Two transformants of each plasmid were independently inoculated into LB medium supplemented with 100 mg/L of spectinomycin and grown for 5-8 hours at 32° C. The cultures were diluted 30-fold into a minimal medium with the following composition: 0.5 g/L NaCl, 1 mM MgSO$_4$×7 H$_2$O, 0.1 mM CaCl$_2$), 2 g/L NH$_4$Cl, 3 g/L KH$_2$PO$_4$, 6 g/L Na$_2$HPO$_4$, 1 mg/L thiamine, 1× trace metal solution, 10 mg/L ferric citrate, 100 mM Bis-Tris (pH7.0), 30 g/L glucose and 100 mg/L spectinomycin. After over-night growth at 32° C., the cultures were diluted 10-fold in quadruplicate into minimal medium of the same composition except that the media contained 1 g/L instead of 2 g/L NH$_4$Cl and was supplemented with 1 mM IPTG and 2% (v/v) methanol. The resulting cultures were then grown at 32° C. in a shaker. The production of fatty acid methyl esters (FAMEs) was analyzed by gas chromatography with flame ionization detector (GC-FID). The samples were extracted with butyl acetate in a ratio of 1:1 vol/vol. After vortexing, the samples were centrifuged, and the organic phase was analyzed by gas chromatography (GC). The analysis conditions were as follows: instrument: Trace GC Ultra, Thermo Electron Corporation with Flame ionization detector (FID) detector; column: DB-1 (1% diphenyl siloxane; 99% dimethyl siloxane) CO1 UFM 1/0.1/5 01 DET from Thermo Electron Corporation, phase pH 5, FT: 0.4 μm, length 5 m, id: 0.1 mm; inlet conditions: 250° C. splitless, 3.8 m ⅕s split method used depending upon sample concentration with split flow of 75 mL/m; carrier gas, flow rate: Helium, 3.0 mL/m; block temperature: 330° C.; oven temperature: 0.5 m hold at 50° C., 100° C./m to 330° C., 0.5 m hold at 330° C.; detector temperature: 300° C.; injection volume: 2 μL; run time/flow rate: 6.3 m/3.0 mL/m (splitless method), 3.8 m/1.5 mL/m (split ⅕s method), 3.04 m/1.2 mL/m (split ⅕0 method). FAMEs produced are shown in FIG. 10. The expression of ES9 by itself in *E. coli* DV2 led to FAME production above the control DV2 OP80. Coexpression of the *C. glutamicum* acetyl-CoA carboxylase complex led to an approx. 1.5-fold increase in FAMEs and the additional expression of the *C. glutamicum* biotin protein ligase led to an approx. 5-fold increase in FAMEs. These results suggest that the increased supply of malonyl-CoA improves the ability of ES9 to convert intermediates of the fatty acid biosynthetic machinery to fatty acid methyl esters in *E. coli.*

Short-chain-CoA assay: 15 ml falcon tubes were prepared with 0.467 ml 10% TCA with crotonyl-CoA as internal standard and overlayed with 2 ml of silicone oil. The tubes were chilled on ice and fermentation broth equivalent to 1 ml OD600=31.2 was carefully layered on top of the silicone oil. The samples were centrifuged at 11,400 g at 4° C. for four 4 min cycles. For each sample, a 400 ml aliquots of the TCA/cellular extract was removed and placed in a fresh Eppendorf tube for neutralization with 1 ml Octylamine (in CHCl3). After vortexing, the samples were centrifuged for 30 see at 13,000 g. 200 ml of the top layer was filtered using a 0.2 um PTFE syringe filter and then subjected to LC-MS/MS analysis.

Description of Media Used in Experiments:

| Media ID | | | | | | |
|---|---|---|---|---|---|---|
| 4N-BT | 5N-BT | FA2 | FA2.1 | FA2.3 | Concentration | Ingredient |
| 0.5 | 0.5 | 0.5 | 0.5 | 0.5 | g/L | NaCl |
| 2 | 2 | 2 | 2 | 2 | g/L | NH$_4$Cl |
| 3 | 3 | 3 | 3 | 3 | g/L | KH$_2$PO$_4$ |
| 6 | 6 | 6 | 6 | 6 | g/L | Na$_2$PO$_4$ |
| 1 | 1 | 1 | 1 | 1 | mM | MgSO$_4$ |
| 0.1 | 0.1 | 0.1 | 0.1 | 0.1 | mM | CaCl$_2$ |
| 1 | 1 | 1 | 1 | 1 | mg/L | thiamine |
| 0.2 | 0.2 | 0.1 | 0.1 | 0.1 | M | Bis-Tris pH7 |
| 0.1 | 0.1 | 0.05 | 0.1 | 0.1 | % | Triton X-100 |
| 1 | 1 | 1 | 1 | 1 | x | Trace Minerals |
| 27 | 27 | 10 | 10 | 10 | mg/L | FeCl$_2$•6H$_2$O |
| 40 | 50 | 30 | 30 | 35 | g/L | glucose |

Figure 11:
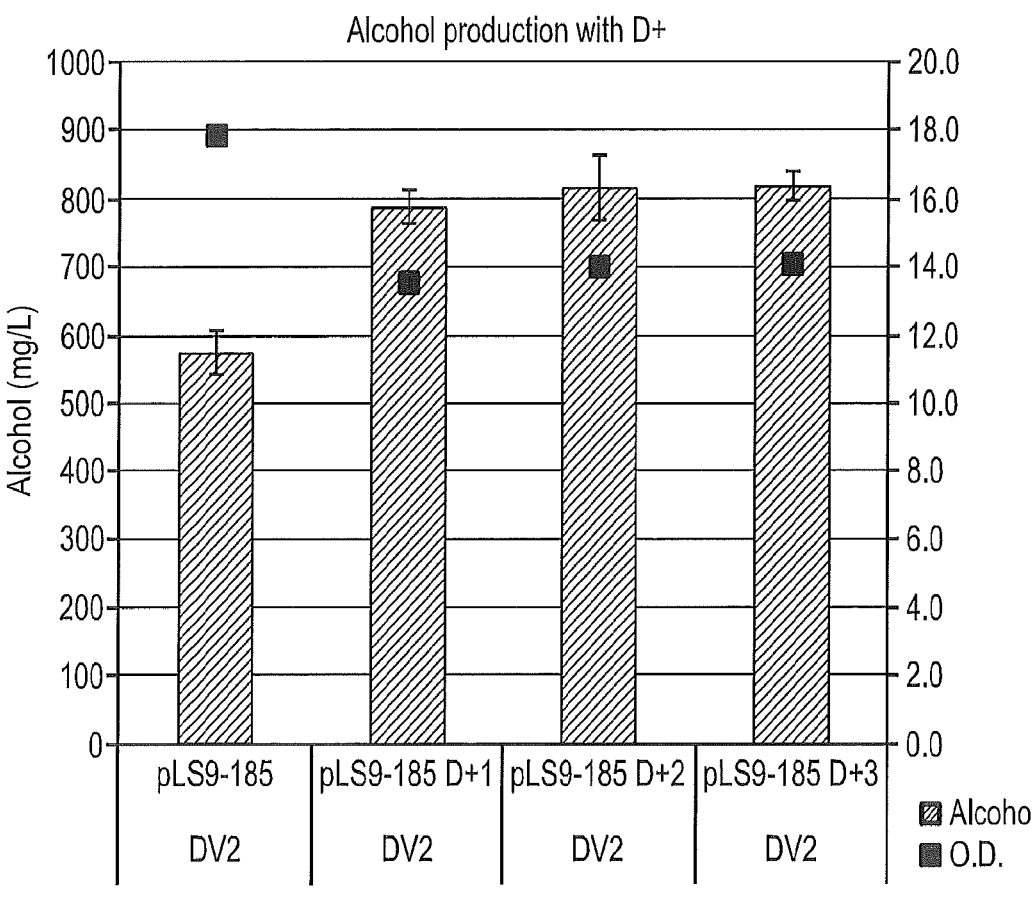
FIG. 11 shows production of fatty alcohols by E. coli expressing the Synechococcus elongatus PCC7942 AAR together with the accD+ operon from C. glutamicum on a pCL plasmid. Triplicate samples are shown for the accD+ strains.

1000 fold concentrated Trace Vitamins Solution
0.06 g/L Riboflavin
6 g/L Niacin
5.4 g/L Pantothenic Acid
1.4 g/L Pyridoxine
0.06 g/L Biotin
0.01 g/L Folic Acid
1000 Fold Concentrated Trace Metal Solution
2 mL/L Concentrated hydrochloric acid
0.5 g/L boric acid
1.9 g/L cupric sulfate, pentahydrate, USP
1 g/L zinc chloride anhydrous
2 g/L sodium molybdenate dehydrate
2 g/L calcium chloride dehydrate
Fatty Alcohol Production:

The impact of coexpressing an acetyl-CoA carboxylase enzyme complex on Fatty alcohol production was evaluated by expressing the Acyl-ACP reductase (AAR) from *Synechococcus elongatus* (SEQ ID NO: 38) with and without acc genes in *E. coli* DV2. The accD+ operon configuration was selected as it gave the best results when coexpressed with ester synthase (see previous example). The accDABC-birA operon was cloned downstream from the aar gene in pLS9-185 (a pCL1920 derivative) using Infusion technology (Clontech Laboratories, Inc., Mountain View, CA). The resulting plasmid was transformed into *E. coli* DV2 and the corresponding transformants were selected on LB plates supplemented with 100 mg/L of spectinomycin. Fatty alcohols produced are shown in FIG. 11. The coexpression of AAR and accD+ led to a ca. 1.5-fold increase in fatty alcohol titers as compared to the AAR only control (pLS9-185). The data were reproducible (triplicate samples were shown). These results demonstrate that increasing malonyl-CoA levels lead to improved fatty acid production when this acyl-ACP reductase is used. In addition, Example 3 describes co-expression of acc genes together with entire fab operons.

Example 3

Increased Flux Through the Fatty Acid Synthesis Pathway—iFABs
Fatty Acid Derivative Production:

Strategies to increase the flux through the fatty acid synthesis pathway in recombinant host cells include both overexpression of native *E. coli* fatty acid biosynthesis genes and expression of exogenous fatty acid biosynthesis genes from different organisms in *E. coli.* In this study, fatty acid biosynthesis genes from different organisms were combined in the genome of *E. coli* DV2 (Table 3) under the control of the lacUV5 promoter and integrated into the IS5-11 site. Sixteen strains containing iFABs 130-145 were evaluated. The detailed structure of iFABs 130-145 is presented in Tables 4 and 5.

TABLE 4

| Components from Different Species used in iFABs 130-145 | |
|---|---|
| Abbreviation | Full Description |
| St_fabD | *Salmonella typhimurium* fabD gene |
| nSt_fabH | *Salmonella typhimurium* FabH gene with the native RBS |
| sSt_fabH | *Salmonella typhimurium* fabH gene with a synthetic RBS |
| Cac_fabF | *Clostridium acetobutylicum* (ATCC824) fabF gene |
| St_fabG | *Salmonella typhimurium* fabG gene |
| St_fabA | *Salmonella typhimurium* fabA gene |
| St_fabZ | *Salmonella typhimurium* fabZ gene |
| BS_fabI | *Bacillus subtilis* fabI gene |
| BS_FabL | *Bacillus subtilis* fabL gene |
| Vc_FabV | *Vibrio chorlerae* fabV gene |
| Ec_FabI | *Escherichia coli* fabI gene |

Each "iFAB" included various fab genes in the following order: 1) an enoyl-ACP reductase (BS_fabI, BS_FabL, Vc_FabV, or Ec_FabI); 2) a β-ketoacyl-ACP synthetase III (St_fabH); 3) a malonyl-CoA-ACP transacylase (St_fabD); 4) a b-ketoacyl-ACP reductase (St_fabG); 5) a 3-hydroxy-acyl-ACP dehydratase (St_fabA or St_fabZ); 6) a β-ketoacyl-ACP synthetase II (Cac_fabF). Note that St_fabA also has trans-2, cis-3-decenoyl-ACP isomerase activity and that Cac_fabF has β-ketoacyl-ACP synthetase II and β-ketoacyl-ACP synthetase I activities (Zhu et al., BMC Microbiology 9:119 (2009)). See Table 5, below for the specific composition of iFABs 130-145.

TABLE 5

| Composition of iFABs 130-145 | | | | | | | | | | | |
|---|---|---|---|---|---|---|---|---|---|---|---|
| ifab | BS_fabI | BS_fabL | Vc_fabV | Ec_fabI | nSt_fabH | sSt_fabH | St_fabD | St_fabG | St_fabA | St_fabZ | Cac_fabF |
| ifab130 | 1 | 0 | 0 | 0 | 1 | 0 | 1 | 1 | 1 | 0 | 1 |
| ifab131 | 1 | 0 | 0 | 0 | 1 | 0 | 1 | 1 | 0 | 1 | 1 |

TABLE 5-continued

| | | | | Composition of iFABs 130-145 | | | | | | |
|---|---|---|---|---|---|---|---|---|---|---|
| ifab | BS_fabI | BS_fabL | Vc_fabV | Ec_fabI | nSt_fabH | sSt_fabH | St_fabD | St_fabG | St_fabA | St_fabZ | Cac_fabF |
| ifab132 | 1 | 0 | 0 | 0 | 0 | 1 | 1 | 1 | 1 | 0 | 1 |
| ifab133 | 1 | 0 | 0 | 0 | 0 | 1 | 1 | 1 | 0 | 1 | 1 |
| ifab134 | 0 | 1 | 0 | 0 | 1 | 0 | 1 | 1 | 1 | 0 | 1 |
| ifab135 | 0 | 1 | 0 | 0 | 1 | 0 | 1 | 1 | 0 | 1 | 1 |
| ifab136 | 0 | 1 | 0 | 0 | 0 | 1 | 1 | 1 | 1 | 0 | 1 |
| ifab137 | 0 | 1 | 0 | 0 | 0 | 1 | 1 | 1 | 0 | 1 | 1 |
| ifab138 | 0 | 0 | 1 | 0 | 1 | 0 | 1 | 1 | 1 | 0 | 1 |
| ifab139 | 0 | 0 | 1 | 0 | 1 | 0 | 1 | 1 | 0 | 1 | 1 |
| ifab140 | 0 | 0 | 1 | 0 | 0 | 1 | 1 | 1 | 1 | 0 | 1 |
| ifab141 | 0 | 0 | 1 | 0 | 0 | 1 | 1 | 1 | 0 | 1 | 1 |
| ifab142 | 0 | 0 | 0 | 1 | 1 | 0 | 1 | 1 | 1 | 0 | 1 |
| ifab143 | 0 | 0 | 0 | 1 | 1 | 0 | 1 | 1 | 0 | 1 | 1 |
| ifab144 | 0 | 0 | 0 | 1 | 0 | 1 | 1 | 1 | 1 | 0 | 1 |
| ifab145 | 0 | 0 | 0 | 1 | 0 | 1 | 1 | 1 | 0 | 1 | 1 |

Figure 12A:
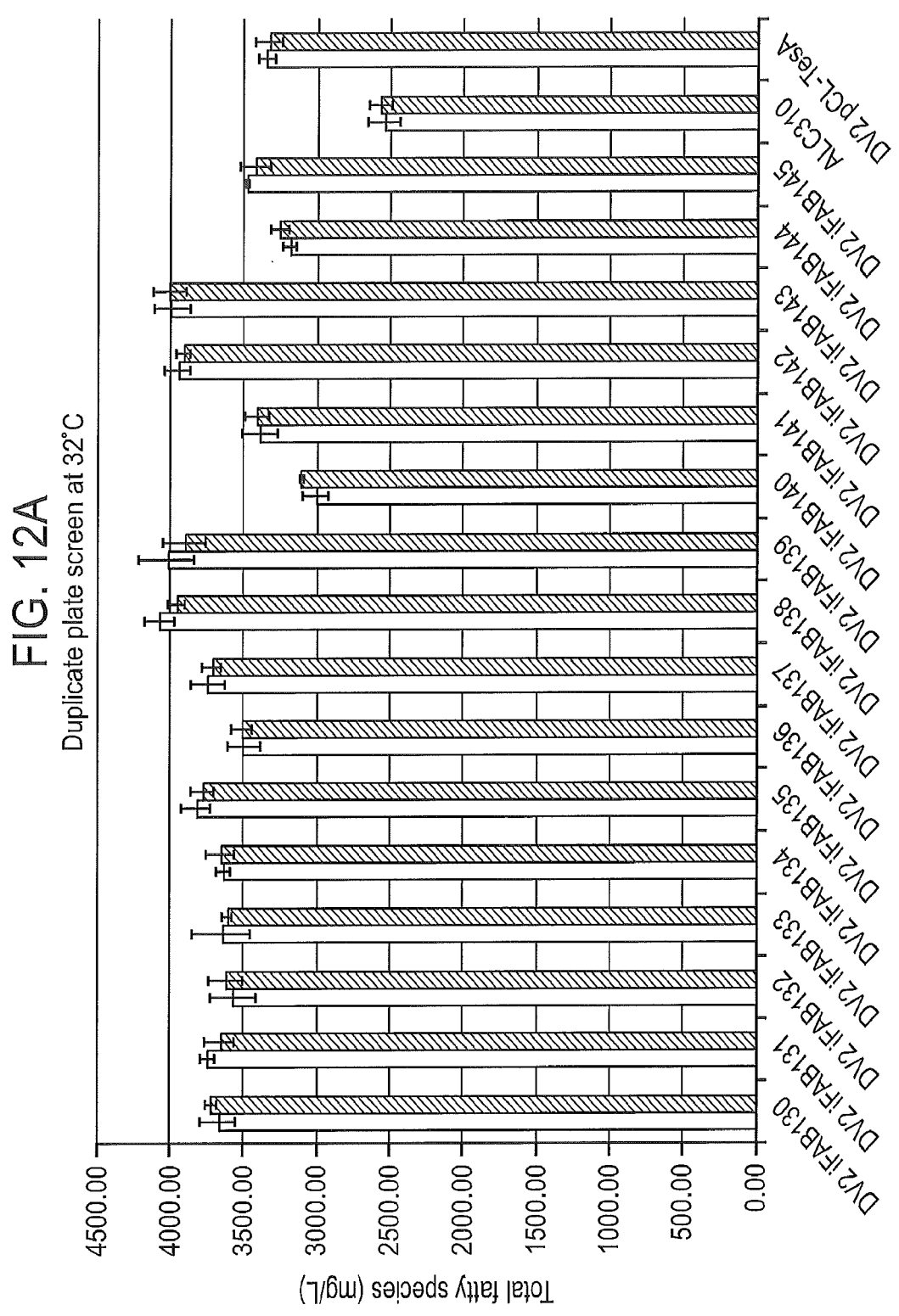
FIGS. 12A and 12B show data for production of Total Fatty Species (mg/L) from duplicate plate screens when plasmid pCL_P$_{trc}$_tesA was transformed into each of the iFAB-containing strains shown in the figures and a fermentation was run in FA2 media with 20 hours from induction to harvest at both 32° C.
Figure 12B:
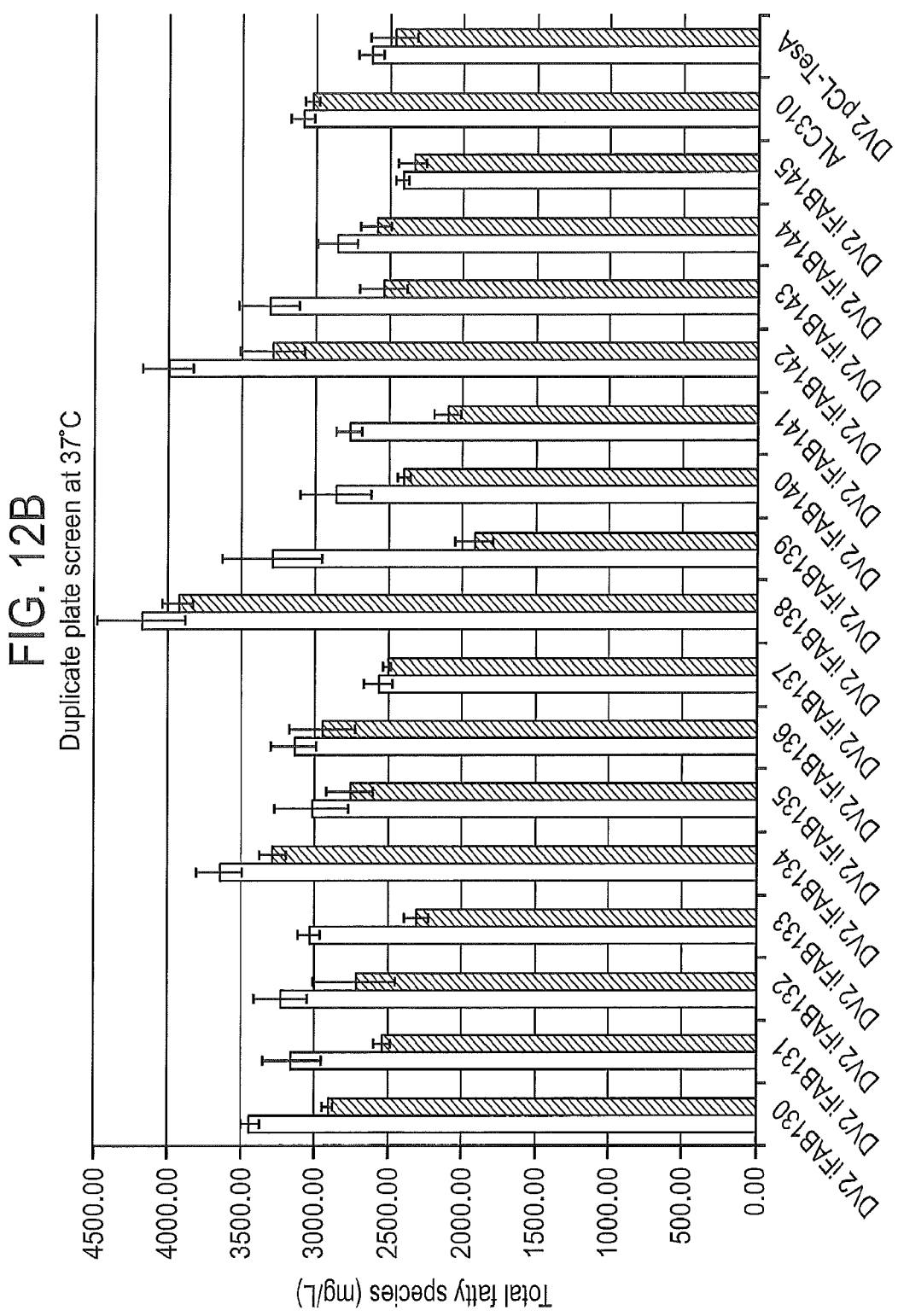

The plasmid pCL_P$_{trc}$_tesA was transformed into each of the strains and a fermentation was run in FA2 media with 20 hours from induction to harvest at both 32° C. and 37° C. Data for production of Total Fatty Species from duplicate plate screens is shown in FIGS. 12A and 12B. From this screen the best construct was determined to be DV2 with iFAB138. The sequence of iFAB138 in the genome of EG149 is presented as SEQ ID NO: 19.

Fatty Ester Production:

A full synthetic fab operon was integrated into the E. coli chromosome and evaluated for increased FAME production by expression in E. coli DAM1 pDS57. In addition, four synthetic acc operons from Corynebacterium glutamicum were coexpressed and evaluated for improved FAME productivity. Several strains were obtained that produced FAMEs at a faster rate and higher titers. The sixteen different iFAB operons (Table 5) were put under the control of the lacUV5 promoter and integrated into the IS5-11 site of E. coli DAM1. These strains were named DAM1 ifab130 to 145. They were transformed either with pDS57 (containing ester synthase 377) or pDS57 co-expressing different versions of acc operons, see above) for evaluation of FAME production. Exemplary plasmids are described in Table 6.

TABLE 6

Plasmids containing Ester Synthase ES9
(from *Marinobacter hydrocarbonclasticus*) and
Synthetic acc Operons (from *Corynebactrium glutamicum*)

| Plasmid | Genes |
|---|---|
| pTB.071 | pDS57-accCBDA |
| pTB.072 | pDS57-accCBDA-birA |
| pTB.073 | pDS57-accDACB |
| pTB.074 | pDS57-accDACB-birA | pDS57 = pCL_ptrc-ES9

The DAM1 ifab strains were analyzed in 96-well plates (4NBT medium), shake flasks (5NBT medium) (see above for medium description) and in fermenters at 32° C. The best results were obtained in 96-well plates and in shake flasks, where several DAM1 ifab strains with pDS57-acc-birA plasmids showed higher FAME titers. In particular, DAM1 ifab131, ifab135, ifab137, ifab138 and ifab143 with pDS57-accDACB-birA showed 20-40% improved titers indicating that in these strains a higher flux through the fatty acid pathway was achieved, which resulted in a better product formation rate (these results were reproducible in several independent experiments).

Effect of Overexpressing fabH and fabI on Fatty Acid Methyl Ester (FAME) Production:

Strategies to increase the flux through the fatty acid synthesis pathway in recombinant host cells include both overexpression of native fatty acid biosynthesis genes and expression of heterologous fatty acid biosynthesis genes. FabH and fabI are two fatty acid biosynthetic enzymes that have been shown to be feedback inhibited (Heath and Rock, JBC 271: 1833-1836 (1996)). A study was conducted to determine if FabH and FabI might be limiting the rate of FAME production. FabH and fabI homologues (from E. coli, B. subtilis, Acinetobacter baylyi ADP1, Marinobacter aquaeoli VT8, and Rhodococcus opacus) were overexpressed as a synthetic operon and evaluated in E. coli DAM1 pDS57 (a strain observed to be a good FAME producer). In one approach, fabHfabI operons were constructed from organisms that accumulate waxes (A. baylyi, M. aquaeoli) or triacylglycerides (R. opacus) and integrated into the chromosome of E. coli DAM1 pDS57. In a related approach, a synthetic acc operons from C. glutamicum were co-expressed (as described in Example 2, above). Eleven different fabHI operons were constructed (assembled in vitro) as summarized in Table 7. The fabHI operons were put under the control of IPTG inducible lacUV5 promoter and integrated into the IS5-11 site of E. coli DAM1. These strains were named as shown in the table below. They were transformed either with pDS57 (containing ester synthase 377) or pDS57 coexpressing different versions of acc operons for evaluation of FAME production.

TABLE 7

| | Genotype of Integrated fabHI Operons | |
|---|---|---|
| Strain | Genotype of additional fab operon | Plasmid |
| stEP117 | DAM1 ΔinsH::P$_{LACUV5}$ (snyRBS) EcfabH (synRBS) Bsfabl::kan | pDS57 |
| stEP118 | DAM1 ΔinsH::P$_{LACUV5}$ (snyRBS) EcfabH (synRBS) BsfabL::kan | pDS57 |
| stEP127 | DAM1 ΔinsH::P$_{LACUV5}$ (EcRBS) EcfabH (EcRBS) Bsfabl::kan | pDS57 |

TABLE 7-continued

Genotype of Integrated fabHI Operons

| Strain | Genotype of additional fab operon | Plasmid |
|---|---|---|
| stEP128 | DAM1 ΔinsH::P_LACUV5 (EcRBS) EcfabH (EcRBS) BsfabL::kan | pDS57 |
| stEP129 | DAM1 ΔinsH::P_LACUV5 (EcRBS) ADP1fabH (EcRBS) ADP1fabI::kan | pDS57 |
| stEP130 | DAM1 ΔinsH::P_LACUV5 (snyRBS) ADP1fabH (synRBS) ADP1fabI::kan | pDS57 |
| stEP131 | DAM1 ΔinsH::P_LACUV5 (snyRBS) VT8fabH1 (synRBS) VT8fabI::kan | pDS57 |
| stEP132 | DAM1 ΔinsH::P_LACUV5 (snyRBS) VT8fabH2 (synRBS) VT8fabI::kan | pDS57 |
| stEP133 | DAM1 ΔinsH::P_LACUV5 (EcRBS) VT8fabH1 (synRBS) VT8fabI::kan | pDS57 |
| stEP134 | DAM1 ΔinsH::P_LACUV5 (EcRBS) VT8fabH2 (synRBS) VT8fabI::kan | pDS57 |
| stEP151 | DAM1 ΔinsH::P_LACUV5 (snyRBS) RofabI (synRBS) RofabH::kan | pDS57 |
| stEP153 | DAM1 ΔinsH::P_LACUV5 (EcRBS) ADP1fabH (EcRBS) ADP1fabI::kan | pDS57-accCBDA |
| stEP154 | DAM1 ΔinsH::P_LACUV5 (EcRBS) ADP1fabH (EcRBS) ADP1fabI::kan | pDS57-accDACB |
| stEP155 | DAM1 ΔinsH::P_LACUV5 (EcRBS) ADP1fabH (EcRBS) ADP1fabI::kan | pDS57-accCBDA-birA |
| stEP156 | DAM1 ΔinsH::P_LACUV5 (EcRBS) ADP1fabH (EcRBS) ADP1fabI::kan | pDS57-accDACB-birA |
| stEP157 | DAM1 ΔinsH::P_LACUV5 (snyRBS) EcfabH (synRBS) BsfabI::kan | pDS57-accCBDA |
| stEP158 | DAM1 ΔinsH::P_LACUV5 (snyRBS) EcfabH (synRBS) BsfabI::kan | pDS57-accCBDA-birA |
| stEP159 | DAM1 ΔinsH::P_LACUV5 (EcRBS) EcfabH (synRBS) BsfabI::kan | pDS57-accCBDA |
| stEP160 | DAM1 ΔinsH::P_LACUV5 (EcRBS) EcfabH (synRBS) BsfabI::kan | pDS57-accCBDA-birA |
| stEP161 | DAM1 ΔinsH::P_LACUV5 (EcRBS) VT8fabH1 (synRBS) VT8fabI::kan | pDS57-accCBDA |
| stEP162 | DAM1 ΔinsH::P_LACUV5 (EcRBS) VT8fabH1 (synRBS) VT8fabI::kan | pDS57-accCBDA-birA |
| stEP163 | DAM1 ΔinsH::P_LACUV5 (EcRBS) VT8fabH2 (synRBS) VT8fabI::kan | pDS57-accCBDA |
| stEP164 | DAM1 ΔinsH::P_LACUV5 (EcRBS) VT8fabH2 (synRBS) VT8fabI::kan | pDS57-accCBDA-birA |

Bs: *Bacillus subtilis*;
Ec: *Escherichia coli*;
ADP1: *Acinetobacter* sp. ADP1;
VT8: *Marinobacter aquaeolei* VT8;
Ro: *Rhodococcus opacus* B4

Figure 13:
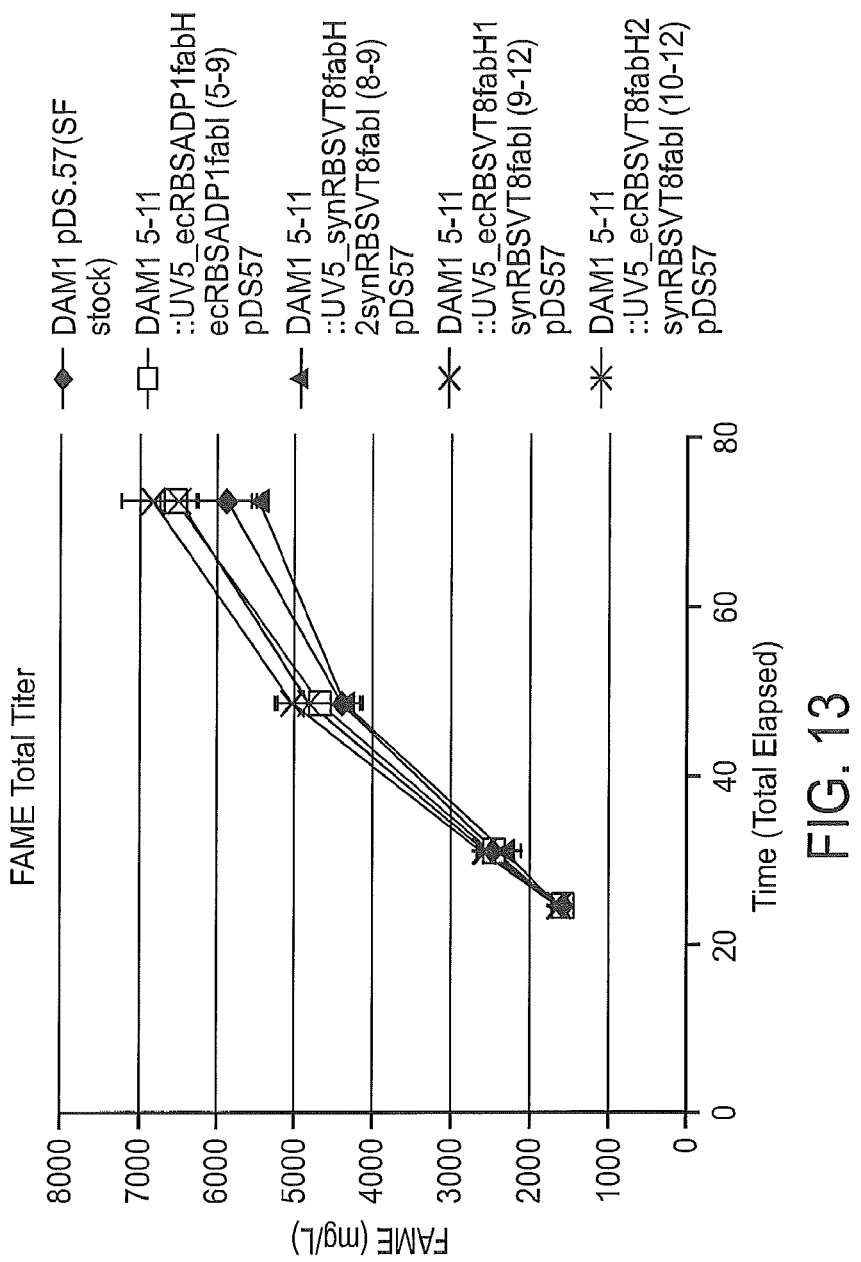
FIG. 13 shows FAME production of E. coli DAM1 with plasmid pDS57 and integrated fabHI operons. The fabH/I genes are from Marinobacter aquaeoli VT8 or from Acinetobacter baylyi ADP1. See Table 7 for a more details on the fabH/I operons in these strains.
Figure 14:
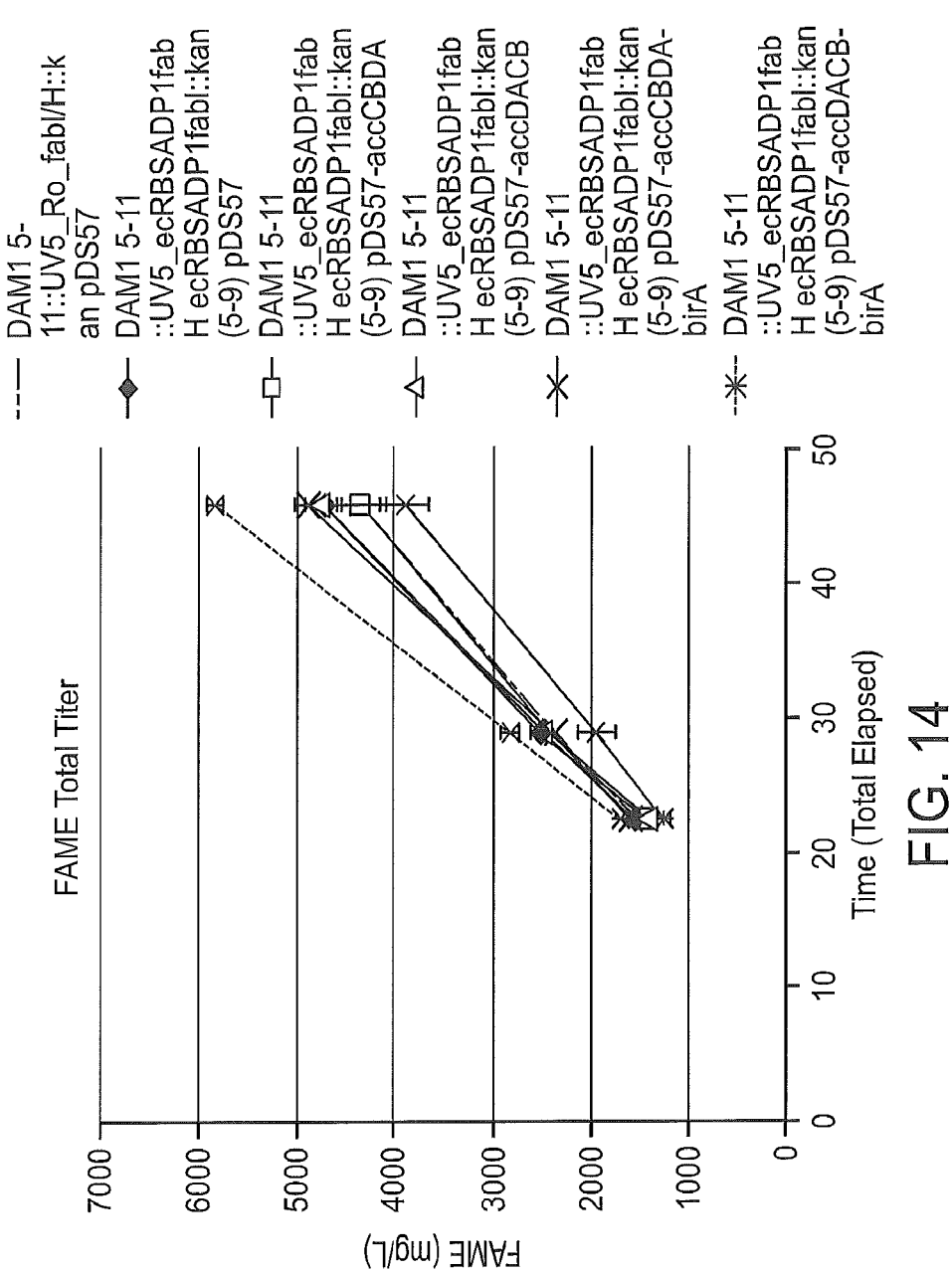
FIG. 14 shows FAME production of E. coli DAM1 with plasmid pDS57 and different configurations of the C. glutamicum acc genes as well as integrated fabHI operons. The strains contain the fabH/I genes from Rhodococcus opacus or Acinetobacter baylyi ADP1. See Table 7 for more details on the fabH/I and acc operons.

The DAM1 ifabHI strains were analyzed in 96-well plates (4NBT medium), shake flasks (5NBT medium) and in fermenters at 32° C. In a shake flask, a number of the ifabHI strains carrying pDS57 plasmid performed better than the control DAM1 pDS57 strain, reaching 10 to 1500 higher FAME titers (FIG. 13). Additional increase in FAME titers was obtained when ifabHI strains were transformed with pDS57-acc-birA plasmids, in particular an increase of 50% in FAME titers was observed in strain StEP156 (DAM1 IS5-11::lacUV5(ecRBS)ADP1fabH (ecRBS)ADP1fabI pDS57-accDACB-birA) (FIG. 14).

Figure 15:
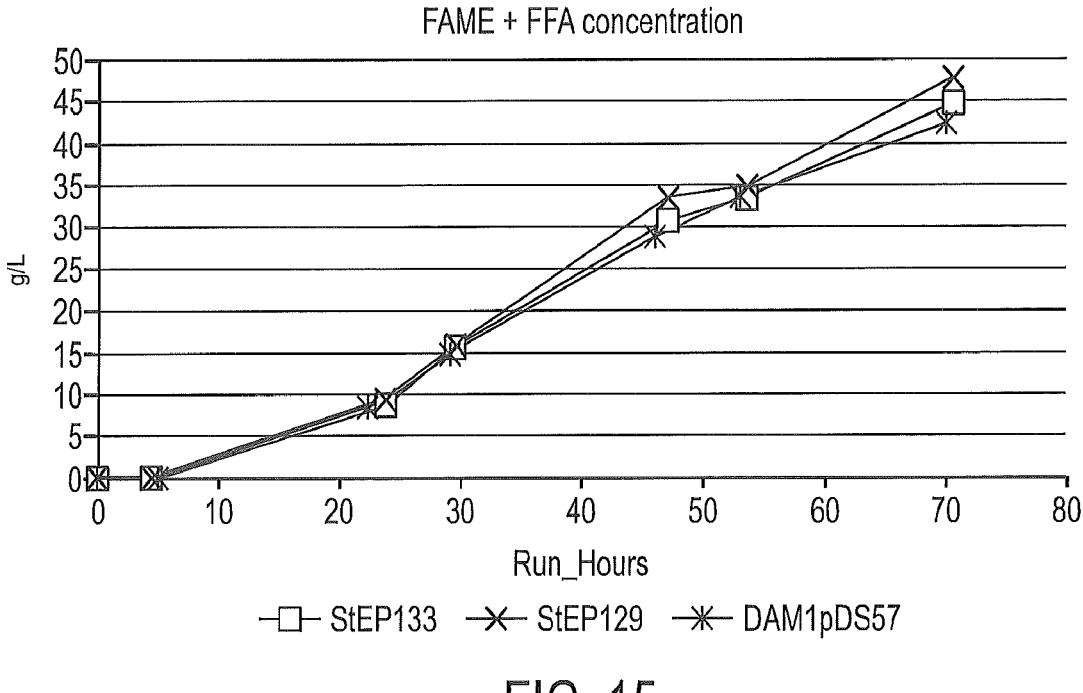
FIG. 15 shows FAME and FFA titers of two E. coli DAM1 pDS57 strains with integrated fabH/I genes strains selected from FIG. 13 compared to the control strain E. coli DAM1 pDS57.

Some of the strains with ifabHI were run in fermenters, where an increase in FAME titers, specific productivity and yield was also observed (FIG. 15), indicating that in these strains a higher flux through the fatty acid pathway was achieved, which resulted in a better product formation rate. In particular stEP129 (DAM1 5-11::UV5(ecRBS) ADP1fabH (ecRBS)ADP1fabI pDS57) showed higher FAME titers and yield in several independent fermentation runs. Other combinations of fabH and fabI may be used to achieve similar effects. Although FAME is exemplified here, this approach to alter fatty acid biosynthetic genes is a useful approach to increase production of any fatty acid derivative.

Effect of Inserting a Strong Promoter in Front of Operon FAB138 on Fatty Acid Methyl Ester (FAME) Production:

The lacUV5 promoter of iFAB138 was replaced by a T5 promoter (SEQ ID NO: 2) leading to higher levels of expression of iFAB138, as confirmed by mRNA analysis. The expression of iFAB138 from the T5 promoter resulted in a higher titer, yield and productivity of fatty esters. Strain shu.002 (Table 3) is isogenic to strain BD64 (Table 3) except that it contains the T5 promoter controlling expression of the iFAB138 operon (SEQ ID NO: 19).

TABLE 8

Primers used to Generate iT5_138 Cassette and
Verify its Insertion in New Strains

| Primer Name | SEQ ID NO | Sequence |
|---|---|---|
| DG405 | 20 | TTGTCCATCTTTATATAATTTGGGGGTAGGGTGTT CTTTATGTAAAAAAAACgtttTAGGATGCATATGG CGGCC |
| DG406 | 21 | GATAAATCCACGAATTTTAGGTTTGATGATCATTG GTCTCCTCCTGCAGGTGCGTGTTCGTCGTCATCGC AATTG |
| DG422 | 22 | ACTCACCGCATTGGTGTAGTAAGGCGCACC |
| DG423 | 23 | TGAATGTCATCACGCAGTTCCCAGTCATCC |
| EG744 | 24 | CCATCTTCTTTGTACAGACGTTGACTGAACATG |
| EG749 | 24 | GCACCATAGCCGTAATCCCACAGGTTATAG |
| oTREE047 | 26 | TGTCATTAATGGTTAATAATGTTGA |

Figure 16A:
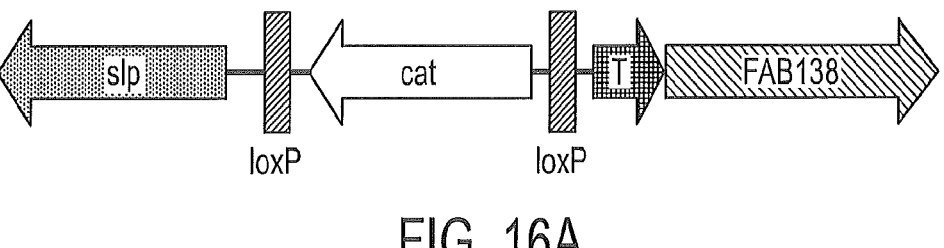
FIGS. 16A and 16B are a diagrammatic depiction of the iFAB138 locus, including a diagram of cat-loxP-P$_{T5}$ cassette integrated in front of iFAB138 (FIG. 16A); and a diagram of the PT5_iFAB138 region (FIG. 16B).
Figure 16B:
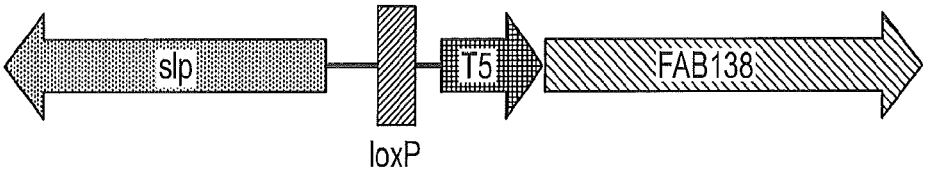

Primers DG405 and DG406 (Table 8) were used to amplify a cat-loxP and T5 promoter cassette adding 50 bp homology to each end of the PCR product, such that it could be integrated into any strain replacing the lacUV5 promoter regulating expression of the iFAB138 operon. The cat-loxP-T5 promoter was transformed into BD64/pKD46 strain. Transformants were recovered on LB+chloramphenicol plates at 37° C. overnight, patched to a fresh LB+chloramphenicol plate, and verified by colony PCR using primers DG422 and DG423. Plasmid pJW168 (Palmeros et al., *Gene* 247: 255-264 (2000)) was transformed into strain BD64 i-cat-loxP-T5_138 and selected on LB+carbenicillin plates at 32° C. In order to remove the cat marker, expression of the cre-recombinase was induced by IPTG. The plasmid pJW168 was removed by growing cultures at 42° C. Colonies were patched on LB+chloramphenicol and LB+carbenicillin to verify loss of pJW168 and removal of cat marker, respectively. The colony was also patched into LB as a positive control, all patched plates were incubated at 32° C. The removal of the cat marker was confirmed by colony PCR using primers DG422 and DG423. The resulting PCR product was verified by sequencing with primers EG744, EG749 and oTREE047, the strain was called shu.002. FIG. 16 shows the iFAB138 locus: a diagram of the cat-loxP-$P_{T5}$ cassette integrated in front of FAB138 (FIG. 16A) and a diagram of the $P_{T5}$_iFAB138 region (FIG. 16B). The sequence of the cat-loxP-T5 promoter integrated in front of iFAB138 with homology to integration site is presented as SEQ ID NO: 1 and the sequence of the iT5_FAB138 promoter region with homology to integration site is presented as SEQ ID NO: 2. There are a number of conditions that can lead to increased fatty acid flux. In this example increased fatty acid flux was achieved by altering the promoter strength of operon iFAB138. The expression of iFAB138 from the T5 promoter was beneficial, nonetheless, when this promoter change was combined with the insertion of yijP::Tn5 cassette further improvements were observed in titer, yield and productivity of fatty acid esters and other fatty acid derivatives (data not shown).

Example 4

Figure 17:
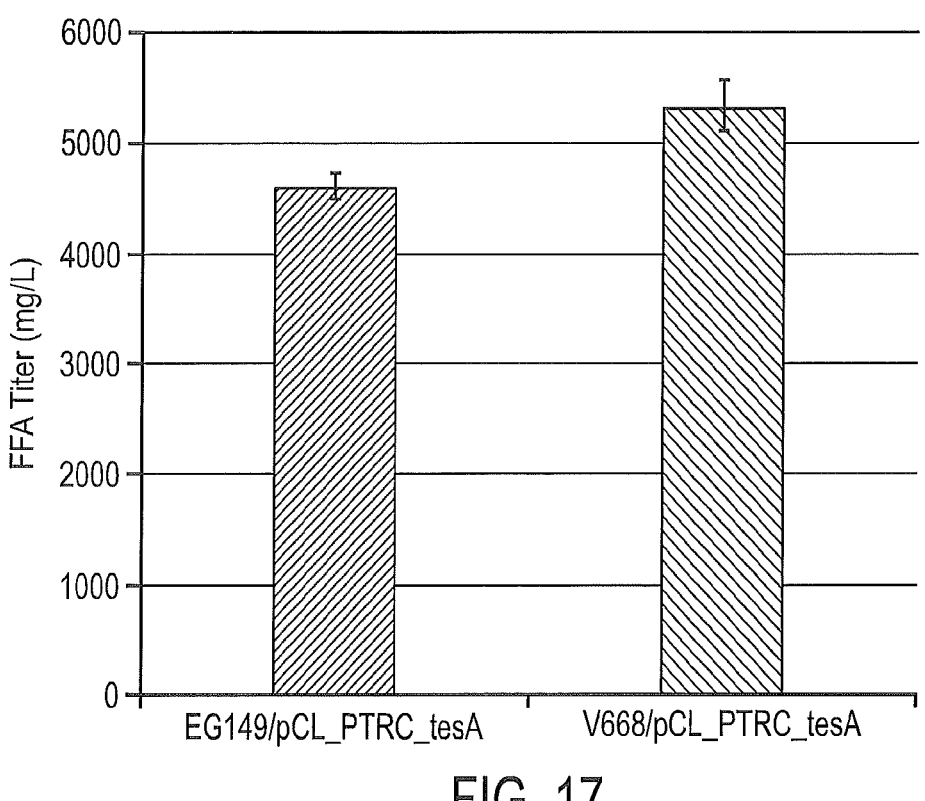
FIG. 17 shows that strain V668, which has the rph and ilvG genes repaired, produced a higher level of FFA than EG149, which has neither of the genes repaired.

Increasing the Amount of Free Fatty Acid (FFA) Product by Repairing the Rph and ilvG Mutations The ilvG and rph mutations were corrected in this strain resulting in higher production of FFA. Strains EG149 and V668 (Table 3) were transformed with pCL_$P_{trc}$_tesA. Fermentation was run at 32° C. in FA2 media for 40 hours to compare the FFA production of strains EG149 and V668 with pCL_$P_{trc}$_tesA. Correcting the rph and ilvG mutations resulted in a 116% increase in the FFA production of the base strain with pCL_$P_{trc}$_tesA. As seen in FIG. 17, V668/ pCL_$P_{trc}$_tesA produced more FFA than the EG149/pCL_ $P_{trc}$_tesA control. Since FFA is a precursor to the LS9 products, higher FFA production is a good indicator that the new strain can produce higher levels of LS9 products.

Example 5: Increased Production of Fatty Acid Derivatives by Transposon Mutagenesis—yijP Fatty Alcohol Production:

To improve the titer, yield, productivity of fatty alcohol production by E. coli, transposon mutagenesis and high-throughput screening was carried out and beneficial mutations were sequenced. A transposon insertion in the yijP strain was shown to improve the strain's fatty alcohol yield in both shake flask and fed-batch fermentations. The SL313 strain produces fatty alcohols. The genotype of this strain is provided in Table 3. Transposon clones were then subjected to high-throughput screening to measure production of fatty alcohols. Briefly, colonies were picked into deep-well plates containing LB, grown overnight, inoculated into fresh LB and grown for 3 hours, inoculated into fresh FA2.1 media, grown for 16 hours, then extracted using butyl acetate. The crude extract was derivatized with BSTFA (N,O-bis[Trim-ethylsilyl]trifluoroacetamide) and analyzed using GC/FID. Spectinomycin (100 mg/L) was included in all media to maintain selection of the pDG109 plasmid. Hits were selected by choosing clones that produced a similar total fatty species as the control strain SL313, but that had a higher percent of fatty alcohol species and a lower percent of free fatty acids than the control. Strain 68F11 was identified as a hit and was validated in a shake flask fermentation using FA2.1 media. A comparison of transposon hit 68F11 to control strain SL313 indicated that 68F11 produces a higher percentage of fatty alcohol species than the control, while both strains produce similar titers of total fatty species. A single colony of hit 68F11, named LC535, was sequenced to identify the location of the transposon insertion. Briefly, genomic DNA was purified from a 10 mL overnight LB culture using the kit ZR Fungal/Bacterial DNA MiniPrep™ (Zymo Research Corporation, Irvine, CA) according to the manufacturer's instructions. The purified genomic DNA was sequenced outward from the transposon using primers internal to the transposon:

```
DG150
                                    (SEQ ID NO: 27)
  5'-GCAGTTATTGGTGCCCTTAAACGCCTGGTTGCTACGCCTG-3'

DG131
                                    (SEQ ID NO: 28)
  5'-GAGCCAATATGCGAGAACACCCGAGAA-3'
```

Figure 18:
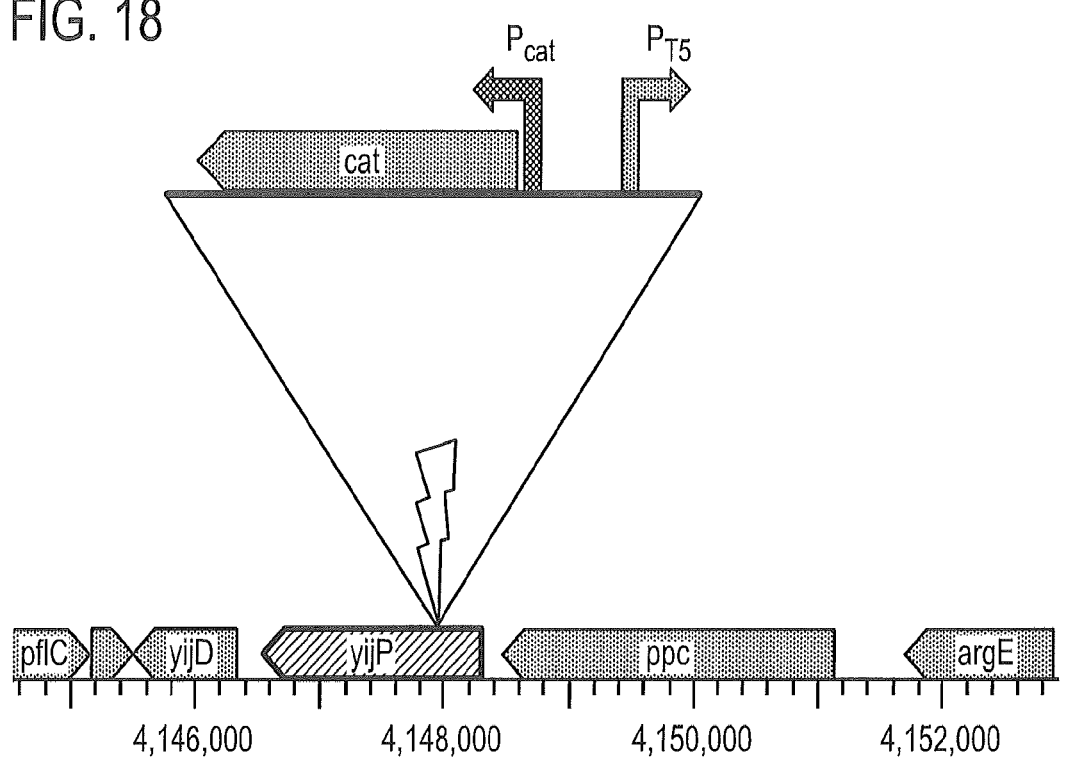
FIG. 18 is a diagrammatic depiction of a transposon cassette insertion in the yijP gene of strain LC535 (transposon hit 68F11). Promoters internal to the transposon cassette are shown, and may have effects on adjacent gene expression.

Strain LC535 was determined to have a transposon insertion in the yijP gene (FIG. 18). yijP encodes a conserved inner membrane protein whose function is unclear. The yijP gene is in an operon and co-transcribed with the ppc gene, encoding phosphoenolpyruvate carboxylase, and the yijO gene, encoding a predicted DNA-binding transcriptional regulator of unknown function. Promoters internal to the transposon likely have effects on the level and timing of transcription of yijP, ppc and yijO, and may also have effects on adjacent genes frwD, pflC, pfld, and argE. Promoters internal to the transposon cassette are shown in FIG. 18, and may have effects on adjacent gene expression. Strain LC535 was evaluated in a fed-batch fermentation on two different dates. Both fermentations demonstrated that LC535 produced fatty alcohols with a higher yield than control SL313, and the improvement was 1.3-1.9% absolute yield based on carbon input. The yijP transposon cassette was further evaluated in a different strain V940, which produces fatty alcohol at a higher yield than strain SL313. The yijP::Tn5-cat cassette was amplified from strain LC535 using primers:

```
LC277
                                    (SEQ ID NO: 29)
5'-CGCTGAACGTATTGCAGGCCGAGTTGCTGCACCGCTCCCGCCAGGCA

G-3'

LC278
                                    (SEQ ID NO: 30)
5'-GGAATTGCCACGGTGCGGCAGGCTCCATACGCGAGGCCAGGTTATCC

AACG-3'
```

This linear DNA was electroporated into strain SL571 and integrated into the chromosome using the lambda red recombination system. Colonies were screened using primers outside the transposon region:

```
DG407
                                    (SEQ ID NO: 31)
  5'-AATCACCAGCACTAAAGTGCGCGGTTCGTTACCCG-3'

DG408
                                    (SEQ ID NO: 32)
  5'-ATCTGCCGTGGATTGCAGAGTCTATTCAGCTACG-3'
```

A colony with the correct yijP transposon cassette was transformed with the production plasmid pV171.1 to produce strain D851. D851 was tested in a shake-flask fermentation against strain V940 that does not contain the yijP transposon cassette. The result of this fermentation showed that the yijP transposon cassette confers production of a higher percent of fatty alcohol by the D851 strain relative to the V940 strain and produces similar titers of total fatty species as the V940 control strain. Strain D851 was evaluated in a fed-batch fermentation on two different dates. Data from these fermentations is shown in Table 9 which illustrates that in 5-liter fed-batch fermentations, strains with the yijP::Tn5-cat transposon insertion had an increased total fatty species ("FAS") yield and an increase in percent fatty alcohol ("FALC"). The terms "total fatty species" and "total fatty acid product" may be used interchangeably herein with reference to the amount of fatty alcohols, fatty aldehydes and free fatty acids, as evaluated by GC-FID as described in International Patent Application Publication WO 2008/119082. The same terms may be used to mean fatty esters and free fatty acids when referring to a fatty ester analysis. As used herein, the term "fatty esters" includes beta hydroxy esters.

TABLE 9

Effect of yijP transposon insertion on titer and yield of FAS and FALC

| Strain | FAS Titer | FAS Yield | Percent FALC | FALC Yield |
|---|---|---|---|---|
| V940 | 68 g/L | 18.7% | 95.0% | 17.8% |
| D851 | 70 g/L | 19.4% | 96.1% | 18.6% |
| V940 | 64 g/L | 18.4% | 91.9% | 16.9% |
| D851 | 67 g/L | 19.0% | 94.0% | 17.8% |

Tank Fermentation Method:

To assess production of fatty acid and fatty acid derivatives in tank a glycerol vial of desired strain was used to inoculate 20 mL LB+spectinomycin in shake flask and incubated at 32° C. for approximately six hours. 4 mL of LB culture was used to inoculate 125 mL Low PFA Seed Media (below), which was then incubated at 32° C. shaker overnight. 50 mL of the overnight culture was used to inoculate 1 L of Tank Media. Tanks were run at pH 7.2 and 30.5° C. under pH stat conditions with a maximum feed rate of 16 g/L/hr glucose.

TABLE 10

Low P FA Seed Media:

| Component | Concentration |
|---|---|
| $NH_4Cl$ | 2 g/L |
| NaCl | 0.5 g/L |
| $KH_2PO_4$ | 1 g/L |
| $MgSO_4—7H_2O$ | 0.25 g/L |
| $CaCl_2—2H_2O$ | 0.015 g/L |
| Glucose | 20 g/L |
| TM2 Trace Minerals solution | 1 mL/L |
| Ferric citrate | 10 mg/L |
| Bis Tris buffer (pH 7.0) | 100 mM |
| Spectinomycin | 115 mg/L |

TABLE 11

Tank Media

| Component | Concentration |
|---|---|
| $(NH_4)_2SO_4$ | 0.5 g/L |
| $KH_2PO_4$ | 3.0 g/L |
| Ferric Citrate | 0.034 g/L |
| TM2 Trace Minerals Solution | 10 mL/L |
| Casamino acids | 5 g/L |

TABLE 11-continued

Tank Media

| Component | Concentration |
|---|---|
| Post sterile additions | |
| $MgSO_4—7H_2O$ | 2.2 g/L |
| Trace Vitamins Solution | 1.25 mL/L |
| Glucose | 5 g/L |
| Inoculum | 50 mL/L |

Further studies suggest that the improved titer and yield of FAS and FALC in strains with the yijP transposon insertion is due to reduction in the activity of phosphoenolpyruvate carboxylase (ppc). A ppc enzyme assay was carried out in-vitro in the following strains to evaluate this hypothesis.

1) Δppc=DG14 (LC942 Δppc::cat-sacB/pLC56)
2) wt-ppc=DG16 (LC942/pLC56)
3) yijP::Tn5=DG18 (LC942 yijP::Tn5-cat/pLC56)

Ppc activity was measured in cells grown in a shake flask fermentation using a standard shake flask protocol in FA2.3 media (described above) and harvested 12-16 hours after induction. Approximately 5 mL of cells were centrifuged and the cell paste was suspended in BugBuster Protein Extraction Reagent (Novagen) with a protease inhibitor cocktail solution. The cell suspension was incubated with gentle shaking on a shaker for 20 min. Insoluble cell debris was removed by centrifugation at 16,000×g for 20 min at 4° C. followed by transferring the supernatant to a new tube. Ppc activity in the cell lysate was determined by a coupling reaction with citrate synthase using following reaction mixture: 0.4 mM acetyl-CoA, 10 mM phosphoenolpyruvate, 0.5 mM monobromobimane, 5 mM $MgCl_2$, 10 mM $NaHCO_3$, and 10 units citrate synthase from porcine heart in 100 mM Tris-HCl (pH 8.0). The formation of CoA in the reaction with citrate synthase using oxaloacetate and acetyl-CoA was monitored photometrically using fluorescent derivatization of CoA with monobromobimane. The Ppc assay results showed that the yijP::Tn5-cat transposon cassette decreased the Ppc activity in the cell by 2.7 fold compared to wild type cells. The cells with deletion of ppc did not grow well and the activity was about 10 times lower than wild type cells. The results also indicate that the highest yield of fatty alcohol production requires a level of Ppc expression lower than the wild-type level. Proteomics data was also collected to assess the abundance of the Ppc protein in two strains with and without the yijP::Tn5-cat transposon cassette. Protein samples were collected from strains V940 and D851 grown in bioreactors under standard fatty alcohol production conditions (described above). Samples were taken at two different time points: 32 and 48 hours and prepared for analysis.

Sample collection and protein isolation was carried out as follows:

20 ml of fermentation broth were collected from each bioreactor at each time point. Samples were quenched with ice-cold PBS and harvested by centrifugation (4500 rpm/10 min) at 4° C. Cell pellet was washed with ice-cold PBS and centrifuged one more time and stored at −80° C. for further processing.

Total protein extraction was performed using a French press protocol. Briefly, cell pellets were resuspended in 7 ml of ice-cold PBS and French pressed at 2000 psi twice to ensure complete lysing of the bacteria. Samples were centrifuged for 20 min at 10000 rpm at 4° C. to separate non-lysed cells and cell debris from the protein fraction. Total protein concentration of clear lysate was determined using BCA Protein Assay Reagent. Samples were diluted to 2 mg proteins/ml concentration and frozen at –80° C.

Samples were resuspended in the appropriate buffer and trypsinized overnight at 37° C. and lyophilized. Fragmented protein samples were labeled with isotopically enriched methylpiperazine acetic acid at room temperature for 30 min. Labeled samples were separated using cation exchange liquid chromatography and subjected to mass spectroscopy analysis using an ion trap mass spectrometer. Raw data was normalized using background subtraction and bias correction.

Proteomics data showed a significant reduction in the relative abundance of Ppc protein in D851 strain when compared to V940 at 32 hours and 48 hours. D851 had about 15% of the Ppc levels of V940 at 32 hours and about 35% of the Ppc levels of V940 at 48 hours. These data show that the yijP::Tn5-cat transposon cassette results in a significant reduction in Ppc abundance in the cell. This suggests that the observed benefits to fatty alcohol production by strains harboring the yijP::Tn5-cat transposon hit is due to reducing the amount of Ppc protein.

These results suggest that altering ppc activity can improve the yield of fatty acid derivatives. There are a number of ways to alter the expression of the ppc gene, and the yijP transposon insertion is one way to accomplish this. Without wanting to be bound by theory, if the effect of reducing phosphoenolpyruvate carboxylase activity is to limit the flow of carbon through the TCA cycle, one could achieve similar results by decreasing the activity of citrate synthase (gltA) or slowing the TCA cycle by decreasing the activity of any of the enzymes involved in the TCA cycle.

Example 6

Increased Flux Through the Fatty Acid Synthesis Pathway—Acyl Carrier Protein (ACP) Mediated Fatty Alcohol Production When terminal pathway enzymes from sources other than *E. coli* are expressed in *E. coli* as the heterologous host to convert fatty acyl-ACPs to products, limitations may exist in the recognition, affinity and/or turnover of the recombinant pathway enzyme towards the *E. coli* fatty acyl-ACPs. Note that although ACP proteins are conserved to some extent in all organisms, their primary sequence can differ significantly. To test this hypothesis the acp genes from several cyanobacteria were cloned downstream from the *Synechococcus elongatus* PCC7942 acyl-ACP reductase (AAR) present in pLS9-185, which is a pCL1920 derivative. In addition, the sfp gene (Accession no. X63158; SEQ ID NO: 53 from *Bacillus subtilis*, encoding a phosphopantetheinyl transferase with broad substrate specificity, was cloned downstream of the respective acp genes. This enzyme is involved in conversion of the inactive apo-ACP to the active holo-ACP. The plasmids constructed are described in Table 12.

TABLE 12

Plasmids Coexpressing Cyanobacterial ACP with and without
*B. subtilis* sfp Downstream from *S. elongatus* PCC7942 AAR

| Base plasmid | ACP Source | ACP SEQ ID NO. (DNA/ Polypeptide) | Without sfp | With sfp |
|---|---|---|---|---|
| pLS9-185 | *Synechococcus elongatus* 7942 | 49/50 | pDS168 | pDS168S |
| pLS9-185 | *Synechocystis* sp. 6803 | 45/46 | pDS169 | not available |
| pLS9-185 | *Prochlorococcus marinus* MED4 | 47/48 | pDS170 | pDS170S |
| pLS9-185 | *Nostoc punctiforme* 73102 | 43/44 | pDS171 | pDS171S |
| pLS9-185 | *Nostoc* sp. 7120 | 51/52 | pDS172 | pDS172S |

Figure 19:
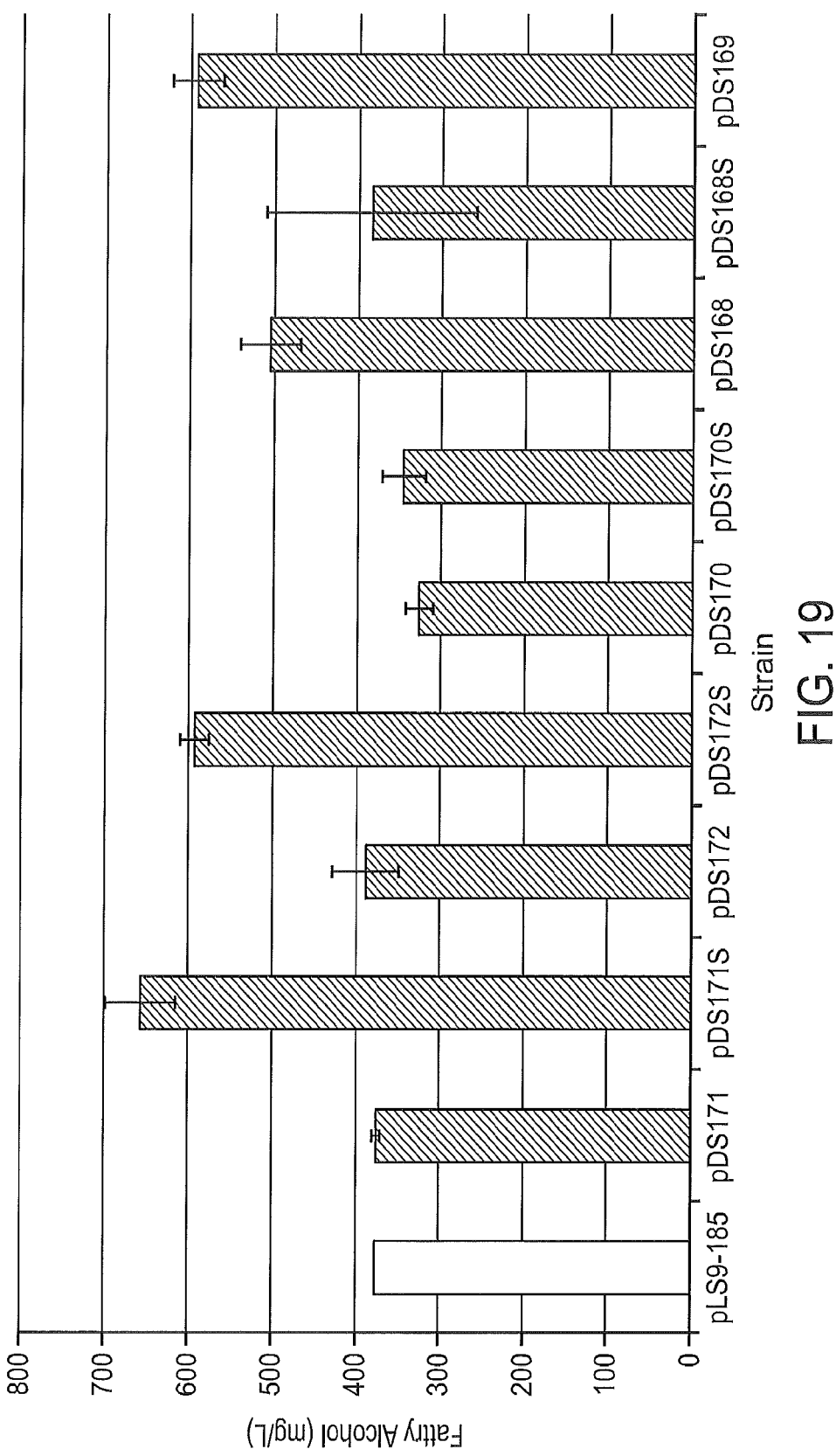
FIG. 19 illustrates fatty alcohol production in E. coli DV2 expressing Synechococcus elongatus acyl-ACP reductase (AAR) and coexpressing various cyanobacterial acyl carrier proteins (ACPs). Details regarding the source of the ACPs are provided in Table 12.

All the acp genes were cloned with a synthetic RBS into the EcoRI site immediately downstream of the aar gene in pLS9-185 using InFusion technology (Clontech Laboratories, Inc., Mountain View, CA). The EcoRI site was reconstructed downstream of the acp gene. Similarly, the *B. subtilis* sfp gene was InFusion cloned into this EcoRI site along with a synthetic RBS. All plasmids were transformed into *E. coli* MG1655 DV2 (Table 3). The control for these experiments was the expression of AAR alone (pLS9-185). The results from standard shake flask fermentation experiments are shown in FIG. 19. Significant improvement in fatty alcohol titers were observed in strains containing the plasmids pDS171S, pDS172S, pDS168 and pDS169 demonstrating that ACP overexpression can be beneficial for fatty alcohol production, in this case presumably by aiding in the recognition, affinity and/or turnover of acyl-ACPs by the heterologous terminal pathway enzyme. (See Table 12 for the source of the ACPs and presence or absence of sfp).

Figure 20:
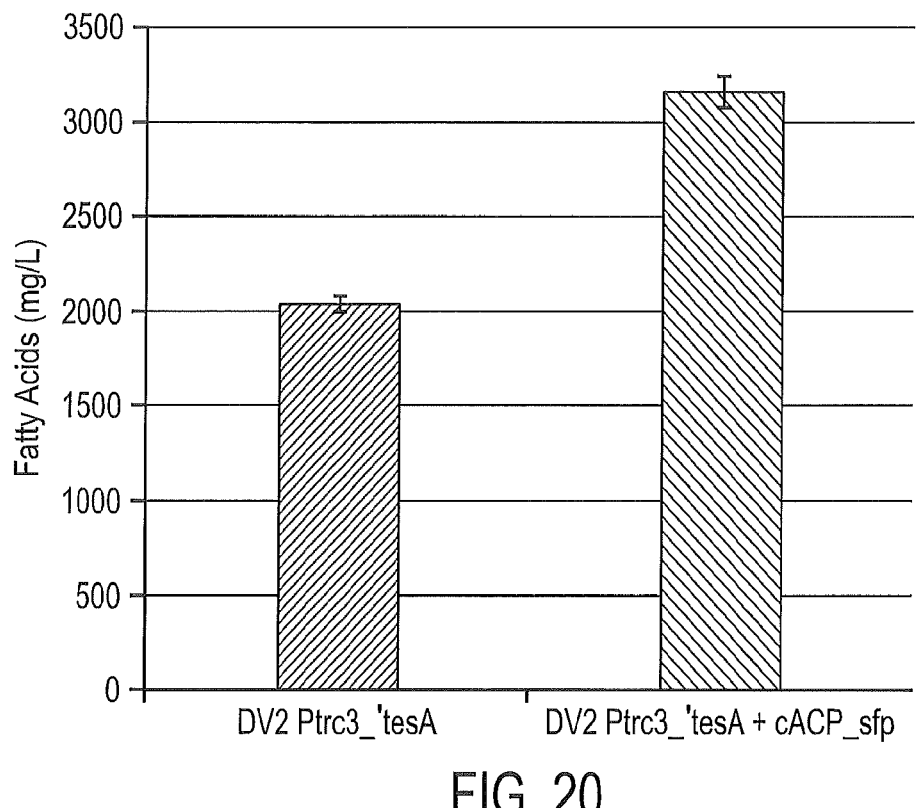
FIG. 20 illustrates fatty acid production in E. coli DV2 expressing leaderless E. coli thioesterase 'tesA and coexpressing a cyanobacterial acyl carrier protein (cACP) and B. subtilis sfp.

Fatty Acid Production:

In order to evaluate if the overexpression of an ACP can also increase free fatty acid production, one cyanobacterial ACP gene with sfp was amplified from pDS171s (Table 12) and cloned downstream from 'tesA into a pCL vector. The resulting operon was under the control of the Ptrc3 promoter, which provides slightly lower transcription levels than the $P_{trc}$ wildtype promoter. The construct was cloned into *E. coli* DV2 and evaluated for fatty acid production. The control strain contained the identical plasmid but without cyanobacterial ACP and *B. subtilis* sfp. The results from a standard microtiter plate fermentation experiment are shown in FIG. 20. Significant improvement in fatty acid titer was observed in the strain coexpressing the heterologous ACP demonstrating that ACP overexpression can be beneficial for fatty acid production, in this case presumably by increasing the flux through the fatty acid biosynthetic pathway.

We claim:

1. A recombinant bacterial host cell expressing a polypeptide having 3-hydroxy-acyl-[acp] dehydratase activity;
   wherein the polypeptide having 3-hydroxy-acyl-[acp] dehydratase activity is FabA;
   wherein the recombinant bacterial host cell expresses one or more additional polypeptides, and the one or more additional polypeptides are FabV, FabH, FabD, FabG, and FabF; and
   wherein the recombinant bacterial host cell produces a fatty acid derivative composition at a higher titer, yield, or productivity than a corresponding wild-type host cell when cultured in a medium containing a carbon source.

2. The recombinant bacterial host cell of claim 1,
   wherein the polypeptide with 3-hydroxy-acyl-[acp] dehydratase activity is FabA from *Salmonella typhimurium*; and
   wherein the one or more additional polypeptides are FabV from *Vibrio cholerae*; FabH from *Salmonella typhimurium, Acinetobacter* sp. ADP1, *Marinobacter aquaeoli* VT8, or *Rhodococcus opacus* B4; FabD from *Salmonella typhimurium*; FabG from *Salmonella typhimurium*; and FabF from *Clostridium acetobutylicum*.

3. The recombinant bacterial host cell of claim 1, wherein the polypeptide with 3-hydroxy-acyl-[acp] dehydratase activity and the one or more additional polypeptides are (1) heterologous, or (2) are native and are overexpressed.

4. The recombinant bacterial host cell of claim 1, further comprising a genetically engineered polynucleotide sequence encoding an acyl carrier protein (ACP), wherein the recombinant bacterial host cell produces a fatty acid derivative composition at a higher titer, yield, or productivity than a corresponding wild type host cell when cultured in a medium containing a carbon source under conditions effective to express said ACP.

5. The recombinant bacterial host cell of claim 4, wherein the ACP is derived from the same organism as a terminal pathway enzyme expressed in the recombinant bacterial host cell, and wherein the terminal pathway enzyme cleaves any acyl-ACP species that is part of a fatty acid biosynthetic pathway.

6. The recombinant bacterial host cell of claim 1, wherein the recombinant bacterial host cell further comprises a recombinant polynucleotide encoding a polypeptide that has phosphopantetheinyl transferase activity.

7. The recombinant bacterial host cell of claim 6, wherein the polypeptide that has phosphopantetheinyl transferase activity is encoded by an sfp gene.

8. The recombinant bacterial host cell of claim 1, wherein the recombinant bacterial host cell further comprises a recombinant polynucleotide encoding a polypeptide that has acetyl-CoA carboxylase activity.

9. The recombinant bacterial host cell of claim 8, further comprising a recombinant polynucleotide encoding a polypeptide that has phosphopantetheinyl transferase activity.

* * * * *